US012343392B2

(12) United States Patent
Backman et al.

(10) Patent No.: US 12,343,392 B2
(45) Date of Patent: Jul. 1, 2025

(54) COMPOSITIONS INCLUDING SBI ADJUVANTS AND METHODS OF USE THEREOF

(71) Applicant: Helix Nanotechnologies Inc., Boston, MA (US)

(72) Inventors: Kyle Backman, South San Francisco, CA (US); Nikhil Dhar, Boston, MA (US); Nikolai Eroshenko, Boston, MA (US); Taylor Gill, Cambridge, MA (US); Kemo Jammeh, Brighton, MA (US); Marianna Keaveney, Walpole, MA (US); Justin Quinn, Malden, MA (US); Hannu Rajaniemi, Corte Madera, CA (US); Everett Webster, Boston, MA (US)

(73) Assignee: Helix Nanotechnologies Inc, Boston, MA (US)

( * ) Notice: Subject to any disclaimer, the term of this patent is extended or adjusted under 35 U.S.C. 154(b) by 0 days.

(21) Appl. No.: 18/235,464

(22) Filed: Aug. 18, 2023

(65) Prior Publication Data

US 2024/0082388 A1 Mar. 14, 2024

Related U.S. Application Data

(62) Division of application No. 17/685,717, filed on Mar. 3, 2022, now Pat. No. 11,771,758.

(60) Provisional application No. 63/156,860, filed on Mar. 4, 2021.

(51) Int. Cl.

| | |
|---|---|
| ***C07K 14/47*** | (2006.01) |
| ***A61K 39/215*** | (2006.01) |
| ***C07K 14/11*** | (2006.01) |
| ***C07K 14/165*** | (2006.01) |
| ***C07K 14/31*** | (2006.01) |
| *A61K 39/00* | (2006.01) |

(52) U.S. Cl.

CPC ............ *A61K 39/215* (2013.01); *C07K 14/11* (2013.01); *C07K 14/165* (2013.01); *C07K 14/31* (2013.01); *C07K 14/472* (2013.01); *A61K 2039/575* (2013.01)

(58) Field of Classification Search

None

See application file for complete search history.

(56) References Cited

U.S. PATENT DOCUMENTS

| | | | |
|---|---|---|---|
| 2019/0282683 A1 | 9/2019 | Van Den Elsen et al. | |
| 2020/0188481 A1* | 6/2020 | Hamill ............... | A61K 38/1703 |
| 2022/0362373 A1 | 11/2022 | Backman et al. | |
| 2023/0302116 A1* | 9/2023 | Hecht .................... | A61K 39/12 |

FOREIGN PATENT DOCUMENTS

| | | | |
|---|---|---|---|
| CN | 1209455 | A | 3/1999 |
| CN | 1374871 | A | 10/2002 |
| CN | 101448854 | A | 6/2009 |
| WO | WO-2002/072792 | A2 | 9/2002 |
| WO | WO-2007/138328 | A2 | 12/2007 |
| WO | WO-2012/042213 | A1 | 4/2012 |
| WO | WO-2018/096089 | A1 | 5/2018 |
| WO | WO-2021/022008 | A1 | 2/2021 |
| WO | WO-2022/187424 | A1 | 9/2022 |

OTHER PUBLICATIONS

Almansoor (Development of vaccine conjugates based on Dengue virus using staphylococcal immune evasion protein, 2017, p. 1-66).*

Almansoor 2017.*

Yang, Y. et al., Utilization of Staphylococcal Immune Evasion Protein Sbi as a Novel Vaccine Adjuvant, Frontiers in Immunology, 9(3139):1-17 (2019).

Yang, J. et al., A vaccine targeting the RBD of the S protein of SARS-CoV-2 induces protective immunity, Nature, 586(7830):572-577 (2020).

Written Opinion for PCT/US22/18610, 13 pages (mailed Mar. 6, 2022).

Sun, S. et al., Recombinant Fe-fusion vaccine of RBD induced protection against SARS-CoV-2 in nonhuman primate and mice, bioRxiv, (2020).

Raymond, D. D. et al., Conserved epitope on influenza-virus hemagglutinin head defined by a vaccine-induced antibody, PNAS 115(1):168-173 (2018).

Pardi, N., et al., mRNA vaccines—a new era in vaccinology, Nature Reviews Drug Discovery, 17: 261-279, Tables 1 and 2; mRNA vaccines against infectious diseases on p. 267, 17(4): 261-279 (2018).

Nie, J. et al., Quantification of SARS-CoV-2 neutralizing antibody by a pseudotyped virus-based assay, Nat Biotech, 15:3699-3715 (2020).

International Search Report for PCT/US22/18610, 9 pages (mailed Mar. 6, 2022).

Clark, E. A. et al., A structural basis for Staphylococcal complement subversion: X-ray structure of the complement-binding domain of *Staphylococcus aureus* protein Sbi in complex with ligand C3d, Mol Immunol., 48(4): 452-462 (2011).

Burman, J. D. et al., Interaction of Human Complement with Sbi, a Staphylococcal Immunoglobulin-binding Protein: Indications of a Novel Mechanism of Complement Evasion by *Staphylococcus aureus**, J. Biol. Chem; 283:17579-17593 (2008).

Amanat, F. et al., A serological assay to detect SARS-CoV-2 seroconversion in humans, Nat Med, 26:1033-1036 (2020).

Bridges, J. P. et al., Respiratory epithelial cell responses to SARS-CoV-2 in COVID-19, Thorax, 77(2):203-209 (2022).

(Continued)

*Primary Examiner* — Agnieszka Boesen

(74) *Attorney, Agent, or Firm* — Choate, Hall & Stewart LLP; Stephanie L. Schonewald; Mandeep Kaur

(57) ABSTRACT

Disclosed herein are fusion polypeptides comprising: (i) a fragment antigen comprising an epitope of a target protein antigen; and (ii) a complement binding polypeptide. The disclosure also provides fusion polynucleotides (e.g., mRNA) encoding the same. Also disclosed herein are methods of making and using the fusion polypeptides and fusion polynucleotides of the present disclosure.

28 Claims, 10 Drawing Sheets

Specification includes a Sequence Listing.

(56) References Cited

OTHER PUBLICATIONS

Dempsey, P. W. et al., C3d of Complement as a Molecular Adjuvant Bridging Innate and Acquired Immunity, Science, 271:348-350 (1996).
Kleanthous, H. et al., Scientific rationale for developing potent RBD-based vaccines targeting COVID-19, Nature, 1-10 (2021).
Lin, D. et al., Effectiveness of Bivalent Boosters against Severe Omicron Infection, The New England Journal of Medicine, 1-3 (2023).
Lyubchenko, T. et al., Coligation of the B Cell Receptor with Complement Receptor Type 2 (CR2/CD21) Using Its Natural Ligand C3dg: Activation without Engagement of an Inhibitory Signaling y1, The Journal of Immunology, 1-9 (2005).
Smith, E. et al., The Sbi Protein Is a Multifunctional Immune Evasion Factor of *Staphylococcus aureus*, Infection and Immunity, 79(9):3801-3809 (2011).

* cited by examiner a.

SEQUENCE LISTING

```
Sequence total quantity: 74
SEQ ID NO: 1            moltype = AA  length = 20
FEATURE                 Location/Qualifiers
source                  1..20
                        mol_type = protein
                        organism = Homo sapiens
SEQUENCE: 1
MYRMQLLSCI ALSLALVTNS                                              20

SEQ ID NO: 2            moltype = AA  length = 13
FEATURE                 Location/Qualifiers
source                  1..13
                        mol_type = protein
                        organism = Severe acute respiratory syndrome coronavirus 2
SEQUENCE: 2
MFVFLVLLPL VSS                                                     13

SEQ ID NO: 3            moltype = AA  length = 197
FEATURE                 Location/Qualifiers
source                  1..197
                        mol_type = protein
                        organism = Severe acute respiratory syndrome coronavirus 2
SEQUENCE: 3
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSNN LDSKVGGNYN  120
YLYRLFRKSN LKPFERDIST EIYQAGSTPC NGVEGFNCYF PLQSYGFQPT NGVGYQPYRV  180
VVLSFELLHA PATVCGP                                                 197

SEQ ID NO: 4            moltype = AA  length = 118
FEATURE                 Location/Qualifiers
source                  1..118
                        mol_type = protein
                        organism = Severe acute respiratory syndrome coronavirus 2
SEQUENCE: 4
IAPGQTGKIA DYNYKLPDDF TGCVIAWNSN NLDSKVGGNY NYLYRLFRKS NLKPFERDIS  60
TEIYQAGSTP CNGVEGFNCY FPLQSYGFQP TNGVGYQPYR VVVLSFELLH APATVCGP    118

SEQ ID NO: 5            moltype = AA  length = 98
FEATURE                 Location/Qualifiers
source                  1..98
                        mol_type = protein
                        organism = Severe acute respiratory syndrome coronavirus 2
SEQUENCE: 5
TGCVIAWNSN NLDSKVGGNY NYLYRLFRKS NLKPFERDIS TEIYQAGSTP CNGVEGFNCY  60
FPLQSYGFQP TNGVGYQPYR VVVLSFELLH APATVCGP                          98

SEQ ID NO: 6            moltype = AA  length = 90
FEATURE                 Location/Qualifiers
source                  1..90
                        mol_type = protein
                        organism = Severe acute respiratory syndrome coronavirus 2
SEQUENCE: 6
SNNLDSKVGG NYNYLYRLFR KSNLKPFERD ISTEIYQAGS TPCNGVEGFN CYFPLQSYGF  60
QPTNGVGYQP YRVVVLSFEL LHAPATVCGP                                   90

SEQ ID NO: 7            moltype = AA  length = 48
FEATURE                 Location/Qualifiers
source                  1..48
                        mol_type = protein
                        organism = Severe acute respiratory syndrome coronavirus 2
SEQUENCE: 7
CNGVEGFNCY FPLQSYGFQP TNGVGYQPYR VVVLSFELLH APATVCGP               48

SEQ ID NO: 8            moltype = AA  length = 10
FEATURE                 Location/Qualifiers
source                  1..10
                        mol_type = protein
                        organism = Severe acute respiratory syndrome coronavirus 2
SEQUENCE: 8
KKSTNLVKNK                                                         10

SEQ ID NO: 9            moltype = AA  length = 42
FEATURE                 Location/Qualifiers
```

```
source                  1..42
                        mol_type = protein
                        organism = Staphylococcus aureus
SEQUENCE: 9
IENADKAIKD FQDNKAPHDK SAAYEANSKL PKDLRDKNNR FV                    42

SEQ ID NO: 10           moltype = AA  length = 58
FEATURE                 Location/Qualifiers
source                  1..58
                        mol_type = protein
                        organism = Staphylococcus aureus
SEQUENCE: 10
EKVSIEKAIV RHDERVKSAN DAISKLNEKD SIENRRLAQR EVNKAPMDVK EHLQKQLD    58

SEQ ID NO: 11           moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 11
GGGGSGGGGS GGGGS                                                  15

SEQ ID NO: 12           moltype = AA  length = 229
FEATURE                 Location/Qualifiers
REGION                  1..229
                        note = Description of Artificial Sequence: Synthetic
                         polypeptide
source                  1..229
                        mol_type = protein
                        organism = synthetic construct
SEQUENCE: 12
MYRMQLLSCI ALSLALVTNS AANITNLCPF GEVFNATRFA SVYAWNRKRI SNCVADYSVL  60
YNSASFSTFK CYGVSPTKLN DLCFTNVYAD SFVIRGDEVR QIAPGQTGKI ADYNYKLPDD  120
FTGCVIAWNS NNLDSKVGGN YNYLYRLFRK SNLKPFERDI STEIYQAGST PCNGVEGFNC  180
YFPLQSYGFQ PTNGVGYQPY RVVVLSFELL HAPATVCGPK KSTNLVKNK             229

SEQ ID NO: 13           moltype = AA  length = 344
FEATURE                 Location/Qualifiers
REGION                  1..344
                        note = Description of Artificial Sequence: Synthetic
                         polypeptide
source                  1..344
                        mol_type = protein
                        organism = synthetic construct
SEQUENCE: 13
MYRMQLLSCI ALSLALVTNS AANITNLCPF GEVFNATRFA SVYAWNRKRI SNCVADYSVL  60
YNSASFSTFK CYGVSPTKLN DLCFTNVYAD SFVIRGDEVR QIAPGQTGKI ADYNYKLPDD  120
FTGCVIAWNS NNLDSKVGGN YNYLYRLFRK SNLKPFERDI STEIYQAGST PCNGVEGFNC  180
YFPLQSYGFQ PTNGVGYQPY RVVVLSFELL HAPATVCGPK KSTNLVKNKG GGGSGGGGSG  240
GGGSIENADK AIKDFQDNKA PHDKSAAYEA NSKLPKDLRD KNNRFVEKVS IEKAIVRHDE  300
RVKSANDAIS KLNEKDSIEN RRLAQREVNK APMDVKEHLQ KQLD                  344

SEQ ID NO: 14           moltype = AA  length = 327
FEATURE                 Location/Qualifiers
REGION                  1..327
                        note = Description of Artificial Sequence: Synthetic
                         polypeptide
source                  1..327
                        mol_type = protein
                        organism = synthetic construct
SEQUENCE: 14
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNLDSKV GGNYNYLYRL FRKSNLKPFE RDISTEIYQA GSTPCNGVEG FNCYFPLQSY  180
GFQPTNGVGY QPYRVVVLSF ELLHAPATVC GPGGGGSGGG GSGGGGSIEN ADKAIKDFQD  240
NKAPHDKSAA YEANSKLPKD LRDKNNRFVE KVSIEKAIVR HDERVKSAND AISKLNEKDS  300
IENRRLAQRE VNKAPMDVKE HLQKQLD                                     327

SEQ ID NO: 15           moltype = AA  length = 265
FEATURE                 Location/Qualifiers
REGION                  1..265
                        note = Description of Artificial Sequence: Synthetic
                         polypeptide
source                  1..265
                        mol_type = protein
                        organism = synthetic construct
SEQUENCE: 15
```

-continued

```
MYRMQLLSCI ALSLALVTNS AAIAPGQTGK IADYNYKLPD DFTGCVIAWN SNNLDSKVGG  60
NYNYLYRLFR KSNLKPFERD ISTEIYQAGS TPCNGVEGFN CYFPLQSYGF QPTNGVGYQP  120
YRVVVLSFEL LHAPATVCGP KKSTNLVKNK GGGGSGGGGS GGGGSIENAD KAIKDFQDNK  180
APHDKSAAYE ANSKLPKDLR DKNNRFVEKV SIEKAIVRHD ERVKSANDAI SKLNEKDSIE  240
NRRLAQREVN KAPMDVKEHL QKQLD                                      265

SEQ ID NO: 16          moltype = AA  length = 245
FEATURE                Location/Qualifiers
REGION                 1..245
                       note = Description of Artificial Sequence: Synthetic
                        polypeptide
source                 1..245
                       mol_type = protein
                       organism = synthetic construct
SEQUENCE: 16
MYRMQLLSCI ALSLALVTNS AATGCVIAWN SNNLDSKVGG NYNYLYRLFR KSNLKPFERD  60
ISTEIYQAGS TPCNGVEGFN CYFPLQSYGF QPTNGVGYQP YRVVVLSFEL LHAPATVCGP  120
KKSTNLVKNK GGGGSGGGGS GGGGSIENAD KAIKDFQDNK APHDKSAAYE ANSKLPKDLR  180
DKNNRFVEKV SIEKAIVRHD ERVKSANDAI SKLNEKDSIE NRRLAQREVN KAPMDVKEHL  240
QKQLD                                                            245

SEQ ID NO: 17          moltype = AA  length = 237
FEATURE                Location/Qualifiers
REGION                 1..237
                       note = Description of Artificial Sequence: Synthetic
                        polypeptide
source                 1..237
                       mol_type = protein
                       organism = synthetic construct
SEQUENCE: 17
MYRMQLLSCI ALSLALVTNS AASNNLDSKV GGNYNYLYRL FRKSNLKPFE RDISTEIYQA  60
GSTPCNGVEG FNCYFPLQSY GFQPTNGVGY QPYRVVVLSF ELLHAPATVC GPKKSTNLVK  120
NKGGGGSGGG GSGGGGSIEN ADKAIKDFQD NKAPHDKSAA YEANSKLPKD LRDKNNRFVE  180
KVSIEKAIVR HDERVKSAND AISKLNEKDS IENRRLAQRE VNKAPMDVKE HLQKQLD     237

SEQ ID NO: 18          moltype = AA  length = 195
FEATURE                Location/Qualifiers
REGION                 1..195
                       note = Description of Artificial Sequence: Synthetic
                        polypeptide
source                 1..195
                       mol_type = protein
                       organism = synthetic construct
SEQUENCE: 18
MYRMQLLSCI ALSLALVTNS AACNGVEGFN CYFPLQSYGF QPTNGVGYQP YRVVVLSFEL  60
LHAPATVCGP KKSTNLVKNK GGGGSGGGGS GGGGSIENAD KAIKDFQDNK APHDKSAAYE  120
ANSKLPKDLR DKNNRFVEKV SIEKAIVRHD ERVKSANDAI SKLNEKDSIE NRRLAQREVN  180
KAPMDVKEHL QKQLD                                                 195

SEQ ID NO: 19          moltype = AA  length = 272
FEATURE                Location/Qualifiers
REGION                 1..272
                       note = Description of Artificial Sequence: Synthetic
                        polypeptide
source                 1..272
                       mol_type = protein
                       organism = synthetic construct
SEQUENCE: 19
MYRMQLLSCI ALSLALVTNS AATNVYADSF VIRGDEVRQI APGQTGKIAD YNYKLPDDFT  60
GCVIAWNSNN LDSKVGGNYN YLYRLFRKSN LKPFERDIST EIYQAGSTPC NGVEGFNCYF  120
PLQSYGFQPT NGVGYQPYRV VVLSFELKKS TNLVKNKGGG GSGGGGSGGG GSIENADKAI  180
KDFQDNKAPH DKSAAYEANS KLPKDLRDKN NRFVEKVSIE KAIVRHDERV KSANDAISKL  240
NEKDSIENRR LAQREVNKAP MDVKEHLQKQ LD                              272

SEQ ID NO: 20          moltype = AA  length = 197
FEATURE                Location/Qualifiers
REGION                 1..197
                       note = Description of Artificial Sequence: Synthetic
                        polypeptide
source                 1..197
                       mol_type = protein
                       organism = synthetic construct
SEQUENCE: 20
NITNLCPFGE VFNATRFASV YAWNRKRISN CVADYSVLYN SASFSTFKCY GVSPTKLNDL  60
CFTNVYADSF VIRGDEVRQI APGQTGKIAD YNYSLPDDFT GCVIAWNSNN LDSKVGGNYN  120
YLYRLFRKSN LKPFERDIST EIYQAGSTPC NGVEGFNCYF PLQSYGFQPT NGVGYQPYRV  180
VVLSFELLHA PATVCGP                                               197

SEQ ID NO: 21          moltype = AA  length = 197
```

```
FEATURE                 Location/Qualifiers
REGION                  1..197
                        note = Description of Artificial Sequence: Synthetic
                         polypeptide
source                  1..197
                        mol_type = protein
                        organism = synthetic construct
SEQUENCE: 21
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSSN LDSKVGGNYN  120
YLYRLFRKSN LKPFERDIST EIYQAGSTPC NGVEGFNCYF PLQSYGFQPT NGVGYQPYRV  180
VVLSFELLHA PATVCGP                                                197

SEQ ID NO: 22           moltype = AA  length = 197
FEATURE                 Location/Qualifiers
REGION                  1..197
                        note = Description of Artificial Sequence: Synthetic
                         polypeptide
source                  1..197
                        mol_type = protein
                        organism = synthetic construct
SEQUENCE: 22
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSNN TDSKVGGNYN  120
YLYRLFRKSN LKPFERDIST EIYQAGSTPC NGVEGFNCYF PLQSYGFQPT NGVGYQPYRV  180
VVLSFELLHA PATVCGP                                                197

SEQ ID NO: 23           moltype = AA  length = 197
FEATURE                 Location/Qualifiers
REGION                  1..197
                        note = Description of Artificial Sequence: Synthetic
                         polypeptide
source                  1..197
                        mol_type = protein
                        organism = synthetic construct
SEQUENCE: 23
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSNN LSSKVGGNYN  120
YLYRLFRKSN LKPFERDIST EIYQAGSTPC NGVEGFNCYF PLQSYGFQPT NGVGYQPYRV  180
VVLSFELLHA PATVCGP                                                197

SEQ ID NO: 24           moltype = AA  length = 197
FEATURE                 Location/Qualifiers
REGION                  1..197
                        note = Description of Artificial Sequence: Synthetic
                         polypeptide
source                  1..197
                        mol_type = protein
                        organism = synthetic construct
SEQUENCE: 24
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSNN LDSKVGGNYS  120
YLYRLFRKSN LKPFERDIST EIYQAGSTPC NGVEGFNCYF PLQSYGFQPT NGVGYQPYRV  180
VVLSFELLHA PATVCGP                                                197

SEQ ID NO: 25           moltype = AA  length = 197
FEATURE                 Location/Qualifiers
REGION                  1..197
                        note = Description of Artificial Sequence: Synthetic
                         polypeptide
source                  1..197
                        mol_type = protein
                        organism = synthetic construct
SEQUENCE: 25
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSNN LDSKVGGNYN  120
YTYRLFRKSN LKPFERDIST EIYQAGSTPC NGVEGFNCYF PLQSYGFQPT NGVGYQPYRV  180
VVLSFELLHA PATVCGP                                                197

SEQ ID NO: 26           moltype = AA  length = 197
FEATURE                 Location/Qualifiers
REGION                  1..197
                        note = Description of Artificial Sequence: Synthetic
                         polypeptide
source                  1..197
                        mol_type = protein
                        organism = synthetic construct
SEQUENCE: 26
NITNLCPFGE VFNATRFASV YAWNRKRISN CVADYSVLYN SASFSTFKCY GVSPTKLNDL  60
```

-continued

```
CFTNVYADSF VIRGDEVRQI APGQTGKIAD YNYKLPDDFT GCVIAWNSNN LDSKVGGNYN  120
YLYRLFRKSN LSPFERDIST EIYQAGSTPC NGVEGFNCYF PLQSYGFQPT NGVGYQPYRV  180
VVLSFELLHA PATVCGP                                                 197

SEQ ID NO: 27          moltype = AA  length = 197
FEATURE                Location/Qualifiers
REGION                 1..197
                       note = Description of Artificial Sequence: Synthetic
                        polypeptide
source                 1..197
                       mol_type = protein
                       organism = synthetic construct
SEQUENCE: 27
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSNN LDSKVGGNYN  120
YLYRLFRKSN LKPFERDIST EIYQAGSTPC NGTEGFNCYF PLQSYGFQPT NGVGYQPYRV  180
VVLSFELLHA PATVCGP                                                 197

SEQ ID NO: 28          moltype = AA  length = 197
FEATURE                Location/Qualifiers
REGION                 1..197
                       note = Description of Artificial Sequence: Synthetic
                        polypeptide
source                 1..197
                       mol_type = protein
                       organism = synthetic construct
SEQUENCE: 28
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSNN LDSKVGGNYN  120
YLYRLFRKSN LKPFERDIST EIYQAGSTPC NGVEGFNCTF PLQSYGFQPT NGVGYQPYRV  180
VVLSFELLHA PATVCGP                                                 197

SEQ ID NO: 29          moltype = AA  length = 197
FEATURE                Location/Qualifiers
REGION                 1..197
                       note = Description of Artificial Sequence: Synthetic
                        polypeptide
source                 1..197
                       mol_type = protein
                       organism = synthetic construct
SEQUENCE: 29
NITNLCPFGE VFNATRFASV YAWNRKRISN CVADYSVLYN SASFSTFKCY GVSPTKLNDL  60
CFTNVYADSF VIRGDEVRQI APGQTGKIAD YNYKLPDDFT GCVIAWNSNN LDSKVGGNYN  120
YLYRLFRKSN LKPFERDIST EIYQAGSTPC NGVEGFNCYF PLQSYGFQPT NGTGYQPYRV  180
VVLSFELLHA PATVCGP                                                 197

SEQ ID NO: 30          moltype = AA  length = 197
FEATURE                Location/Qualifiers
REGION                 1..197
                       note = Description of Artificial Sequence: Synthetic
                        polypeptide
source                 1..197
                       mol_type = protein
                       organism = synthetic construct
SEQUENCE: 30
NITNLCPFAE VFNATRFASV AAWNAKAISN CVADYSVLYN SASFSTFKCY GVAPTKLNAA  60
CFTNVYADSF VIRGAEVRQI APGQTGKIAD YNYKLPDDFT GCVIAWNSNN LDSKVGGNYN  120
YLYRLFRKSN LKPFERDIST EIYQAGSTPC NGVEGFNCYF PLQSYGFQPT NGVGYQPYRV  180
VVLSFELLAA PATVCGP                                                 197

SEQ ID NO: 31          moltype = AA  length = 197
FEATURE                Location/Qualifiers
REGION                 1..197
                       note = Description of Artificial Sequence: Synthetic
                        polypeptide
source                 1..197
                       mol_type = protein
                       organism = synthetic construct
SEQUENCE: 31
NITNLCAFGE VFNAARFASV YAWNRKRISN CAAAYSAAYN SASFSAFKCA GVAPTKLNDL  60
CFTAVYADAF AIRAAAVRQA APAQAGKIAD YNYKLPDDFT GCVIAWNSNN LDSKVGGNYN  120
YLYRLFRKSN LKPFERDIST EIYQAGSTPC NGVEGFNCYF PLQSYGFQPT NGVGYQPYRV  180
VVLAFELLHA PATACGP                                                 197

SEQ ID NO: 32          moltype = AA  length = 212
FEATURE                Location/Qualifiers
REGION                 1..212
                       note = Description of Artificial Sequence: Synthetic
                        polypeptide
```

```
source                  1..212
                        mol_type = protein
                        organism = synthetic construct
SEQUENCE: 32
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYSL PDDFTGCVIA  120
WNSNNLDSKV GGNYNYLYRL FRKSNLKPFE RDISTEIYQA GSTPCNGVEG FNCYFPLQSY  180
GFQPTNGVGY QPYRVVVLSF ELLHAPATVC GP                                212

SEQ ID NO: 33           moltype = AA  length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 33
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSSNLDSKV GGNYNYLYRL FRKSNLKPFE RDISTEIYQA GSTPCNGVEG FNCYFPLQSY  180
GFQPTNGVGY QPYRVVVLSF ELLHAPATVC GP                                212

SEQ ID NO: 34           moltype = AA  length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 34
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNTDSKV GGNYNYLYRL FRKSNLKPFE RDISTEIYQA GSTPCNGVEG FNCYFPLQSY  180
GFQPTNGVGY QPYRVVVLSF ELLHAPATVC GP                                212

SEQ ID NO: 35           moltype = AA  length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 35
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNLSSKV GGNYNYLYRL FRKSNLKPFE RDISTEIYQA GSTPCNGVEG FNCYFPLQSY  180
GFQPTNGVGY QPYRVVVLSF ELLHAPATVC GP                                212

SEQ ID NO: 36           moltype = AA  length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 36
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNLDSKV GGNYSYLYRL FRKSNLKPFE RDISTEIYQA GSTPCNGVEG FNCYFPLQSY  180
GFQPTNGVGY QPYRVVVLSF ELLHAPATVC GP                                212

SEQ ID NO: 37           moltype = AA  length = 212
FEATURE                 Location/Qualifiers
REGION                  1..212
                        note = Description of Artificial Sequence: Synthetic
                         polypeptide
source                  1..212
                        mol_type = protein
                        organism = synthetic construct
SEQUENCE: 37
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNLDSKV GGNYNYTYRL FRKSNLKPFE RDISTEIYQA GSTPCNGVEG FNCYFPLQSY  180
GFQPTNGVGY QPYRVVVLSF ELLHAPATVC GP                                212
```

-continued

```
SEQ ID NO: 38          moltype = AA  length = 212
FEATURE                Location/Qualifiers
REGION                 1..212
                       note = Description of Artificial Sequence: Synthetic
                        polypeptide
source                 1..212
                       mol_type = protein
                       organism = synthetic construct
SEQUENCE: 38
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNLDSKV GGNYNYLYRL FRKSNLSPFE RDISTEIYQA GSTPCNGVEG FNCYFPLQSY  180
GFQPTNGVGY QPYRVVVLSF ELLHAPATVC GP                                212

SEQ ID NO: 39          moltype = AA  length = 212
FEATURE                Location/Qualifiers
REGION                 1..212
                       note = Description of Artificial Sequence: Synthetic
                        polypeptide
source                 1..212
                       mol_type = protein
                       organism = synthetic construct
SEQUENCE: 39
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNLDSKV GGNYNYLYRL FRKSNLKPFE RDISTEIYQA GSTPCNGTEG FNCYFPLQSY  180
GFQPTNGVGY QPYRVVVLSF ELLHAPATVC GP                                212

SEQ ID NO: 40          moltype = AA  length = 212
FEATURE                Location/Qualifiers
REGION                 1..212
                       note = Description of Artificial Sequence: Synthetic
                        polypeptide
source                 1..212
                       mol_type = protein
                       organism = synthetic construct
SEQUENCE: 40
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNLDSKV GGNYNYLYRL FRKSNLKPFE RDISTEIYQA GSTPCNGVEG FNCTFPLQSY  180
GFQPTNGVGY QPYRVVVLSF ELLHAPATVC GP                                212

SEQ ID NO: 41          moltype = AA  length = 212
FEATURE                Location/Qualifiers
REGION                 1..212
                       note = Description of Artificial Sequence: Synthetic
                        polypeptide
source                 1..212
                       mol_type = protein
                       organism = synthetic construct
SEQUENCE: 41
MFVFLVLLPL VSSAANITNL CPFGEVFNAT RFASVYAWNR KRISNCVADY SVLYNSASFS  60
TFKCYGVSPT KLNDLCFTNV YADSFVIRGD EVRQIAPGQT GKIADYNYKL PDDFTGCVIA  120
WNSNNLDSKV GGNYNYLYRL FRKSNLKPFE RDISTEIYQA GSTPCNGVEG FNCYFPLQSY  180
GFQPTNGTGY QPYRVVVLSF ELLHAPATVC GP                                212

SEQ ID NO: 42          moltype = AA  length = 212
FEATURE                Location/Qualifiers
REGION                 1..212
                       note = Description of Artificial Sequence: Synthetic
                        polypeptide
source                 1..212
                       mol_type = protein
                       organism = synthetic construct
SEQUENCE: 42
MFVFLVLLPL VSSAANITNL CPFAEVFNAT RFASVAAWNA KAISNCVADY SVLYNSASFS  60
TFKCYGVAPT KLNAACFTNV YADSFVIRGA EVRQIAPGQT GKIADYNYKL PDDFTGCVIA  120
WNSNNLDSKV GGNYNYLYRL FRKSNLKPFE RDISTEIYQA GSTPCNGVEG FNCYFPLQSY  180
GFQPTNGVGY QPYRVVVLSF ELLAAPATVC GP                                212

SEQ ID NO: 43          moltype = AA  length = 212
FEATURE                Location/Qualifiers
REGION                 1..212
                       note = Description of Artificial Sequence: Synthetic
                        polypeptide
source                 1..212
                       mol_type = protein
                       organism = synthetic construct
SEQUENCE: 43
```

-continued

```
MFVFLVLLPL VSSAANITNL CAFGEVFNAA RFASVYAWNR KRISNCAAAY SAAYNSASFS  60
AFKCAGVAPT KLNDLCFTAV YADAFAIRAA AVRQAAPAQA GKIADYNYKL PDDFTGCVIA  120
WNSNNLDSKV GGNYNYLYRL FRKSNLKPFE RDISTEIYQA GSTPCNGVEG FNCYFPLQSY  180
GFQPTNGVGY QPYRVVVLAF ELLHAPATAC GP                               212

SEQ ID NO: 44          moltype = AA  length = 210
FEATURE                Location/Qualifiers
REGION                 1..210
                       note = Description of Artificial Sequence: Synthetic
                        polypeptide
source                 1..210
                       mol_type = protein
                       organism = synthetic construct
SEQUENCE: 44
MFVFLVLLPL VSSAAEGVEC DFSPLLSGTP PQVYNFKRLV FTNCNYNLTK LLSLFSVNDF  60
TCSQISPAAI ASNCYSSLIL DSFVIRGDEV RQIAPGQTGK IADYNYKLPD DFTGCVIAWN  120
SNNLDSKVGG NYNYLYRLFR KSNLKPFERD ISTEIYQAGS TPCNGVEGFN CYFPLQSYGF  180
QPTNGVGYQP YRVVVLSFEL LHAPATVCPK                                  210

SEQ ID NO: 45          moltype = AA  length = 210
FEATURE                Location/Qualifiers
REGION                 1..210
                       note = Description of Artificial Sequence: Synthetic
                        polypeptide
source                 1..210
                       mol_type = protein
                       organism = synthetic construct
SEQUENCE: 45
MFVFLVLLPL VSSAAEGVEC DFSPLLSGTP PQVYNFKRLV FTNCNYNLTK LLSLFSVNDF  60
TCSQISPAAI ASNCYSSLIL DYFSYPLSMK SDLSVSSAGP ISQFNYKQSF SNPTCLILAT  120
VPHNLTTITK PLKYSYINKC SRFLSDDRTE VPQLVNANQY TPCNGVEGFN CYFPLQSYGF  180
QPTNGVGYQP YRVVVLSFEL LHAPATVCPK                                  210

SEQ ID NO: 46          moltype = DNA  length = 874
FEATURE                Location/Qualifiers
misc_feature           1..874
                       note = Description of Artificial Sequence: Synthetic
                        polynucleotide
source                 1..874
                       mol_type = other DNA
                       organism = synthetic construct
SEQUENCE: 46
cttgttcttt ttgcagaagc tcagaataaa cgctcaactt tggccaccat gtatcgcatg  60
cagttgctgt cctgtattgc cctgtctctc gcattggtca ctaactctgc cgcaaatatc  120
acaaatctct gccctttcgg ggaggtcttc aacgcaaccc ggttcgcatc agtgtacgcc  180
tggaatcgca aacggatttc taactgtgta gccgattatt ctgtgctgta caacagtgct  240
agtttttcta ccttcaaatg ttatggagta tccccaacca agcttaacga tctttgtttt  300
acaaacgtct acgcagacag ctttgtcatc aggggggacg aagttcgcca aattgctcca  360
gggcagacag gtaaaattgc agactataat tacaaactcc cagacgactt caccggctgt  420
gttatcgctt ggaacagtaa caatcttgac agcaaggtcg gtggcaacta taattatctc  480
tatcgacttt tccgaaaatc caatttgaag ccctttgaga gggacatttc aaccgaaata  540
taccaggctg gatcaactcc ttgcaatggt gtcgaaggat ttaactgtta cttccccttg  600
cagagttacg ggtttcagcc aaccaatggg gtggggtatc aaccataccg ggtcgttgta  660
ttgagtttcg aactgttgca tgctccagca acagtatgtg gtcccaaaaa gagtacaaat  720
ctggtgaaaa acaaataatg atagaccagc ctcaagaaca cccgaatgga gtctctaagc  780
tacataatac caacttacac tttacaaaat gttgtccccc aaaatgtagc cattcgtatc  840
tgctcctaat aaaaagaaag tttcttcaca ttct                             874

SEQ ID NO: 47          moltype = DNA  length = 1219
FEATURE                Location/Qualifiers
misc_feature           1..1219
                       note = Description of Artificial Sequence: Synthetic
                        polynucleotide
source                 1..1219
                       mol_type = other DNA
                       organism = synthetic construct
SEQUENCE: 47
cttgttcttt ttgcagaagc tcagaataaa cgctcaactt tggccaccat gtatcgcatg  60
cagttgctgt cctgtattgc cctgtctctc gcattggtca ctaactctgc cgcaaatatc  120
acaaatctct gccctttcgg ggaggtcttc aacgcaaccc ggttcgcatc agtgtacgcc  180
tggaatcgca aacggatttc taactgtgta gccgattatt ctgtgctgta caacagtgct  240
agtttttcta ccttcaaatg ttatggagta tccccaacca agcttaacga tctttgtttt  300
acaaacgtct acgcagacag ctttgtcatc aggggggacg aagttcgcca aattgctcca  360
gggcagacag gtaaaattgc agactataat tacaaactcc cagacgactt caccggctgt  420
gttatcgctt ggaacagtaa caatcttgac agcaaggtcg gtggcaacta taattatctc  480
tatcgacttt tccgaaaatc caatttgaag ccctttgaga gggacatttc aaccgaaata  540
taccaggctg gatcaactcc ttgcaatggt gtcgaaggat ttaactgtta cttccccttg  600
cagagttacg ggtttcagcc aaccaatggg gtggggtatc aaccataccg ggtcgttgta  660
ttgagtttcg aactgttgca tgctccagca acagtatgtg gtcccaaaaa gagtacaaat  720
```

-continued

```
ctggtgaaaa acaaaggtgg gggtggaagt ggtgggggag gctctggcgg aggaggaagc  780
atagagaacg cagataaggc cataaaggat tttcaggata acaaggcccc ccacgacaag  840
tccgccgcat acgaagcaaa ttccaagttg ccaaaggatt tgcgagacaa aaacaatcgc  900
tttgtagaga aagtttcaat tgaaaaagca attgtaaggc atgacgaacg ggtgaagagt  960
gctaacgatg caataagtaa gctgaacgag aaagactcaa ttgagaaccg aaggttggct  1020
caacgcgagg tcaacaaggc accaatggac gtgaaagagc atctgcaaaa gcaacttgac  1080
taatgataga ccagcctcaa gaacacccga atggagtctc taagctacat aataccaact  1140
tacactttac aaaatgttgt cccccaaaat gtagccattc gtatctgctc ctaataaaaa  1200
gaaagtttct tcacattct                                              1219

SEQ ID NO: 48          moltype = DNA  length = 823
FEATURE                Location/Qualifiers
misc_feature           1..823
                       note = Description of Artificial Sequence: Synthetic
                        polynucleotide
source                 1..823
                       mol_type = other DNA
                       organism = synthetic construct
SEQUENCE: 48
cttgttcttt ttgcagaagc tcagaataaa cgctcaactt tggccaccat gttcgtattt  60
ctggtacttc tccccttgt tagttccgca gcaaatatca ccaatctttg ccctttcgga  120
gaggtattca atgcaactcg gtttgcaagt gtgtacgctt ggaatcgcaa gcgcatcagc  180
aattgcgtcg ctgattacag tgtgctctat aacagtgcat ctttctccac tttcaagtgt  240
tacggtgtta gtccaactaa gctgaacgat ctttgtttta ccaacgtgta cgctgattct  300
ttcgtcattc gaggggatga ggtgcgacaa atagcacctg ggcaaaccgg gaaaatagca  360
gactataatt ataagctccc agatgacttc actgggtgcg taattgcctg gaatagcaac  420
aatcttgaca gtaaagtagg gggaaattac aactatttgt acagattgtt tcgcaaatcc  480
aatttgaagc catttgagcg cgacatctct actgagattt atcaggctgg cagcactcct  540
tgtaacggtg tagaaggctt taactgttat ttccccttc aatcttatgg gtttcagccc  600
accaatggcg tgggatacca gccttatcgc gtcgttgtac ttagttttga actgcttcat  660
gctccagcta cagtgtgcgg cccctaatga tagaccagcc tcaagaacac ccgaatggag  720
tctctaagct acataatacc aacttacact ttacaaaatg ttgtccccca aaatgtagcc  780
attcgtatct gctcctaata aaaagaaagt ttcttcacat tct                  823

SEQ ID NO: 49          moltype = DNA  length = 1168
FEATURE                Location/Qualifiers
misc_feature           1..1168
                       note = Description of Artificial Sequence: Synthetic
                        polynucleotide
source                 1..1168
                       mol_type = other DNA
                       organism = synthetic construct
SEQUENCE: 49
cttgttcttt ttgcagaagc tcagaataaa cgctcaactt tggccaccat gttcgtattt  60
ctggtacttc tccccttgt tagttccgca gcaaatatca ccaatctttg ccctttcgga  120
gaggtattca atgcaactcg gtttgcaagt gtgtacgctt ggaatcgcaa gcgcatcagc  180
aattgcgtcg ctgattacag tgtgctctat aacagtgcat ctttctccac tttcaagtgt  240
tacggtgtta gtccaactaa gctgaacgat ctttgtttta ccaacgtgta cgctgattct  300
ttcgtcattc gaggggatga ggtgcgacaa atagcacctg ggcaaaccgg gaaaatagca  360
gactataatt ataagctccc agatgacttc actgggtgcg taattgcctg gaatagcaac  420
aatcttgaca gtaaagtagg gggaaattac aactatttgt acagattgtt tcgcaaatcc  480
aatttgaagc catttgagcg cgacatctct actgagattt atcaggctgg cagcactcct  540
tgtaacggtg tagaaggctt taactgttat ttccccttc aatcttatgg gtttcagccc  600
accaatggcg tgggatacca gccttatcgc gtcgttgtac ttagttttga actgcttcat  660
gctccagcta cagtgtgcgg ccccggtggg ggtggaagtg gtgggggagg ctctggcgga  720
ggaggaagca tagagaacgc agataaggcc ataaaggatt ttcaggataa caaggccccc  780
cacgacaagt ccgccgcata cgaagcaaat tccaagttgc caaaggattt gcgagacaaa  840
aacaatcgct ttgtagagaa agtttcaatt gaaaaagcaa ttgtaaggca tgacgaacgg  900
gtgaagagtg ctaacgatgc aataagtaag ctgaacgaga aagactcaat tgagaaccga  960
aggttggctc aacgcgaggt caacaaggca ccaatggacg tgaaagagca tctgcaaaag  1020
caacttgact aatgatagac cagcctcaag aacacccgaa tggagtctct aagctacata  1080
ataccaactt acactttaca aaatgttgtc ccccaaaatg tagccattcg tatctgctcc  1140
taataaaaag aaagtttctt cacattct                                    1168

SEQ ID NO: 50          moltype = DNA  length = 982
FEATURE                Location/Qualifiers
misc_feature           1..982
                       note = Description of Artificial Sequence: Synthetic
                        polynucleotide
source                 1..982
                       mol_type = other DNA
                       organism = synthetic construct
SEQUENCE: 50
cttgttcttt ttgcagaagc tcagaataaa cgctcaactt tggccaccat gtatcgcatg  60
cagttgctgt cctgtattgc cctgtctctc gcattggtca ctaactctgc cgcaattgct  120
ccagggcaga caggtaaaat tgcagactat aattacaaac tcccagacga cttcaccggc  180
tgtgttatcg cttggaacag taacaatctt gacagcaagg tcggtggcaa ctataattat  240
ctctatcgac ttttccgaaa atccaatttg aagccctttg agagggacat ttcaaccgaa  300
atataccagg ctggatcaac tccttgcaat ggtgtcgaag gatttaactg ttacttcccc  360
```

```
ttgcagagtt acgggtttca gccaaccaat ggggtggggt atcaaccata ccgggtcgtt  420
gtattgagtt tcgaactgtt gcatgctcca gcaacagtat gtggtcccaa aaagagtaca  480
aatctggtga aaaacaaagg tgggggtgga agtggtgggg gaggctctgg cggaggagga  540
agcatagaga acgcagataa ggccataaag gattttcagg ataacaaggc cccccacgac  600
aagtccgccg catacgaagc aaattccaag ttgccaaagg atttgcgaga caaaaacaat  660
cgctttgtag agaaagtttc aattgaaaaa gcaattgtaa ggcatgacga acgggtgaag  720
agtgctaacg atgcaataag taagctgaac gagaaagact caattgagaa ccgaaggttg  780
gctcaacgcg aggtcaacaa ggcaccaatg gacgtgaaag agcatctgca aaagcaactt  840
gactaatgat agaccagcct caagaacacc cgaatggagt ctctaagcta cataatacca  900
acttacactt tacaaaatgt tgtcccccaa aatgtagcca ttcgtatctg ctcctaataa  960
aaagaaagtt tcttcacatt ct                                            982

SEQ ID NO: 51          moltype = DNA  length = 922
FEATURE                Location/Qualifiers
misc_feature           1..922
                       note = Description of Artificial Sequence: Synthetic
                        polynucleotide
source                 1..922
                       mol_type = other DNA
                       organism = synthetic construct
SEQUENCE: 51
cttgttcttt ttgcagaagc tcagaataaa cgctcaactt tggccaccat gtatcgcatg  60
cagttgctgt cctgtattgc cctgtctctc gcattggtca ctaactctgc cgcaaccggc  120
tgtgttatcg cttggaacag taacaatctt gacagcaagg tcggtggcaa ctataattat  180
ctctatcgac ttttccgaaa atccaatttg aagccctttg agagggacat ttcaaccgaa  240
atataccagg ctggatcaac tccttgcaat ggtgtcgaag gatttaactg ttacttcccc  300
ttgcagagtt acgggtttca gccaaccaat ggggtggggt atcaaccata ccgggtcgtt  360
gtattgagtt tcgaactgtt gcatgctcca gcaacagtat gtggtcccaa aaagagtaca  420
aatctggtga aaaacaaagg tgggggtgga agtggtgggg gaggctctgg cggaggagga  480
agcatagaga acgcagataa ggccataaag gattttcagg ataacaaggc cccccacgac  540
aagtccgccg catacgaagc aaattccaag ttgccaaagg atttgcgaga caaaaacaat  600
cgctttgtag agaaagtttc aattgaaaaa gcaattgtaa ggcatgacga acgggtgaag  660
agtgctaacg atgcaataag taagctgaac gagaaagact caattgagaa ccgaaggttg  720
gctcaacgcg aggtcaacaa ggcaccaatg gacgtgaaag agcatctgca aaagcaactt  780
gactaatgat agaccagcct caagaacacc cgaatggagt ctctaagcta cataatacca  840
acttacactt tacaaaatgt tgtcccccaa aatgtagcca ttcgtatctg ctcctaataa  900
aaagaaagtt tcttcacatt ct                                            922

SEQ ID NO: 52          moltype = DNA  length = 898
FEATURE                Location/Qualifiers
misc_feature           1..898
                       note = Description of Artificial Sequence: Synthetic
                        polynucleotide
source                 1..898
                       mol_type = other DNA
                       organism = synthetic construct
SEQUENCE: 52
cttgttcttt ttgcagaagc tcagaataaa cgctcaactt tggccaccat gtatcgcatg  60
cagttgctgt cctgtattgc cctgtctctc gcattggtca ctaactctgc cgcaagtaac  120
aatcttgaca gcaaggtcgg tggcaactat aattatctct atcgactttt ccgaaaatcc  180
aatttgaagc cctttgagag ggacatttca accgaaatat accaggctgg atcaactcct  240
tgcaatggtg tcgaaggatt taactgttac ttccccttgc agagttacgg gtttcagcca  300
accaatgggg tggggtatca accataccgg gtcgttgtat tgagtttcga actgttgcat  360
gctccagcaa cagtatgtgg tcccaaaaag agtacaaatc tggtgaaaaa caaaggtggg  420
ggtggaagtg gtgggggagg ctctggcgga ggaggaagca tagagaacgc agataaggcc  480
ataaaggatt ttcaggataa caaggccccc cacgacaagt ccgccgcata cgaagcaaat  540
tccaagttgc caaaggattt gcgagacaaa aacaatcgct ttgtagagaa agtttcaatt  600
gaaaaagcaa ttgtaaggca tgacgaacgg gtgaagagtg ctaacgatgc aataagtaag  660
ctgaacgaga aagactcaat tgagaaccga aggttggctc aacgcgaggt caacaaggca  720
ccaatggacg tgaaagagca tctgcaaaag caacttgact aatgatagac cagcctcaag  780
aacacccgaa tggagtctct aagctacata ataccaactt acactttaca aaatgttgtc  840
ccccaaaatg tagccattcg tatctgctcc taataaaaag aaagtttctt cacattct    898

SEQ ID NO: 53          moltype = DNA  length = 772
FEATURE                Location/Qualifiers
misc_feature           1..772
                       note = Description of Artificial Sequence: Synthetic
                        polynucleotide
source                 1..772
                       mol_type = other DNA
                       organism = synthetic construct
SEQUENCE: 53
cttgttcttt ttgcagaagc tcagaataaa cgctcaactt tggccaccat gtatcgcatg  60
cagttgctgt cctgtattgc cctgtctctc gcattggtca ctaactctgc cgcatgcaat  120
ggtgtcgaag gatttaactg ttacttcccc ttgcagagtt acgggtttca gccaaccaat  180
ggggtggggt atcaaccata ccgggtcgtt gtattgagtt tcgaactgtt gcatgctcca  240
gcaacagtat gtggtcccaa aaagagtaca aatctggtga aaaacaaagg tgggggtgga  300
agtggtgggg gaggctctgg cggaggagga agcatagaga acgcagataa ggccataaag  360
gattttcagg ataacaaggc cccccacgac aagtccgccg catacgaagc aaattccaag  420
```

```
ttgccaaagg atttgcgaga caaaaacaat cgctttgtag agaaagtttc aattgaaaaa  480
gcaattgtaa ggcatgacga acgggtgaag agtgctaacg atgcaataag taagctgaac  540
gagaaagact caattgagaa ccgaaggttg gctcaacgcg aggtcaacaa ggcaccaatg  600
gacgtgaaag agcatctgca aaagcaactt gactaatgat agaccagcct caagaacacc  660
cgaatggagt ctctaagcta cataatacca acttacactt tacaaaatgt tgtcccccaa  720
aatgtagcca ttcgtatctg ctcctaataa aaagaaagtt tcttcacatt ct          772

SEQ ID NO: 54          moltype = DNA  length = 973
FEATURE                Location/Qualifiers
misc_feature           1..973
                       note = Description of Artificial Sequence: Synthetic
                        polynucleotide
source                 1..973
                       mol_type = other DNA
                       organism = synthetic construct
SEQUENCE: 54
cttgttcttt ttgcagaagc tcagaataaa cgctcaactt tggccaccat gtatcgcatg  60
cagttgctgt cctgtattgc cctgtctctc gcattggtca ctaactctgc cgcaacaaac  120
gtctacgcag acagctttgt catcaggggg gacgaagttc gccaaattgc tccagggcag  180
acaggtaaaa ttgcagacta taattacaaa ctcccagacg acttcaccgg ctgtgttatc  240
gcttggaaca gtaacaatct tgacagcaag gtcggtggca actataatta tctctatcga  300
cttttccgaa aatccaattt gaagcccttt gagagggaca tttcaaccga aatataccag  360
gctggatcaa ctccttgcaa tggtgtcgaa ggatttaact gttacttccc cttgcagagt  420
tacgggtttc agccaaccaa tggggtgggg tatcaaccat accgggtcgt tgtattgagt  480
ttcgaactgg gtgggggtgg aagtggtggg ggaggctctg gcggaggagg aagcatagag  540
aacgcagata aggccataaa ggattttcag gataacaagg ccccccacga caagtccgcc  600
gcatacgaag caaattccaa gttgccaaag gatttgcgag acaaaaacaa tcgctttgta  660
gagaaagttt caattgaaaa agcaattgta aggcatgacg aacgggtgaa gagtgctaac  720
gatgcaataa gtaagctgaa cgagaaagac tcaattgaga accgaaggtt ggctcaacgc  780
gaggtcaaca aggcaccaat ggacgtgaaa gagcatctgc aaaagcaact tgactaatga  840
tagaccagcc tcaagaacac ccgaatggag tctctaagct acataatacc aacttacact  900
ttacaaaatg ttgtccccca aaatgtagcc attcgtatct gctcctaata aaaagaaagt  960
ttcttcacat tct                                                    973

SEQ ID NO: 55          moltype = DNA  length = 149
FEATURE                Location/Qualifiers
misc_feature           1..149
                       note = Description of Artificial Sequence: Synthetic primer
source                 1..149
                       mol_type = other DNA
                       organism = synthetic construct
SEQUENCE: 55
tttttttttt tttttttttt tttttttttt tttttttttt tttttttttt tttttttttt  60
tttttttttt tttttttttt tttttttttt tttttttttt tttttttttt tttttttttt  120
agaatgtgaa gaaactttct ttttattag                                   149

SEQ ID NO: 56          moltype = DNA  length = 1311
FEATURE                Location/Qualifiers
source                 1..1311
                       mol_type = unassigned DNA
                       organism = Staphylococcus aureus
SEQUENCE: 56
atgaaaaata aatatatctc gaagttgcta gttggggcag caacaattac gttagctaca  60
atgatttcaa atggggaagc aaaagcgagt gaaaacacgc aacaaacttc aactaagcac  120
caaacaactc aaaacaacta cgtaacagat caacaaaaag ctttttatca agtattacat  180
ctaaaaggta tcacagaaga acaacgtaac caatacatca aaacattacg cgaacaccca  240
gaacgtgcac aagaagtatt ctctgaatca cttaaagaca gcaagaaccc agaccgacgt  300
gttgcacaac aaaacgcttt ttacaatgtt cttaaaaatg ataacttaac tgaacaagaa  360
aaaaataatt acattgcaca aattaaagaa aaccctgata gaagccaaca agtttgggta  420
gaatcagtac aatcttctaa agctaaagaa cgtcaaaata ttgaaaatgc ggataaagca  480
attaaagatt tccaagataa caaagcacca cacgataaat cagcagcata tgaagctaac  540
tcaaaattac ctaaagattt acgtgataaa aacaaccgct ttgtagaaaa agtttcaatt  600
gaaaaagcaa tcgttcgtca tgatgagcgt gtgaaatcag caaatgatgc aatctcaaaa  660
ttaaatgaaa aagattcaat tgaaaacaga cgtttagcac aacgtgaagt taacaaagca  720
cctatggatg taaaagagca tttacagaaa caattagacg cattagttgc tcaaaaagat  780
gctgaaaaga aagtggcgcc aaaagttgag gctcctcaaa ttcaatcacc acaaattgaa  840
aaacctaaag tagaatcacc aaaagttgaa gtccctcaaa ttcaatcacc aaaagttgag  900
gttcctcaat ctaaattatt aggttactac caatcattaa aagattcatt taactatggt  960
tacaagtatt taacagatac ttataaaagc tataaagaaa aatatgatac agcaaagtac  1020
tactataata cgtactataa atacaaaggt gcgattgatc aaacagtatt aacagtacta  1080
ggtagtggtt ctaaatctta catccaacca ttgaaagttg atgataaaaa cggctactta  1140
gctaaatcat atgcacaagt aagaaactat gtaactgagt caatcaatac tggtaaagta  1200
ttatatactt tctaccaaaa cccaacatta gtaaaaacag ctattaaagc tcaagaaact  1260
gcatcatcaa tcaaaaatac attaagtaat ttattatcat tctggaaata a          1311

SEQ ID NO: 57          moltype = AA  length = 436
FEATURE                Location/Qualifiers
source                 1..436
                       mol_type = protein
```

-continued

```
                         organism = Staphylococcus aureus
SEQUENCE: 57
MKNKYISKLL VGAATITLAT MISNGEAKAS ENTQQTSTKH QTTQNNYVTD QQKAFYQVLH  60
LKGITEEQRN QYIKTLREHP ERAQEVFSES LKDSKNPDRR VAQQNAFYNV LKNDNLTEQE  120
KNNYIAQIKE NPDRSQQVWV ESVQSSKAKE RQNIENADKA IKDFQDNKAP HDKSAAYEAN  180
SKLPKDLRDK NNRFVEKVSI EKAIVRHDER VKSANDAISK LNEKDSIENR RLAQREVNKA  240
PMDVKEHLQK QLDALVAQKD AEKKVAPKVE APQIQSPQIE KPKVESPKVE VPQIQSPKVE  300
VPQSKLLGYY QSLKDSFNYG YKYLTDTYKS YKEKYDTAKY YYNTYYKYKG AIDQTVLTVL  360
GSGSKSYIQP LKVDDKNGYL AKSYAQVRNY VTESINTGKV LYTFYQNPTL VKTAIKAQET  420
ASSIKNTLSN LLSFWK                                                436

SEQ ID NO: 58            moltype = AA  length = 1273
FEATURE                  Location/Qualifiers
source                   1..1273
                         mol_type = protein
                         organism = Severe acute respiratory syndrome coronavirus 2
SEQUENCE: 58
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                   1273

SEQ ID NO: 59            moltype = DNA  length = 3822
FEATURE                  Location/Qualifiers
source                   1..3822
                         mol_type = unassigned DNA
                         organism = Severe acute respiratory syndrome coronavirus 2
SEQUENCE: 59
atgtttgttt ttcttgtttt attgccacta gtctctagtc agtgtgttaa tcttacaacc  60
agaactcaat taccccctgc atacactaat tctttcacac gtggtgttta ttaccctgac  120
aaagttttca gatcctcagt tttacattca actcaggact tgttcttacc tttcttttcc  180
aatgttactt ggttccatgc tatacatgtc tctgggacca atggtactaa gaggtttgat  240
aaccctgtcc taccatttaa tgatggtgtt tattttgctt ccactgagaa gtctaacata  300
ataagaggct ggatttttgg tactacttta gattcgaaga cccagtccct acttattgtt  360
aataacgcta ctaatgttgt tattaaagtc tgtgaatttc aattttgtaa tgatccattt  420
ttgggtgttt attaccacaa aaacaacaaa agttggatgg aaagtgagtt cagagtttat  480
tctagtgcga ataattgcac ttttgaatat gtctctcagc cttttcttat ggaccttgaa  540
ggaaaacagg gtaatttcaa aaatcttagg gaatttgtgt ttaagaatat tgatggttat  600
tttaaaatat attctaagca cacgcctatt aatttagtgc gtgatctccc tcagggtttt  660
tcggctttag aaccattggt agatttgcca ataggtatta acatcactag gtttcaaact  720
ttacttgctt tacatagaag ttatttgact cctggtgatt cttcttcagg ttggacagct  780
ggtgctgcag cttattatgt gggttatctt caacctagga cttttctatt aaaatataat  840
gaaaatggaa ccattacaga tgctgtagac tgtgcacttg accctctctc agaaacaaag  900
tgtacgttga aatccttcac tgtagaaaaa ggaatctatc aaacttctaa ctttagagtc  960
caaccaacag aatctattgt tagatttcct aatattacaa acttgtgccc ttttggtgaa  1020
gtttttaacg ccaccagatt tgcatctgtt tatgcttgga acaggaagag aatcagcaac  1080
tgtgttgctg attattctgt cctatataat tccgcatcat tttccacttt taagtgttat  1140
ggagtgtctc ctactaaatt aaatgatctc tgctttacta atgtctatgc agattcattt  1200
gtaattagag gtgatgaagt cagacaaatc gctccagggc aaactggaaa gattgctgat  1260
tataattata aattaccaga tgattttaca ggctgcgtta tagcttggaa ttctaacaat  1320
cttgattcta aggttggtgg taattataat tacctgtata gattgtttag gaagtctaat  1380
ctcaaacctt ttgagagaga tatttcaact gaaatctatc aggccggtag cacaccttgt  1440
aatggtgttg aaggttttaa ttgttacttt cctttacaat catatggttt ccaacccact  1500
aatggtgttg gttaccaacc atacagagta gtagtacttt cttttgaact tctacatgca  1560
ccagcaactg tttgtggacc taaaaagtct actaatttgg ttaaaaacaa atgtgtcaat  1620
ttcaacttca atggtttaac aggcacaggt gttcttactg agtctaacaa aaagtttctg  1680
cctttccaac aatttggcag agacattgct gacactactg atgctgtccg tgatccacag  1740
acacttgaga ttcttgacat tacaccatgt tcttttggtg gtgtcagtgt tataacacca  1800
ggaacaaata cttctaacca ggttgctgtt ctttatcagg atgttaactg cacagaagtc  1860
cctgttgcta ttcatgcaga tcaacttact cctacttggc gtgtttattc tacaggttct  1920
aatgtttttc aaacacgtgc aggctgttta ataggggctg aacatgtcaa caactcatat  1980
```

-continued

```
gagtgtgaca tacccattgg tgcaggtata tgcgctagtt atcagactca gactaattct  2040
cctcggcggg cacgtagtgt agctagtcaa tccatcattg cctacactat gtcacttggt  2100
gcagaaaatt cagttgctta ctctaataac tctattgcca tacccacaaa ttttactatt  2160
agtgttacca cagaaattct accagtgtct atgaccaaga catcagtaga ttgtacaatg  2220
tacatttgtg gtgattcaac tgaatgcagc aatcttttgt tgcaatatgg cagtttttgt  2280
acacaattaa accgtgcttt aactggaata gctgttgaac aagacaaaaa cacccaagaa  2340
gtttttgcac aagtcaaaca aatttacaaa acaccaccaa ttaaagattt tggtggtttt  2400
aatttttcac aaatattacc agatccatca aaaccaagca agaggtcatt tattgaagat  2460
ctacttttca acaaagtgac acttgcagat gctggcttca tcaaacaata tggtgattgc  2520
cttggtgata ttgctgctag agacctcatt tgtgcacaaa agtttaacgg ccttactgtt  2580
ttgccacctt tgctcacaga tgaaatgatt gctcaataca cttctgcact gttagcgggt  2640
acaatcactt ctggttggac ctttggtgca ggtgctgcat tacaaatacc atttgctatg  2700
caaatggctt ataggtttaa tggtattgga gttacacaga atgttctcta tgagaaccaa  2760
aaattgattg ccaaccaatt taatagtgct attggcaaaa ttcaagactc actttcttcc  2820
acagcaagtg cacttggaaa acttcaagat gtggtcaacc aaaatgcaca agctttaaac  2880
acgcttgtta aacaacttag ctccaatttt ggtgcaattt caagtgtttt aaatgatatc  2940
ctttcacgtc ttgacaaagt tgaggctgaa gtgcaaattg ataggttgat cacaggcaga  3000
cttcaaagtt tgcagacata tgtgactcaa caattaatta gagctgcaga aatcagagct  3060
tctgctaatc ttgctgctac taaaatgtca gagtgtgtac ttggacaatc aaaaagagtt  3120
gatttttgtg gaaagggcta tcatcttatg tccttccctc agtcagcacc tcatggtgta  3180
gtcttcttgc atgtgactta tgtccctgca caagaaaaga acttcacaac tgctcctgcc  3240
atttgtcatg atggaaaagc acactttcct cgtgaaggtg tctttgtttc aaatggcaca  3300
cactggtttg taacacaaag gaatttttat gaaccacaaa tcattactac agacaacaca  3360
tttgtgtctg gtaactgtga tgttgtaata ggaattgtca acaacacagt ttatgatcct  3420
ttgcaacctg aattagactc attcaaggag gagttagata aatattttaa gaatcataca  3480
tcaccagatg ttgatttagg tgacatctct ggcattaatg cttcagttgt aaacattcaa  3540
aaagaaattg accgcctcaa tgaggttgcc aagaatttaa atgaatctct catcgatctc  3600
caagaacttg gaaagtatga gcagtatata aaatggccat ggtacatttg gctaggtttt  3660
atagctggct tgattgccat agtaatggtg acaattatgc tttgctgtat gaccagttgc  3720
tgtagttgtc tcaagggctg ttgttcttgt ggatcctgct gcaaatttga tgaagacgac  3780
tctgagccag tgctcaaagg agtcaaatta cattacacat aa                    3822

SEQ ID NO: 60          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 60
GGGGS                                                             5

SEQ ID NO: 61          moltype = AA  length = 50
FEATURE                Location/Qualifiers
REGION                 1..50
                       note = Description of Artificial Sequence: Synthetic
                        polypeptide
VARIANT                1..50
                       note = SITE - This sequence may encompass 1-10 GGGGS
                        repeating units
source                 1..50
                       mol_type = protein
                       organism = synthetic construct
SEQUENCE: 61
GGGGSGGGGS GGGGSGGGGS GGGGSGGGGS GGGGSGGGGS GGGGSGGGGS            50

SEQ ID NO: 62          moltype = DNA  length = 45
FEATURE                Location/Qualifiers
misc_feature           1..45
                       note = Description of Artificial Sequence: Synthetic primer
source                 1..45
                       mol_type = other DNA
                       organism = synthetic construct
SEQUENCE: 62
gaatttaata cgactcacta taaggcttgt tctttttgca gaagc                 45

SEQ ID NO: 63          moltype = AA  length = 59
FEATURE                Location/Qualifiers
source                 1..59
                       mol_type = protein
                       organism = Influenza A virus
SEQUENCE: 63
IVETPNPENG TCYPGYFADY EELREQLSSV SSFERFEIFP KESSWPNHTV TGVSASCSH   59

SEQ ID NO: 64          moltype = AA  length = 60
FEATURE                Location/Qualifiers
source                 1..60
                       mol_type = protein
                       organism = Influenza A virus
```

```
SEQUENCE: 64
IAETPNSENG ACYPGDFADY EELREQLSSV SSFERFEIFP KERSWPKHNI TRGVTAACSH  60

SEQ ID NO: 65           moltype = AA  length = 60
FEATURE                 Location/Qualifiers
source                  1..60
                        mol_type = protein
                        organism = Influenza A virus
SEQUENCE: 65
IAETPNSENG TCYPGYFADY EELREQLSSV SSFERFEIFP KERSWPKHNV TRGVTASCSH  60

SEQ ID NO: 66           moltype = AA  length = 59
FEATURE                 Location/Qualifiers
source                  1..59
                        mol_type = protein
                        organism = Influenza A virus
SEQUENCE: 66
IVETPNSENG ACYPGDFIDY EELREQLSSV SSLERFEIFP KESSWPNHTF NGVTVSCSH   59

SEQ ID NO: 67           moltype = AA  length = 60
FEATURE                 Location/Qualifiers
source                  1..60
                        mol_type = protein
                        organism = Influenza A virus
SEQUENCE: 67
IVETSNSENG TCYPGDFIDY EELREQLSSV SSFEKFEIFP KTSSWPNHET TKGVTAACSY  60

SEQ ID NO: 68           moltype = AA  length = 60
FEATURE                 Location/Qualifiers
source                  1..60
                        mol_type = protein
                        organism = Influenza A virus
SEQUENCE: 68
IVETPSSDNG TCYPGDFIDY EELREQLSSV SSFERFEIFP KTSSWPNHDS NKGVTAACPH  60

SEQ ID NO: 69           moltype = AA  length = 60
FEATURE                 Location/Qualifiers
source                  1..60
                        mol_type = protein
                        organism = Influenza A virus
SEQUENCE: 69
NGKSSFYRNL LWLTKKNGLY PNLSKSYVNN KEKEVLVLWG VHHPSNIGDQ RTIYHTENAY  60

SEQ ID NO: 70           moltype = AA  length = 60
FEATURE                 Location/Qualifiers
source                  1..60
                        mol_type = protein
                        organism = Influenza A virus
SEQUENCE: 70
AGKSSFYKNL LWLTETDGSY PKLSKSYVNN KEKEVLVLWG VHHPSNIEDQ KTLYRKENAY  60

SEQ ID NO: 71           moltype = AA  length = 60
FEATURE                 Location/Qualifiers
source                  1..60
                        mol_type = protein
                        organism = Influenza A virus
SEQUENCE: 71
KGKSSFYRNL LWLTEKNGSY PNLSKSYVNN KEKEVLVLWG VHHPSNIEDQ KTIYRKENAY  60

SEQ ID NO: 72           moltype = AA  length = 60
FEATURE                 Location/Qualifiers
source                  1..60
                        mol_type = protein
                        organism = Influenza A virus
SEQUENCE: 72
RGKSSFYRNL LWLTKKGDSY PKLTNSYVNN KGKEVLVLWG VHHPSSSDEQ QSLYSNGNAY  60

SEQ ID NO: 73           moltype = AA  length = 60
FEATURE                 Location/Qualifiers
source                  1..60
                        mol_type = protein
                        organism = Influenza A virus
```

-continued

```
SEQUENCE: 73
AGASSFYRNL LWLTKKGSSY PKLSKSYVNN KGKEVLVLWG VHHPPTGTDQ QSLYQNADAY  60

SEQ ID NO: 74          moltype = AA  length = 60
FEATURE                Location/Qualifiers
source                 1..60
                       mol_type = protein
                       organism = Influenza A virus
SEQUENCE: 74
AGAKSFYKNL IWLVKKGNSY PKLSKSYIND KGKEVLVLWG IHHPSTSADQ QSLYQNADTY  60
```

COMPOSITIONS INCLUDING SBI ADJUVANTS AND METHODS OF USE THEREOF

CROSS-REFERENCE TO RELATED APPLICATIONS

This application is a Divisional of U.S. application Ser. No. 17/685,717 filed on Mar. 3, 2022, now issued as U.S. Pat. No. 11,771,758, which claims priority to U.S. Provisional Patent Application 63/156,860 filed on Mar. 4, 2021, the entire contents of each of which is hereby incorporated by reference.

SEQUENCE LISTING

The instant application contains a Sequence Listing which has been submitted electronically in XML format and is hereby incorporated by reference in its entirety. Said XML copy, created on Nov. 14, 2023, and named 2012611-0078 SL.xml is 109,902 bytes in size.

BACKGROUND

In recent years, progress has been made in the development of vaccines for a variety of diseases and conditions. However, these efforts have not been able to generate broadly neutralizing vaccines.

SUMMARY

The present disclosure provides compositions for stimulating an immune response against an antigen and/or for enhancing immunogenicity of an antigen. In some embodiments, compositions disclosed herein comprise immunogenic compositions comprising: (1) an antigen fragment or an antigen variant, fused to (2) an adjuvant comprising a complement C3d-binding region. In some embodiments, an immunogenic composition disclosed herein can enhance the titers of the resulting antibody response and/or result in a measurable T cell response. In some embodiments, the adjuvant is or comprises a complement C3d-binding region of a Sbi protein from *Staphylococcus aureus* (e.g., Sbi III and/or Sbi IV). Also provided herein are pharmaceutical compositions and methods of using said pharmaceutical compositions to stimulate an immune response against an antigen and/or to enhance immunogenicity of an antigen.

The present disclosure provides a polypeptide comprising a complement C3d-binding polypeptide from an immunoglobulin-binding protein (Sbi) of *Staphylococcus aureus*. In some embodiments, a polypeptide is a fusion polypeptide comprising: (i) a fragment antigen that comprises an epitope of a target protein antigen; and (ii) a complement C3d-binding polypeptide from an immunoglobulin-binding protein (Sbi) of *Staphylococcus aureus*.

In some embodiments, a complement C3d-binding polypeptide is or comprises one or both of domain III and domain IV of the Sbi of *Staphylococcus aureus*, or a functional fragment or a variant thereof. In some embodiments, a complement C3d-binding polypeptide is or comprises domain III of the Sbi of *Staphylococcus aureus*, or a functional fragment or a variant thereof. In some embodiments, a complement C3d-binding polypeptide is or comprises domain IV of the Sbi of *Staphylococcus aureus*, or a functional fragment or a variant thereof. In some embodiments, a complement C3d-binding polypeptide is or comprises domain III and domain IV of the Sbi of *Staphylococcus aureus*, or a functional fragment or a variant thereof.

In some embodiments, a fragment antigen has an amino acid sequence length of at least 5%, 10%, 20%, 30%, 40%, 50%, 60%, 70%, 80%, 90% or 95% compared to the amino acid sequence length of the target protein antigen. In some embodiments, a fragment antigen has an amino acid sequence length of no more than 50% of the amino acid sequence length of the target protein antigen. In some embodiments, a fragment antigen has an amino acid sequence length of no more than 40%, 30%, 20%, 10% or 5% of the amino acid sequence length of the target protein antigen.

In some embodiments, a fragment antigen has about 10-300 amino acid residues in length. In some embodiments, a fragment antigen has at least 10 amino acid residues in length. In some embodiments, a fragment antigen has less than about 300 amino acid residues in length. In some embodiments, a fragment antigen has about 10-300, 10-250, 10-200, 10-150, 10-100, 10-90, 10-80, 10-70, 10-60, 10-50, 10-40, 10-30, 10-20, 20-300, 30-300, 40-300, 50-300, 60-300, 70-300, 80-300, 90-100, 100-300, 150-300, 200-300, 250-300, 20-250, 30-200, 40-150, 50-100, 60-90, or 70-80 amino acids residues in length. In some embodiments, a fragment antigen has about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 amino acids residues in length.

Also provided herein is a fusion polypeptide comprising: (i) an antigen variant or a fragment antigen variant that comprises an epitope of a target protein antigen; and (ii) a complement C3d-binding polypeptide from an immunoglobulin-binding protein (Sbi) of *Staphylococcus aureus*.

In some embodiments, a complement C3d-binding polypeptide is or comprises one or both of domain III and domain IV of the Sbi of *Staphylococcus aureus*, or a functional fragment or a variant thereof. In some embodiments, a complement C3d-binding polypeptide is or comprises domain III of the Sbi of *Staphylococcus aureus*, or a functional fragment or a variant thereof. In some embodiments, a complement C3d-binding polypeptide is or comprises domain IV of the Sbi of *Staphylococcus aureus*, or a functional fragment or a variant thereof. In some embodiments, a complement C3d-binding polypeptide is or comprises domain III and domain IV of the Sbi of *Staphylococcus aureus*, or a functional fragment or a variant thereof.

In some embodiments, an antigen variant or fragment antigen variant amino acid sequence length is identical to the amino acid sequence length of the target protein antigen.

In some embodiments, an antigen variant or fragment antigen variant comprises at least one modified amino acid compared to the target protein antigen. In some embodiments, a modified amino acid comprises N-linked glycosylation. In some embodiments, an antigen variant or fragment antigen variant comprises at least one amino acid mutation compared to the target protein antigen. In some embodiments, an antigen variant or fragment antigen variant comprises 2, 3, 4, 5, 6, 7, 8, 9, 10, 15, 20, 30, 40 or 50 amino acid mutations compared to the target protein antigen. In some embodiments, the mutation introduces a Serine, a Threonine, an Alanine, or an amino acid at a particular position which is different from the amino acid present at that position in the target protein antigen. In some embodiments, the mutation prevents formation of a disulfide bond.

In some embodiments, a fragment antigen is characterized in that when expressed in vivo, it binds to a Major Histocompatibility Complex (MHC) molecule. In some embodiments, a MHC molecule is or comprises a MHC I molecule or a MHC II molecule.

In some embodiments, a fragment antigen is characterized in that when expressed in vivo, it does not bind to a MHC molecule.

In some embodiments, a fragment antigen is characterized in that when expressed in vivo, it folds into a three-dimensional conformation that is substantially identical to the three-dimensional conformation of the fragment antigen as it is in its native position in the target protein antigen.

In some embodiments, a fragment antigen, antigen variant or fragment antigen variant further comprises an amino acid sequence from a second target protein antigen.

In some embodiments, a target protein antigen is or comprises an infectious disease antigen. In some embodiments, an infectious disease antigen is or comprises a viral antigen, a bacterial antigen, a fungal antigen, or combinations thereof. In some embodiments, a viral antigen is or comprises an influenza antigen. In some embodiments, a viral antigen is or comprises a coronavirus polypeptide. In some embodiments, a coronavirus polypeptide is or comprises a SARS-CoV-2 protein. In some embodiments, a SARS-CoV-2 protein is or comprises a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof an accessory factor polypeptide or fragment thereof; or any combination thereof. In some embodiments, a SARS-CoV-2 protein comprises a Spike protein or a fragment thereof (e.g., RBD).

In some embodiments, a target protein antigen is or comprises a cancer antigen.

In some embodiments, a fragment antigen, antigen variant or fragment antigen variant has an amino acid sequence at least 80%, 85%, 90%, 91%, 92%, 93%, 94%, 95%, 96%, 97%, 98%, 99% or 100% identity to the amino acid sequence of SEQ ID NO: 3.

In some embodiments, a fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 4.

In some embodiments, a fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 5.

In some embodiments, a fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 6.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 7.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 20.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 21.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 22.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 23.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 24.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 25.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO:26.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 27.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 28.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 29.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 30.

In some embodiments, a fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 31.

In some embodiments, a fragment antigen, antigen variant or fragment antigen variant has at least 80%, 85%, 90%, or 100% identity to the amino acid sequence of SEQ ID NO: 8.

In some embodiments, a complement C3d-binding polypeptide comprises an Sbi domain III having at least 80%, 85%, 90%, 91%, 92%, 93%, 94%, 95%, 96%, 97%, or 100% identity to the amino acid sequence of SEQ ID NO: 9.

In some embodiments, a complement C3d-binding polypeptide comprises an Sbi domain IV having at least 80%, 85%, 90%, 91%, 92%, 93%, 94%, 95%, 96%, 97%, or 100% identity to the amino acid sequence of SEQ ID NO: 10.

In some embodiments, a Sbi domain III and a Sbi domain IV are contiguous.

In some embodiments, a Sbi domain III and a Sbi domain IV are separated by a linker.

In some embodiments, (a) and (b) are encoded by a nucleotide sequence and are disposed in the same nucleotide sequence or in different nucleotide sequences. In some embodiments, (a) is disposed N-terminus of (b). In some embodiments, (a) is disposed C-terminus of (b).

In some embodiments, (a) and (b) are contiguous or separated by a linker. In some embodiments, the linker is a peptidyl linker. In some embodiments, the peptidyl linker comprises at least 60% glycine and/or serine. In some embodiments, the linker is chosen from a Gly-Gly-Gly-Gly-Ser (Gly4-Ser) linker (SEQ ID NO: 60), or a Histidine linker. In some embodiments, the linker is a Gly4-Ser linker (SEQ ID NO: 60). In some embodiments, the linker comprises 1, 2, 3, 4, 5, 6, 7, 8, 9, or 10 repeats of the Gly4-Ser linker (SEQ ID NO: 61). In some embodiments, the linker comprises 3 repeats of the Gly4-Ser linker (SEQ ID NO: 11). In some embodiments, the linker comprises the sequence of SEQ ID NO: 11.

In some embodiments, a fusion polypeptide further comprises a secretion peptide. In some embodiments, the secretion peptide is about 10-30 amino acids in length. In some embodiments, a secretion peptide is about 10, 11, 12, 13, 14, 15, 16, 17, 18, 19, 20, 21, 22, 23, 24, 25, 26, 27, 28, 29 or 30 amino acids in length. In some embodiments, a secretion peptide comprises an amino acid having at least 80%, 85%, 90%, or 100% identity to the amino acid sequence of SEQ ID NO: 1. In some embodiments, a secretion peptide comprises an amino acid having at least 80%, 85%, 90%, or 100% identity to the amino acid sequence of SEQ ID NO: 2.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 12.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 13.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 14.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 15.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 16.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 17.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 18.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 19.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 32.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 33.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 34.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:35.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:36.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:37.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:38.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:39.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:40.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:41.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:42.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 43.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO: 44.

In some embodiments, a fusion polypeptide has at least 80%, 85%, 90%, 91%, 92%, 93%, 94%, 95%, 96%, 97%, 98%, 99% or 100% identity to the amino acid sequence of SEQ ID NO:45.

In some embodiments, a fusion polypeptide is encoded by a polynucleotide which is or comprises RNA. In some embodiments, a fusion polynucleotide is or comprises messenger RNA.

In some embodiments, a fusion polypeptide is encoded by a polynucleotide which is or comprises DNA.

Disclosed herein is a fusion polynucleotide encoding any one of the fusion polypeptides disclosed herein.

Also disclosed herein is a fusion polynucleotide comprising a nucleotide sequence encoding: (i) a fragment antigen that comprises an epitope of a target protein antigen; and (ii) a complement C3d-binding polypeptide from an immunoglobulin-binding protein (Sbi) of *Staphylococcus aureus.*

Disclosed herein is a polynucleotide comprising a nucleotide sequence encoding: (i) an antigen variant or a fragment antigen variant that comprises an epitope of a target protein antigen; and (ii) a complement C3d-binding polypeptide from an immunoglobulin-binding protein (Sbi) of *Staphylococcus aureus.*

In some embodiments, a fusion polynucleotide is or comprises RNA. In some embodiments, a polynucleotide is or comprises messenger RNA.

In some embodiments, a fusion polynucleotide is or comprises DNA.

In some embodiments, a complement C3d-binding polypeptide encoded by the polynucleotide is or comprises one or both of domain III and domain IV of the Sbi of *Staphylococcus aureus*, or a functional fragment or a variant thereof. In some embodiments, a complement C3d-binding polypeptide encoded by the polynucleotide is or comprises domain III of the Sbi of *Staphylococcus aureus*, or a functional fragment or a variant thereof. In some embodiments, a complement C3d-binding polypeptide encoded by the polynucleotide is or comprises domain IV of the Sbi of *Staphylococcus aureus*, or a functional fragment or a variant thereof. In some embodiments, a complement C3d-binding polypeptide encoded by the polynucleotide is or comprises domain III and domain IV of the Sbi of *Staphylococcus aureus*, or a functional fragment or a variant thereof.

In some embodiments, a fusion polynucleotide encodes a fragment antigen that has an amino acid sequence length of at least 5%, 10%, 20%, 30%, 40%, 50%, 60%, 70%, 80%, 90% or 95% compared to the amino acid sequence length of the target protein antigen. In some embodiments, a fusion polynucleotide encodes a fragment antigen that has an amino acid sequence length of no more than 50% of the amino acid sequence length of the target protein antigen. In some embodiments, a fusion polynucleotide encodes a fragment antigen has an amino acid sequence length of no more than 40%, 30%, 20%, 10% or 5% of the amino acid sequence length of the target protein antigen.

In some embodiments, a fusion polynucleotide encodes an antigen variant or fragment antigen variant having an amino acid sequence length that is identical to the amino acid sequence length of the target protein antigen.

In some embodiments, a fusion polynucleotide encodes an antigen variant or fragment antigen variant which comprises at least one modified amino acid compared to the target protein antigen.

In some embodiments, a fusion polynucleotide encodes a fragment antigen which is characterized in that when expressed in vivo, it binds to a Major Histocompatibility Complex (MHC) molecule. In some embodiments, a MHC molecule is or comprises a MHC I molecule or a MHC II molecule.

In some embodiments, a fusion polynucleotide encodes a fragment antigen which is characterized in that when expressed in vivo, it does not bind to a MHC molecule.

In some embodiments, a fusion polynucleotide encodes a fragment antigen which is characterized in that when expressed in vivo, it folds into a three-dimensional conformation that is substantially identical to the three-dimensional conformation of the fragment antigen as it is in its native position in the target protein antigen.

In some embodiments, a fusion polynucleotide encodes a fragment antigen, antigen variant or fragment antigen variant which further comprises an amino acid sequence from a second target protein antigen.

In some embodiments, a target protein antigen is or comprises an infectious disease antigen. In some embodiments, an infectious disease antigen is or comprises a viral antigen, a bacterial antigen, a fungal antigen, or combinations thereof. In some embodiments, an antigen is or comprises a viral antigen. In some embodiments, a viral antigen is or comprises an influenza antigen. In some embodiments, a viral antigen is or comprises a coronavirus polypeptide. In some embodiments, a coronavirus polypeptide is or comprises a SARS-CoV-2 protein. In some embodiments, a SARS-CoV-2 protein is or comprises a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof an accessory factor polypeptide or fragment thereof; or any combination thereof. In some embodiments, the SARS-CoV-2 protein comprises a Spike protein or a fragment thereof (e.g., RBD).

In some embodiments, a target protein antigen is or comprises a cancer antigen.

In some embodiments, (a) is disposed C-terminus of (b). In some embodiments, (a) and (b) are contiguous or separated by a nucleotide sequence encoding a linker. In some embodiments, the linker is a peptidyl linker. In some embodiments, the peptidyl linker comprises at least 60% glycine and/or serine. In some embodiments, the linker is chosen from a Gly-Gly-Gly-Gly-Ser (Gly4-Ser) linker (SEQ ID NO: 60), or a Histidine linker.

In some embodiments, a fusion polynucleotide further comprises a nucleotide sequence encoding a secretion peptide.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 46.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 47.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 48.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 49.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 50.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 51.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 52.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 53.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 54.

Disclosed herein is an expression vector comprising any one of the fusion polynucleotides disclosed herein.

In some embodiments, an expression vector comprises a viral vector. In some embodiments, a viral vector comprises a retrovirus vector, an adenovirus vector, an adeno-associated virus vector or a lentivirus vector or an RNA vector.

Also disclosed herein is a composition for delivering any one of the fusion polypeptides disclosed herein.

Disclosed herein is a composition for delivering any one of the fusion polynucleotides disclosed herein.

This disclosure provides a pharmaceutical composition that delivers a fusion polypeptide disclosed herein, a fusion polynucleotide disclosed herein, or an expression vector comprising a fusion polynucleotide disclosed herein.

In some embodiments, a pharmaceutical composition further comprises a pharmaceutically acceptable excipient, a diluent, or a combination thereof.

Disclosed herein is a method of making comprising: recombinantly joining a first nucleotide sequence that encodes a fragment antigen comprising an epitope of a target protein antigen, and a second nucleotide sequence that encodes a complement C3d-binding polypeptide from a immunoglobulin-binding protein (Sbi) of *Staphylococcus aureus* to form a polynucleotide comprising the first nucleotide sequence and the second nucleotide sequence.

In some embodiments, the method further comprises expressing the polynucleotide in a cell to produce a fusion polypeptide encoded by the polynucleotide.

Disclosed herein is a cell comprising a fusion polypeptide disclosed herein, a fusion polynucleotide disclosed herein, or an expression vector comprising a fusion polynucleotide disclosed herein.

In some embodiments, the cell is contacted with the fusion polynucleotide, fusion polypeptide or expression vector. In some embodiments, contacting occurs in vivo, in vitro or ex vivo.

Disclosed herein is a kit comprising a fusion polypeptide disclosed herein, a fusion polynucleotide disclosed herein, or an expression vector comprising a fusion polynucleotide disclosed herein, and instructions for use.

In some embodiments, the kit further comprises: a polynucleotide comprising a nucleotide sequence that encodes a target protein antigen; or a target protein antigen encoded by the polynucleotide.

The disclosure provides, a method comprising administering to a subject in need thereof at least one dose of a pharmaceutical composition comprising a fusion polypeptide disclosed herein, a fusion polynucleotide disclosed herein, or an expression vector comprising a fusion polynucleotide disclosed herein.

In some embodiments, the at least one dose is administered in an effective amount to induce an immune response against the fragment antigen in the subject.

In some embodiments, the immune response comprises generation of a neutralizing antibody titer against the fragment antigen.

In some embodiments, a neutralizing antibody titer is increased by at least 50%, as compared to a neutralizing antibody titer induced by a fragment antigen in the absence of the complement C3d-binding polypeptide from an immunoglobulin-binding protein (Sbi) of *Staphylococcus aureus*.

In some embodiments, the generation of a neutralizing antibody titer has been established in a mouse model using a dose of at least 0.1 μg.

In some embodiments, the at least one dose is administered in an effective amount to stimulate B cells while reducing induction of T cell response.

Disclosed herein is a method comprising administering to a subject: a first dose of a pharmaceutical composition disclosed herein; and a second dose of a pharmaceutical composition disclosed herein. In some embodiments, a pharmaceutical composition comprises a fusion polypeptide disclosed herein, a fusion polynucleotide disclosed herein, or an expression vector comprising a fusion polynucleotide disclosed herein.

In some embodiments, a first dose and a second dose are administered by at least 3 days, 4 days, 5 days, 6 days, 7 days, 2 weeks, 3 weeks, or 4 weeks apart.

In some embodiments, a first dose and a second dose are in the same amount.

In some embodiments, a first dose and a second dose are in different amounts.

Further disclosed herein is a method comprising: administering to a subject in need thereof a dose of a pharmaceutical composition disclosed herein, such that the subject receives: a first dose of a pharmaceutical composition that delivers a polynucleotide comprising a nucleotide sequence that encodes a target protein antigen or a target protein antigen encoded by the polynucleotide; and a second dose of a pharmaceutical composition disclosed herein.

In some embodiments, (a) the polynucleotide comprising a nucleotide sequence that encodes a target protein antigen further comprises a nucleotide sequence encoding a complement C3d-binding polypeptide from an immunoglobulin-binding protein (Sbi) of *Staphylococcus aureus*; or (b) the target protein antigen encoded by the polynucleotide further comprises a complement C3d-binding polypeptide from an immunoglobulin-binding protein (Sbi) of *Staphylococcus aureus.*

In some embodiments, the method further comprises, prior to the administering step, administering to the subject the first dose of the pharmaceutical composition that delivers a polynucleotide comprising a nucleotide sequence that encodes a target protein antigen or a target protein antigen encoded by the polynucleotide.

This disclosure provides, a method comprising: administering to a subject in need thereof a dose of a pharmaceutical composition disclosed herein, such that the subject receives: a first dose of the pharmaceutical composition of claim disclosed herein, and a second dose of a pharmaceutical composition that delivers a polynucleotide comprising a nucleotide sequence that encodes a target protein antigen or a target protein antigen encoded by the polynucleotide.

In some embodiments, (a) the polynucleotide comprising a nucleotide sequence that encodes a target protein antigen further comprises a nucleotide sequence encoding a complement C3d-binding polypeptide from an immunoglobulin-binding protein (Sbi) of *Staphylococcus aureus*; or (b) the target protein antigen encoded by the polynucleotide further comprises a complement C3d-binding polypeptide from an immunoglobulin-binding protein (Sbi) of *Staphylococcus aureus.*

Disclosed herein is a method comprising: administering to a subject in need thereof a dose of a pharmaceutical composition disclosed herein, such that the subject receives: a first dose of a pharmaceutical composition that delivers a polynucleotide comprising a nucleotide sequence that encodes a fusion polypeptide comprising (i) a target protein antigen and (ii) a complement C3d-binding polypeptide from an immunoglobulin-binding protein (Sbi) of *Staphylococcus aureus*; or a fusion polypeptide encoded by the polynucleotide; and a second dose of the pharmaceutical composition disclosed herein.

In some embodiments, the method further comprises, prior to the administering step, administering to the subject the first dose of the pharmaceutical composition that delivers a polynucleotide comprising a nucleotide sequence that encodes a fusion polypeptide comprising (i) a target protein antigen and (ii) a complement C3d-binding polypeptide from an immunoglobulin-binding protein (Sbi) of *Staphylococcus aureus*; or a fusion polypeptide encoded by the polynucleotide.

In some embodiments, a first dose and a second dose are administered by at least 3 days, 4 days, 5 days, 6 days, 7 days, 2 weeks, 3 weeks, or 4 weeks apart.

In some embodiments of any of the methods disclosed herein, the subject in need thereof is a subject who is suffering from or is susceptible to a disease, disorder, or condition induced by the target protein antigen.

In some embodiments, a subject is a mammalian subject.

In some embodiments, a subject is a human subject.

In some embodiments, administration can be performed by intramuscular administration, intradermal administration, intravenous administration, subcutaneous administration, or combinations thereof.

Disclosed herein is a composition comprising a fusion polypeptide disclosed herein, or a fusion polynucleotide disclosed herein, or a pharmaceutical composition disclosed herein, for use in enhancing the immunogenicity of an antigen.

Also disclosed herein is a composition comprising a fusion polypeptide disclosed herein, or a fusion polynucleotide disclosed herein, or a pharmaceutical composition disclosed herein, for use in stimulating an immune response against an antigen.

Further disclosed herein is a composition comprising a fusion polypeptide disclosed herein, or a fusion polynucleotide disclosed herein, or a pharmaceutical composition disclosed herein, for use in method of treating a disease or ameliorating a symptom of a disease.

This disclosure provides, a method for enhancing the immunogenicity of an antigen, comprising administering to a subject in need thereof, a fusion polypeptide disclosed herein, or a fusion polynucleotide disclosed herein, or a pharmaceutical composition disclosed herein.

This disclosure also provides a method for stimulating an immune response against an antigen, comprising administering to a subject in need thereof, a fusion polypeptide disclosed herein, or a fusion polynucleotide disclosed herein, or a pharmaceutical composition disclosed herein.

Additionally provided herein is a method of treating a disease or ameliorating a symptom of a disease comprising administering to a subject in need thereof, a fusion polypeptide disclosed herein, or a fusion polynucleotide disclosed herein, or a pharmaceutical composition disclosed herein.

This disclosure provides use of a composition comprising a fusion polypeptide disclosed herein, or a fusion polynucleotide disclosed herein, or a pharmaceutical composition disclosed herein in the preparation of a medicament for enhancing the immunogenicity of a fragment antigen.

This disclosure also provides, use of a composition comprising a fusion polypeptide disclosed herein, or a fusion polynucleotide disclosed herein, or a pharmaceutical composition disclosed herein, in the preparation of a medicament for stimulating an immune response against a antigen.

Further provided herein is use of a composition comprising a fusion polypeptide disclosed herein, or a fusion polynucleotide disclosed herein, or a pharmaceutical composition disclosed herein, in the preparation of a medicament for treating a disease or ameliorating a symptom of a disease.

Provided herein is the use of a composition comprising a fusion polypeptide disclosed herein, or a fusion polynucleotide disclosed herein, or a pharmaceutical composition disclosed herein, for enhancing the immunogenicity of a fragment antigen.

Further provided herein is the use of a composition comprising a fusion polypeptide disclosed herein, or a fusion polynucleotide disclosed herein, or a pharmaceutical composition disclosed herein, for stimulating an immune response against a antigen.

This disclosure provides use of a composition comprising a fusion polypeptide disclosed herein, or a fusion polynucleotide disclosed herein, or a pharmaceutical composition disclosed herein, for treating a disease or ameliorating a symptom of a disease.

In some embodiments of any of the methods or uses disclosed herein, the subject is a mammal.

In some embodiments of any of the methods or uses disclosed herein, the subject is a human.

In some embodiments of any of the methods or uses disclosed herein, a single dose of the fusion polypeptide, fusion polynucleotide or pharmaceutical composition is administered.

In some embodiments of any of the methods or uses disclosed herein, a plurality of doses of the fusion polypeptide, fusion polynucleotide or pharmaceutical composition is administered.

In some embodiments of any of the methods or uses disclosed herein, the fusion polypeptide, fusion polynucleotide or pharmaceutical composition is administered at a dose of about 0.5 micrograms to 10 micrograms.

In some embodiments of any of the methods or uses disclosed herein, administration of the fusion polynucleotide, fusion polypeptide or pharmaceutical composition results in a humoral response. In some embodiments, the humoral response is an antibody response.

In some embodiments of any of the methods or uses disclosed herein, administration of the fusion polynucleotide, fusion polypeptide or pharmaceutical composition results in an increased titer of an antibody response. In some embodiments, the increase in titer is an increase of about 10 fold to about 500 fold. In some embodiments, the increased titer of the antibody response is compared to administration of an otherwise similar fusion polynucleotide that does not comprise an Sbi domain III, or a fragment or variant thereof; and Sbi domain IV, or a fragment or a variant thereof. In some embodiments, the increased titer of the antibody response is compared to administration of an otherwise similar fusion polypeptide that does not comprise an Sbi domain III, or a fragment or variant thereof; and an Sbi domain IV, or a fragment or a variant thereof. In some embodiments, the increased titer of the antibody response is compared to administration of an otherwise similar pharmaceutical composition that does not comprise a nucleotide sequence encoding Sbi domain III, or a fragment or variant thereof; and Sbi domain IV, or a fragment or a variant thereof.

In some embodiments of any of the methods or uses disclosed herein, the composition is administered via any one of the following routes of administration: intramuscular, intravenous, subcutaneous, intrathecal, intradermal, ocular, intranasal, sublingual, or oral.

This disclosure provides, an in vitro method of selecting a fragment antigen by identifying a polypeptide fragment that folds into a three-dimensional conformation that is substantially identical to the three-dimensional conformation as in a target protein antigen from which the fragment is derived.

In some embodiments, the method comprises the steps of: providing a mammalian cell display system that displays a library of fragment antigen candidates on cell surface; exposing the mammalian cell display system to a composition comprising antibodies that bind to a target protein antigen from which the fragment antigen candidates are derived; detecting fragment antigen candidates that bind to the target protein antigen-binding antibodies, wherein the binding of a fragment antigen candidate that binds to at least one of the target protein antigen-binding antibodies is indicative of its likelihood to fold into a three-dimensional conformation that is substantially identical to the three-dimensional conformation as in the target protein antigen.

In some embodiments, the method further comprises a step of generating antibodies that bind to the target protein antigen.

In some embodiments, the generation of the antibodies comprises (i) immunizing animals with a target protein antigen or a polynucleotide encoding the same from which the fragment antigen candidates are derived; and (ii) identifying antibodies that bind to the target protein antigen.

In some embodiments, the mammalian cell display system comprises HEK293T cells, HeLa cells, or CHO cells.

In some embodiments, the polypeptide fragment is identified based on binding affinity to the antibody in a serum binding assay or a similar assay.

Also provided herein is a recombinant polynucleotide comprising a nucleotide sequence encoding an immunoglobulin-binding protein (Sbi) of *Staphylococcus aureus*, or a fragment thereof.

In some embodiments, the polynucleotide comprises a sequence encoding a complement C3d-binding polypeptide from Sbi.

In some embodiments, the complement C3d-binding polypeptide is or comprises one or both of domain III and domain IV of the Sbi of *Staphylococcus aureus*, or a functional fragment or a variant thereof.

In some embodiments, the polynucleotide is or comprises RNA. In some embodiments, the polynucleotide is or comprises messenger RNA.

In some embodiments, the polynucleotide is or comprises DNA.

In some embodiments, the polynucleotide encodes a polypeptide which has at least 80%, 85%, 90%, 91%, 92%, 93%, 94%, 95%, 96%, 97%, 98%, 99% or 100% identity to the nucleotide sequence of SEQ ID NO: 9.

In some embodiments, the polynucleotide encodes a polypeptide which has at least 80%, 85%, 90%, 91%, 92%, 93%, 94%, 95%, 96%, 97%, 98%, 99% or 100% identity to the nucleotide sequence of SEQ ID NO: 10.

This disclosure provides an isolated polypeptide comprising an immunoglobulin-binding protein (Sbi) of *Staphylococcus aureus*.

In some embodiments, the polypeptide comprises a complement C3d-binding polypeptide from Sbi.

In some embodiments, the complement C3d-binding polypeptide is or comprises one or both of domain III and domain IV of the Sbi of *Staphylococcus aureus*, or a functional fragment or a variant thereof.

In some embodiments, the polypeptide has at least 80%, 85%, 90%, 91%, 92%, 93%, 94%, 95%, 96%, 97%, or 100% identity to the amino acid sequence of SEQ ID NO: 9.

In some embodiments, the polypeptide has at least 80%, 85%, 90%, 91%, 92%, 93%, 94%, 95%, 96%, 97%, or 100% identity to the amino acid sequence of SEQ ID NO: 10.

Also provided herein is an expression vector comprising a recombinant polynucleotide comprising a nucleotide sequence encoding an immunoglobulin-binding protein (Sbi) of *Staphylococcus aureus*, or a fragment thereof.

Further provided herein is a composition for delivering an isolated polypeptide comprising an immunoglobulin-binding protein (Sbi) of *Staphylococcus aureus*.

This disclosure also provides a composition for delivering a recombinant polynucleotide comprising a nucleotide sequence encoding an immunoglobulin-binding protein (Sbi) of *Staphylococcus aureus*, or a fragment thereof.

Provided herein is a pharmaceutical composition that delivers a recombinant polynucleotide comprising a nucleotide sequence encoding an immunoglobulin-binding protein (Sbi) of *Staphylococcus aureus*, or a fragment thereof; an isolated polypeptide comprising an immunoglobulin-binding protein (Sbi) of *Staphylococcus aureus*; or an expression vector comprising a recombinant polynucleotide comprising a nucleotide sequence encoding an immunoglobulin-binding protein (Sbi) of *Staphylococcus aureus*, or a fragment thereof.

In some embodiments, the pharmaceutical composition further comprises a pharmaceutically acceptable excipient, a diluent, or a combination thereof.

This disclosure provides a method comprising administering to a subject in need thereof at least one dose of a pharmaceutical composition comprising: a recombinant polynucleotide comprising a nucleotide sequence encoding an immunoglobulin-binding protein (Sbi) of *Staphylococcus aureus*, or a fragment thereof; an isolated polypeptide comprising an immunoglobulin-binding protein (Sbi) of *Staphylococcus aureus*; or an expression vector comprising a recombinant polynucleotide comprising a nucleotide sequence encoding an immunoglobulin-binding protein (Sbi) of *Staphylococcus aureus*, or a fragment thereof.

Further disclosed herein is a method for enhancing the immunogenicity of an antigen, comprising administering to a subject in need thereof, a recombinant polynucleotide comprising a nucleotide sequence encoding an immunoglobulin-binding protein (Sbi) of *Staphylococcus aureus*, or a fragment thereof; an isolated polypeptide comprising an immunoglobulin-binding protein (Sbi) of *Staphylococcus aureus*, or a pharmaceutical composition comprising the same.

This disclosure also provides a method for stimulating an immune response against an antigen, comprising administering to a subject in need thereof, a recombinant polynucleotide comprising a nucleotide sequence encoding an immunoglobulin-binding protein (Sbi) of *Staphylococcus aureus*, or a fragment thereof; an isolated polypeptide comprising an immunoglobulin-binding protein (Sbi) of *Staphylococcus aureus*, or a pharmaceutical composition comprising the same.

Also provided herein is the use of an immunoglobulin-binding protein (Sbi) of *Staphylococcus aureus* as an adjuvant in an immunogenic composition.

This disclosure provides an immunoglobulin-binding protein (Sbi) of *Staphylococcus aureus* for use as an adjuvant in an immunogenic composition.

These, and other aspects encompassed by the present disclosure, are described in more detail below and in the claims.

BRIEF DESCRIPTION OF THE DRAWINGS

FIG. 1A is a schematic showing a likely mechanism of action of Sbi(III-IV) fusions. Sbi(III-IV) binds to C3d, which in turn can drive B cell activation by binding to CR2. C3d-driven B cell co-stimulation is orthogonal to helper T cell activation, which canonically occurs through TCR recognition of a cognate MHCII-peptide complex and CD40 signaling. FIG. 1B is a graph showing a fusion of the RBD domain of SARS-CoV-2 S protein to Sbi(III-IV) leads to increased IgG titers in BALB/c mice at day 21 following a 10 μg dose of IM-delivered mRNA. Co-delivering an RBD fused to the transmembrane domain of S protein (at total mRNA dose of 10 μg) leads to a further increase in titer. The top and bottom horizontal lines indicate the detection limit of the dilution series used in the titer measurement. Sera that had titers that fell outside of that range were given values from the extreme ends of the dilution series. Values are calculated as geometric means, with the error bars corresponding to geometric standard deviation. FIG. 1C is a graph with ELISPOT counts of the number of IFNγ/IL2 double-stained colonies. For each condition, spleens from 5 mice were pooled and plated to 4 wells at 500,000 cells/well. 2 wells each were stimulated by either N-terminal or C-terminal S protein peptide pools (PepMix SARS-CoV-2 Spike Glycoprotein mix). Rates were calculated by pooling colony counts across the 4 wells, and the error bars were calculated as the Poisson error of the pooled colony counts. FIG. 1D is a graph depicting fusion fragments of RBD domain of S protein can lead to detectable humoral responses. Data displayed as described in FIG. 1B.

FIG. 2A is a schematic of a screen for protein folding. Anti-sera are generated by vaccinating mice with an mRNA vaccine encoding the full-length protein of interest. The collected anti-sera are then used to detect properly folded fragments presented in the context of a mammalian display system in a library of protein fragments. FIG. 2B is a graph showing positive and negative controls to validate the screening strategy. RBD from SARS-CoV-2 presented on the surface of HEK 293T cells and stained with anti-sera collected from RBD-vaccinated mice.

FIG. 7A shows the context of Y98, S/K136, W153, H183, and L/I194 receptor-contacting residues within the structure of an HAI glycoprotein trimer. FIG. 7B depicts the conservation of receptor-contacting residues across strains spanning 92 years of seasonal influenza (SEQ ID NOs: 63-74).

CERTAIN DEFINITIONS

Figures 1A, 1B, 1C, 1D:
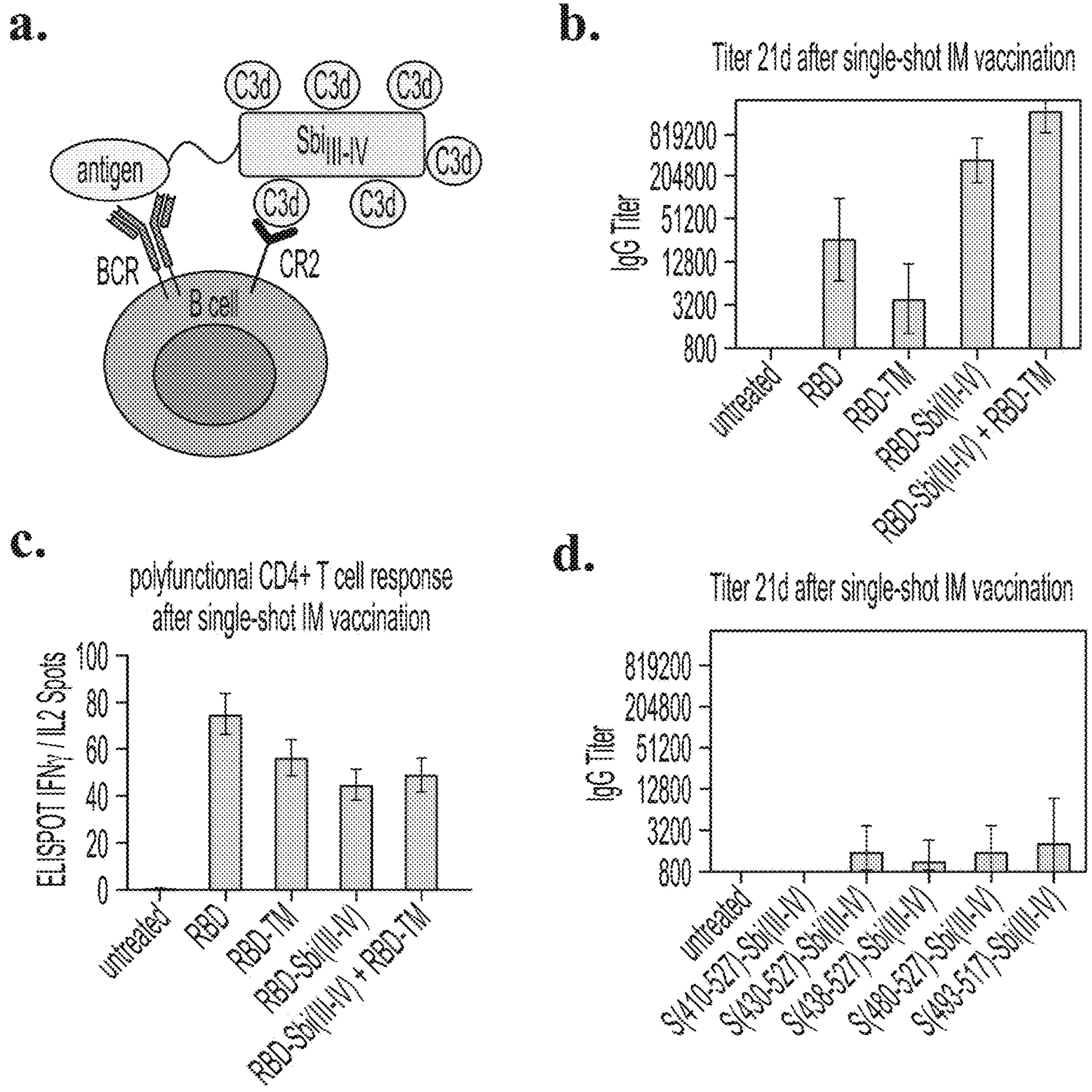
FIGS. 1A-1D describe improved antigenicity of isolated SARS-CoV-2 S protein domains with Sbi(III-IV) fusions.

About or approximately: As used herein, the terms "about" and "approximately," when used herein in reference to a value, refers to a value that is similar, in context to the referenced value. In general, those skilled in the art, familiar with the context, will appreciate the relevant degree of variance encompassed by "about" or "approximately" in that context. For example, in some embodiments, the term "about" or "approximately" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administering: As used herein, the term "administering" or "administration" typically refers to administration of a composition to a subject to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Adjuvant: The term "adjuvant," as used herein, refers to an agent that modulates and/or enhances an immune response to an agent that elicits an immune response. In some embodiments, an adjuvant is administered before, concurrently with or after administration of an agent that elicits an immune response. In some embodiments, an adjuvant and an agent that elicits an immune response are in one composition. In some embodiments, an adjuvant and an agent that elicits an immune response are in different compositions. In some embodiments, an adjuvant is or comprises a nucleic acid, polypeptide, polysaccharide, or small molecule. In some embodiments, an adjuvant is or comprises a complement binding domain. In some embodiments, an adjuvant is or comprises a C3d binding domain. In some embodiments, an adjuvant is or comprises a domain III of Sbi immunoglobulin-binding protein of *Staphylococcus aureus*, or a functional fragment or variant thereof. In some embodiments, an adjuvant is or comprises a domain IV of Sbi immunoglobulin-binding protein of *Staphylococcus aureus*, or a functional fragment or variant thereof. In some embodiments, an adjuvant comprises both a domain III and a domain IV of the Sbi of *Staphylococcus aureus*, or a functional fragment or a variant thereof.

Antigen: The term "antigen", as used herein, refers to an agent that elicits an immune response; and/or (ii) an agent that binds to a T cell receptor (e.g., when presented by an MHC molecule) or to an antibody. In some embodiments, an antigen elicits a humoral response (e.g., including production of antigen-specific antibodies); in some embodiments, an antigen elicits a cellular response (e.g., involving T-cells whose receptors specifically interact with the antigen). In some embodiments, an antigen comprises at least one epitope of a target protein. In some embodiments, an epitope may be a linear epitope. In some embodiments, an epitope may be a conformational epitope. In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer [e.g., other than a nucleic acid or amino acid polymer) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen.

Antigen variant: As used herein, the term "antigen variant" refers to an antigen that shows significant structural identity with a target protein antigen but differs structurally from the target protein antigen in the presence or level of one or more chemical moieties as compared to the target protein antigen. In some embodiments, an antigen variant differs functionally from a target protein antigen. In some embodiments, an antigen variant does not differ functionally from a target protein antigen. In some embodiments, an antigen comprises an epitope of a target protein antigen. In some embodiments, an antigen variant differs from a target protein antigen as a result of one or more differences in amino acid sequence and/or one or more differences in chemical moieties (e.g., carbohydrates, lipids, etc.) covalently attached to the polypeptide backbone.

Delivery/contacting: As used interchangeably herein, the term "delivery," "delivering," or "contacting" refers to introduction of a fusion polynucleotide (e.g., as described herein) or a fusion polypeptide (e.g., as described herein) into a target cell. A target cell can be cultured in vitro or ex vivo or be present in a subject (in vivo). Methods of introducing a fusion polynucleotide (e.g., as described herein) or a fusion polypeptide (e.g., as described herein) into a target cell can vary with in vitro, ex vivo, or in vivo applications. In some embodiments, a fusion polynucleotide (e.g., as described herein) or a fusion polypeptide (e.g., as described herein) can be introduced into a target cell in a cell culture by in vitro transfection. In some embodiments, a fusion polynucleotide (e.g., as described herein) or a fusion polypeptide (e.g., as described herein) can be introduced into a target cell via delivery vehicles (e.g., nanoparticles, liposomes, and/or complexation with a cell-penetrating agent). In some embodiments, a fusion polynucleotide (e.g., as described herein) or a fusion polypeptide (e.g., as described herein) can be introduced into a target cell in a subject by administering a fusion polynucleotide (e.g., as described herein) or a fusion polypeptide (e.g., as described herein) to a subject.

Functional: As used herein, the term "functional" is used to refer to a form or fragment of an entity that exhibits a particular property and/or activity.

Fragment: A "fragment" of a material or entity as described herein has a structure that includes a discrete portion of the whole, but lacks one or more moieties found in the whole. In some embodiments, a fragment consists of such a discrete portion. In some embodiments, a fragment consists of or comprises a characteristic structural element or moiety found in the whole. In some embodiments, a fragment comprises a polynucleotide fragment. In some embodiments, a fragment comprises a polypeptide fragment. In some embodiments, a polynucleotide fragment or a polypeptide fragment comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polynucleotide or whole polypeptide. In some embodiments, a polynucleotide fragment or a polypeptide fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polynucleotide or whole polypeptide. The whole polypeptide or whole polynucleotide may in some embodiments be referred to as the "parent" of the polynucleotide fragment or polypeptide fragment.

Fragment antigen: A "fragment antigen" is used herein to refer to a fragment which comprises an epitope of a target protein antigen. In some embodiments, an epitope is or comprises an epitope presented by MHC Class I. In some embodiments, an epitope is or comprises an epitope presented by MHC Class II. In some embodiments, a fragment antigen is a polypeptide fragment antigen. In some embodiments, a fragment antigen is encoded by a polynucleotide encoding a fragment antigen. In some embodiments, a polypeptide fragment antigen comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 200, 250, 300 or more monomeric units (e.g., residues) as found in a target protein antigen polypeptide. In some embodiments, a polypeptide fragment antigen comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in a target protein antigen polypeptide. In some embodiments, a polypeptide fragment antigen comprises or consists of no more than about 50%, 40%, 30%, 20%, 10%, or 5% of the monomeric units (e.g., residues) found in a target protein antigen polypeptide.

Fragment antigen variant: As used herein, the term "fragment antigen variant" refers to a fragment antigen that shows significant sequence and/or structural identity with a fragment antigen but differs in sequence and/or structure from the fragment antigen in the presence or level of one or more chemical moieties as compared to the fragment antigen. In some embodiments, a fragment antigen variant differs functionally from a fragment antigen. In some embodiments, a fragment antigen variant does not differ functionally from a fragment antigen. In some embodiments, a fragment antigen variant differs from a fragment antigen as a result of one or more differences in amino acid sequence and/or one or more differences in chemical moieties (e.g., carbohydrates, lipids, etc.) covalently attached to the polypeptide backbone.

Nucleic acid/Oligonucleotide/Polynucleotide: As used herein, the terms "nucleic acid" and "polynucleotide" and "oligonucleotide" are used interchangeably, and refer to a polymer of 3 nucleotides or more. In some embodiments, a nucleic acid comprises DNA. In some embodiments, a nucleic acid comprises RNA. In some embodiments, a nucleic acid comprises messenger RNA (mRNA). In some embodiments, a nucleic acid is single stranded. In some embodiments, a nucleic acid is double stranded. In some embodiments, a nucleic acid comprises both single and double stranded portions. In some embodiments, a nucleic acid comprises a backbone that comprises one or more phosphodiester linkages. In some embodiments, a nucleic acid comprises a backbone that comprises both phosphodiester and non-phosphodiester linkages. For example, in some embodiments, a nucleic acid may comprise a backbone that comprises one or more phosphorothioate or 5'-N-phosphoramidite linkages and/or one or more peptide bonds, e.g., as in a "peptide nucleic acid". In some embodiments, a nucleic acid comprises one or more, or all, natural residues (e.g., adenine, cytosine, deoxyadenosine, deoxycytidine, deoxyguanosine, deoxythymidine, guanine, thymine, uracil). In some embodiments, a nucleic acid comprises on or more, or all, non-natural residues. In some embodiments, a non-natural residue comprises a nucleoside analog (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 6-O-methylguanine, 2-thiocytidine, methylated bases, intercalated bases, and combinations thereof). In some embodiments, a non-natural residue comprises one or more modified sugars (e.g., 2'-fluororibose, ribose, 2'-deoxyribose, arabinose, and hexose) as compared to those in natural residues. In some embodiments, a nucleic acid has a nucleotide sequence that encodes a functional gene product such as an RNA or polypeptide. In some embodiments, a nucleic acid has a nucleotide sequence that comprises one or more introns. In some embodiments, a nucleic acid may be prepared by isolation from a natural source, enzymatic synthesis (e.g., by polymerization based on a complementary template, e.g., in vivo or in vitro, reproduction in a recombinant cell or system, or chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 1 10, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, or 20,000 or more residues or nucleotides long. When a number of nucleotides is used as an indication of size, e.g., of a fusion polynucleotide, a certain number of nucleotides refers to the number of nucleotides on a single strand, e.g., of a fusion polynucleotide.

Polypeptide: The term “polypeptide”, as used herein, generally has its art-recognized meaning of a polymer of at least three amino acids or more. Those of ordinary skill in the art will appreciate that the term “polypeptide” is intended to be sufficiently general as to encompass not only polypeptides having a complete sequence recited herein, but also to encompass polypeptides that represent functional, biologically active, or characteristic fragments, portions or domains (e.g., fragments, portions, or domains retaining at least one activity) of such complete polypeptides. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, polypeptides may comprise natural amino acids, non-natural amino acids, synthetic amino acids, and combinations thereof.

RNA oligonucleotide: As used herein, the term “RNA oligonucleotide” refers to an oligonucleotide of ribonucleotides. In some embodiments, an RNA oligonucleotide is single stranded. In some embodiments, an RNA oligonucleotide is double stranded. In some embodiments, an RNA oligonucleotide comprises both single and double stranded portions. In some embodiments, an RNA oligonucleotide can comprise a backbone structure as described in the definition of “Nucleic acid/Oligonucleotide” above. An RNA oligonucleotide can be a regulatory RNA (e.g., siRNA, microRNA, etc.), or a messenger RNA (mRNA) oligonucleotide. In some embodiments where an RNA oligonucleotide is a mRNA oligonucleotide, an RNA oligonucleotide typically comprises at its 3' end a poly(A) region. In some embodiments where an RNA oligonucleotide is a mRNA oligonucleotide, an RNA oligonucleotide typically comprises at its 5' end an art-recognized cap structure, e.g., for recognizing and attachment of a mRNA to a ribosome to initiate translation. In some embodiments, a polynucleotide (e.g., a fusion polynucleotide) comprises an RNA oligonucleotide. When a number of ribonucleotides is used as an indication of size, e.g., of a fusion polynucleotide, a certain number of nucleotides refers to the number of ribonucleotides on a single strand, e.g., of a fusion polynucleotide.

Subject: As used herein, the term “subject” refers an organism, typically a mammal (e.g., a human). In some embodiments, a subject is suffering from a disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Variant: As used herein, the term “variant” refers to an entity that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a “variant” of a reference entity is based on its degree of structural identity with the reference entity. For example, a variant polypeptide may differ from a reference polypeptide as a result of one or more differences in amino acid sequence and/or one or more differences in chemical moieties (e.g., carbohydrates, lipids, etc.) covalently attached to the polypeptide backbone. Alternatively or additionally, in some embodiments, a variant polypeptide does not share at least one characteristic sequence element with a reference polypeptide. In some embodiments, the reference polypeptide has one or more biological activities. In some embodiments, a variant polypeptide shares one or more of the biological activities of the reference polypeptide. In some embodiments, a variant polypeptide lacks one or more of the biological activities of the reference polypeptide. In some embodiments, a variant polypeptide shows a reduced level of one or more biological activities as compared with the reference polypeptide.

Standard techniques may be used for recombinant DNA, oligonucleotide synthesis, e.g., mRNA synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2nd ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

Traditional vaccine adjuvants, such as alum and poly-IC, typically work by activating one or more Toll like receptors (TLR) and thereby putting local tissue into an anti-viral state. In contrast, achieving high levels of antigen production with RNA vaccines, e.g., mRNA vaccines, demands minimal immunogenicity, as localized innate immune responses can dramatically reduce expression levels. This disclosure provides an RNA-native adjuvant technology, e.g., mRNA-native adjuvant technology, that can provide improvements in the strength of the immune response, without creating a countervailing effect on antigen expression. This can be accomplished, e.g., by using protein-based fusions to make the RNA-encoded antigen, e.g., mRNA-encoded antigen, more immunogenic in a way that was decoupled from the immunogenicity of the vaccine itself. In one embodiment, the fusion protein would either directly stimulate and/or drive uptake by B cells, while minimizing non-specific inflammation at the site of RNA, e.g., mRNA, expression. A large set of candidate fusion domains were screened, and it was observed that Sbi fragments described herein improved antibody titers across a range of antigen expression levels. This represents a first-in-class solution to making adjuvants that work well with RNA-based, e.g., mRNA-based, vaccines. Since viral and DNA vaccine vectors face the same immunogenicity-antigen expression optimization challenge, Sbi fragments described herein, e.g., SbiIII-IV, can be used to improve other classes of nucleic acid-based vaccines.

Without wishing to be bound by theory, it is believed that given what is known about the mechanism of action of SbiIII-IV, the fusion approach described herein has the additional benefit of extending the design space of effective antigens. Antibody production is driven by B cells that both 1) bind the antigen via their B cell receptor (BCR); and 2) become activated by a second signal. The activation signal is most commonly provided by a helper T cell, which means that effective antigens need to both bind BCRs, and contain peptides that are efficiently presented on MHC and that bind T cell receptor (TCR)s. SbiIII-IV, in contrast, binds to complement fragments that can directly license B cells, bypassing the need to generate a strong response in helper T cells. This can extend the design space of effective antigens by enabling, e.g., the use of fragments that lack good T cell epitopes. In some embodiments, one of the applications of the SbiIII-IV-based fusion architecture is to make minimal antigens containing only a portion of the naturally occurring protein. As an example, this disclosure provides compositions and uses of SbiIII-IV-based fusions comprising a portion of the SARS-CoV-2 spike protein (e.g., RBD and sub-RBD portions) as an exemplary antigen fused to an Sbi fragment (SbiIII-IV) which have enhanced antigenicity (see Example 1) and/or stimulate a productive humoral immune response (see Examples 2-4).

The present disclosure is the first to recognize that vaccination with a fragment antigen fused to an adjuvant comprising a complement C3d-binding region, can enhance the titers of the resulting antibody response and/or result in a measurable T cell response. In some embodiments, the adjuvant is or comprises a complement C3d-binding region of a Sbi protein from *Staphylococcus aureus*. In some embodiments, a fragment antigen fused to an adjuvant comprising a complement C3d-binding region serves as a synthetic immunological synapse, mimicking natural viral infection to drive a strong and appropriate immune response. In some embodiments, a fragment antigen fused to an adjuvant comprising a complement C3d-binding region allows small antigens that lack MHC-presented peptides to elicit meaningful humoral response.

The present disclosure also recognizes that vaccination with a fragment antigen or a variant antigen (instead of a full-length antigen) can be useful for developing vaccines that are less resistant to viral mutations and are broadly neutralizing. The vaccination approaches described herein can focus the immune response on conserved and/or functional regions to improve the breadth and efficacy of a vaccine. Without wishing to be bound by theory, it is believed that in some embodiments, immunofocusing can occur with use of fragment antigens that: (1) minimally comprise an epitope of a target protein antigen which can be presented on MHC I and/or MHC II; and/or (2) have a confirmation that is similar to that of the full-length or native target protein antigen.

Fragment Antigens or Variant Antigens

This disclosure provides fragment antigens or variant antigens which comprise an epitope of a target protein antigen and compositions comprising the same. In some embodiments, a fragment antigen or a variant antigen is fused to an adjuvant, e.g., a C3d binding polypeptide, for use in an immunogenic composition.

In some embodiments, a fragment antigen or a variant antigen comprises an epitope (e.g., T cell epitope) of a target protein antigen. In some embodiments, a fragment antigen or a variant antigen comprises a portion of an epitope (e.g., T cell epitope) of a target protein antigen.

In some embodiments, a fragment antigen or a variant antigen does not comprise an epitope e.g., T cell epitope) of a target protein antigen.

In some embodiments, a fragment antigen has an amino acid sequence length of at least 5%, 10%, 20%, 30%, 40%, 50%, 60%, 70%, 80%, 90% or 95% compared to the amino acid sequence length of the target protein antigen. In some embodiments, a fragment antigen has an amino acid sequence length of no more than 50% of the amino acid sequence length of the target protein antigen. In some embodiments, a fragment antigen has an amino acid sequence length of no more than 40%, 30%, 20%, 10% or 5% of the amino acid sequence length of the target protein antigen.

In some embodiments, a fragment antigen has about 10-300 amino acid residues in length. In some embodiments, a fragment antigen has at least 10 amino acid residues in length. In some embodiments, a fragment antigen has less than about 300 amino acid residues in length. In some embodiments, a fragment antigen has about 10-300, 10-250, 10-200, 10-150, 10-100, 10-90, 10-80, 10-70, 10-60, 10-50, 10-40, 10-30, 10-20, 20-300, 30-300, 40-300, 50-300, 60-300, 70-300, 80-300, 90-100, 100-300, 150-300, 200-300, 250-300, 20-250, 30-200, 40-150, 50-100, 60-90, or 70-80 amino acids residues in length. In some embodiments, a fragment antigen has about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 amino acids residues in length.

In some embodiments, an antigen variant or fragment antigen variant amino acid sequence length is identical to the amino acid sequence length of the target protein antigen.

In some embodiments, an antigen variant or fragment antigen variant comprises at least one modified amino acid compared to the target protein antigen. In some embodiments, a modified amino acid comprises N-linked glycosylation. In some embodiments, an antigen variant or fragment antigen variant comprises at least one amino acid mutation compared to the target protein antigen. In some embodiments, an antigen variant or fragment antigen variant comprises 2, 3, 4, 5, 6, 7, 8, 9, 10, 15, 20, 30, 40 or 50 amino acid mutations compared to the target protein antigen. In some embodiments, the mutation introduces a Serine, a Threonine, an Alanine, or an amino acid at a particular position which is different from the amino acid present at that position in the target protein antigen. In some embodiments, the mutation prevents formation of a disulfide bond.

In some embodiments, a fragment antigen is characterized in that when expressed in vivo, it binds to a Major Histocompatibility Complex (MHC) molecule.

In some embodiments, a fragment antigen is characterized in that when expressed in vivo, it does not bind to a MHC molecule.

In some embodiments, a MHC molecule is or comprises a MHC I molecule or a MHC II molecule.

In some embodiments, a fragment antigen is characterized in that when expressed in vivo, it folds into a three-dimensional conformation that is substantially identical to the three-dimensional conformation of the fragment antigen as it is in its native position in the target protein antigen.

In some embodiments, a fragment antigen, antigen variant or fragment antigen variant further comprises an amino acid sequence from a second target protein antigen.

Target Protein Antigens

Among other things, provided herein are fusion polypeptides comprising a fragment antigen or a variant antigen comprising an epitope of a target protein antigen. Also provided herein are fusion polynucleotides encoding fusion polypeptides comprising a fragment antigen or a variant antigen comprising an epitope of a target protein antigen.

In some embodiments, a target protein antigen is or comprises an infectious disease antigen. In some embodiments, an infectious disease antigen is or comprises a viral antigen, a bacterial antigen, a fungal antigen, or combinations thereof. In some embodiments, a viral antigen is or comprises an influenza antigen. In some embodiments, a viral antigen is or comprises a coronavirus polypeptide. In some embodiments, a coronavirus polypeptide is or comprises a SARS-CoV-2 protein, e.g., as described herein.

In some embodiments, a target protein antigen is or comprises a cancer antigen.

SARS-CoV-2 Antigens

Exemplary antigens that can be included in any of the fusion polypeptides, fusion polynucleotides, compositions, methods or uses disclosed herein include one or more SARS-CoV-2 polypeptides. In some embodiments, a target protein antigen disclosed herein is or comprises a SARS-CoV-2 antigen. In some embodiments, a SARS-CoV-2 antigen is chosen from: a Spike glycoprotein (SARS-CoV-2 S) polypeptide or antigenic fragment thereof; an Envelope protein (SARS-CoV-2 E) polypeptide or antigenic fragment thereof; a Membrane protein (SARS-CoV-2 M) polypeptide or antigenic fragment thereof; a nucleocapsid protein (SARS-CoV-2 N) polypeptide or antigenic fragment thereof; an accessory factor polypeptide or antigenic fragment thereof; or any combination thereof.

In some embodiments, an antigen, e.g., a fragment antigen or a variant antigen, comprises an epitope from a target protein antigen which is or comprises a SARS-CoV-2 polypeptide. In some embodiments, an antigen, e.g., a fragment antigen or a variant antigen, comprises an epitope from a SARS-CoV-2 Spike glycoprotein (SARS-CoV-2 S) polypeptide or a fragment thereof (e.g., RBD).

The SARS-CoV-2 S polypeptide is referenced by Gene ID: 43740568 and/or NCBI RefNC_045512.2. An amino acid sequence for SARS-CoV-2 S polypeptide is provided by SEQ ID NO: 58:

```
MFVFLVLLPLVSSQCVNLTTRTQLPPAYTNSFTRGVYYPDKVFR
SSVLHSTQDLFLPFFSNVTWFHAIHVSGTNGTKRFDNPVLPFNDGVYFAS
TEKSNIIRGWIFGTTLDSKTQSLLIVNNATNVVIKVCEFQFCNDPFLGVY
YHKNNKSWMESEFRVYSSANNCTFEYVSQPFLMDLEGKQGNFKNLREFVF
KNIDGYFKIYSKHTPINLVRDLPQGFSALEPLVDLPIGINITRFQTLLAL
HRSYLTPGDSSSGWTAGAAAYYVGYLQPRTFLLKYNENGTITDAVDCALD
PLSETKCTLKSFTVEKGIYQTSNFRVQPTESIVRFPNITNLCPFGEVFNA
TRFASVYAWNRKRISNCVADYSVLYNSASFSTFKCYGVSPTKLNDLCFTN
VYADSFVIRGDEVRQIAPGQTGKIADYNYKLPDDFTGCVIAWNSNNLDSK
VGGNYNYLYRLFRKSNLKPFERDISTEIYQAGSTPCNGVEGFNCYFPLQS
YGFQPTNGVGYQPYRVVVLSFELLHAPATVCGPKKSTNLVKNKCVNFNFN
GLTGTGVLTESNKKFLPFQQFGRDIADTTDAVRDPQTLEILDITPCSFGG
VSVITPGTNTSNQVAVLYQDVNCTEVPVAIHADQLTPTWRVYSTGSNVFQ
TRAGCLIGAEHVNNSYECDIPIGAGICASYQTQTNSPRRARSVASQSIIA
YTMSLGAENSVAYSNNSIAIPTNFTISVTTEILPVSMTKTSVDCTMYICG
DSTECSNLLLQYGSFCTQLNRALTGIAVEQDKNTQEVFAQVKQIYKTPPI
KDFGGFNFSQILPDPSKPSKRSFIEDLLFNKVTLADAGFIKQYGDCLGDI
AARDLICAQKFNGLTVLPPLLTDEMIAQYTSALLAGTITSGWTFGAGAAL
QIPFAMQMAYRFNGIGVTQNVLYENQKLIANQFNSAIGKIQDSLSSTASA
LGKLQDVVNQNAQALNTLVKQLSSNFGAISSVLNDILSRLDKVEAEVQID
RLITGRLQSLQTYVTQQLIRAAEIRASANLAATKMSECVLGQSKRVDFCG
KGYHLMSFPQSAPHGVVFLHVTYVPAQEKNFTTAPAICHDGKAHFPREGV
FVSNGTHWFVTQRNFYEPQIITTDNTFVSGNCDVVIGIVNNTVYDPLQPE
LDSFKEELDKYFKNHTSPDVDLGDISGINASVVNIQKEIDRLNEVAKNLN
ESLIDLQELGKYEQYIKWPWYIWLGFIAGLIAIVMVTIMLCCMTSCCSCL
KGCCSCGSCCKFDEDDSEPVLKGVKLHYT
```

A polynucleotide sequence for SARS-CoV-2 S polypeptide is provided by SEQ ID NO: 59:

```
  1 atgtttgttt ttcttgtttt attgccacta gtctctagtc agtgtgttaa tcttacaacc
 61 agaactcaat tacccoctgc atacactaat tctttcacac gtggtgttta ttaccctgac
121 aaagttttca gatcctcagt tttacattca actcaggact tgttcttacc tttcttttcc
181 aatgttactt ggttccatgc tatacatgtc tctgggacca atggtactaa gaggtttgat
241 aaccctgtcc taccatttaa tgatggtgtt tattttgctt ccactgagaa gtctaacata
301 ataagaggct ggatttttgg tactacttta gattcgaaga cccagtccct acttattgtt
```

-continued

```
 361 aataacgcta ctaatgttgt tattaaagtc tgtgaatttc aattttgtaa tgatccattt
 421 ttgggtgttt attaccacaa aaacaacaaa agttggatgg aaagtgagtt cagagtttat
 481 tctagtgcga ataattgcac ttttgaatat gtctctcagc cttttcttat ggaccttgaa
 541 ggaaaacagg gtaatttcaa aaatcttagg gaatttgtgt ttaagaatat tgatggttat
 601 tttaaaatat attctaagca cacgcctatt aatttagtgc gtgatctccc tcagggtttt
 661 tcggctttag aaccattggt agatttgcca ataggtatta acatcactag gtttcaaact
 721 ttacttgctt tacatagaag ttatttgact cctggtgatt cttcttcagg ttggacagct
 781 ggtgctgcag cttattatgt gggttatctt caacctagga cttttctatt aaaatataat
 841 gaaaatggaa ccattacaga tgctgtagac tgtgcacttg accctctctc agaaacaaag
 901 tgtacgttga aatccttcac tgtagaaaaa ggaatctatc aaacttctaa ctttagagtc
 961 caaccaacag aatctattgt tagatttcct aatattacaa acttgtgccc ttttggtgaa
1021 gtttttaacg ccaccagatt tgcatctgtt tatgcttgga acaggaagag aatcagcaac
1081 tgtgttgctg attattctgt cctatataat tccgcatcat tttccacttt taagtgttat
1141 ggagtgtctc ctactaaatt aaatgatctc tgctttacta atgtctatgc agattcattt
1201 gtaattagag gtgatgaagt cagacaaatc gctccagggc aaactggaaa gattgctgat
1261 tataattata aattaccaga tgattttaca ggctgcgtta tagcttggaa ttctaacaat
1321 cttgattcta aggttggtgg taattataat tacctgtata gattgtttag gaagtctaat
1381 ctcaaacctt ttgagagaga tatttcaact gaaatctatc aggccggtag cacaccttgt
1441 aatggtgttg aaggttttaa ttgttacttt cctttacaat catatggttt ccaacccact
1501 aatggtgttg gttaccaacc atacagagta gtagtacttt cttttgaact tctacatgca
1561 ccagcaactg tttgtggacc taaaaagtct actaatttgg ttaaaaacaa atgtgtcaat
1621 ttcaacttca atggtttaac aggcacaggt gttcttactg agtctaacaa aaagtttctg
1681 cctttccaac aatttggcag agacattgct gacactactg atgctgtccg tgatccacag
1741 acacttgaga ttcttgacat tacaccatgt tcttttggtg gtgtcagtgt tataacacca
1801 ggaacaaata cttctaacca ggttgctgtt ctttatcagg atgttaactg cacagaagtc
1861 cctgttgcta ttcatgcaga tcaacttact cctacttggc gtgtttattc tacaggttct
1921 aatgtttttc aaacacgtgc aggctgttta atagggggctg aacatgtcaa caactcatat
1981 gagtgtgaca tacccattgg tgcaggtata tgcgctagtt atcagactca gactaattct
2041 cctcggcggg cacgtagtgt agctagtcaa tccatcattg cctacactat gtcacttggt
2101 gcagaaaatt cagttgctta ctctaataac tctattgcca tacccacaaa ttttactatt
2161 agtgttacca cagaaattct accagtgtct atgaccaaga catcagtaga ttgtacaatg
2221 tacatttgtg gtgattcaac tgaatgcagc aatcttttgt tgcaatatgg cagtttttgt
2281 acacaattaa accgtgcttt aactggaata gctgttgaac aagacaaaaa cacccaagaa
2341 gtttttgcac aagtcaaaca aatttacaaa acaccaccaa ttaaagattt tggtggtttt
2401 aatttttcac aaatattacc agatccatca aaaccaagca agaggtcatt tattgaagat
2461 ctacttttca acaaagtgac acttgcagat gctggcttca tcaaacaata tggtgattgc
2521 cttggtgata ttgctgctag agacctcatt tgtgcacaaa agtttaacgg ccttactgtt
2581 ttgccacctt tgctcacaga tgaaatgatt gctcaataca cttctgcact gttagcgggt
2641 acaatcactt ctggttggac ctttggtgca ggtgctgcat tacaaatacc atttgctatg
2701 caaatggctt ataggtttaa tggtattgga gttacacaga atgttctcta tgagaaccaa
```

-continued

```
2761 aaattgattg ccaaccaatt taatagtgct attggcaaaa ttcaagactc actttcttcc
2821 acagcaagtg cacttggaaa acttcaagat gtggtcaacc aaaatgcaca agctttaaac
2881 acgcttgtta aacaacttag ctccaatttt ggtgcaattt caagtgtttt aaatgatatc
2941 ctttcacgtc ttgacaaagt tgaggctgaa gtgcaaattg ataggttgat cacaggcaga
3001 cttcaaagtt tgcagacata tgtgactcaa caattaatta gagctgcaga aatcagagct
3061 tctgctaatc ttgctgctac taaaatgtca gagtgtgtac ttggacaatc aaaaagagtt
3121 gatttttgtg gaaagggcta tcatcttatg tccttccctc agtcagcacc tcatggtgta
3181 gtcttcttgc atgtgactta tgtccctgca caagaaaaga acttcacaac tgctcctgcc
3241 atttgtcatg atggaaaagc acactttcct cgtgaaggtg tctttgtttc aaatggcaca
3301 cactggtttg taacacaaag gaatttttat gaaccacaaa tcattactac agacaacaca
3361 tttgtgtctg gtaactgtga tgttgtaata ggaattgtca acaacacagt ttatgatcct
3421 ttgcaacctg aattagactc attcaaggag gagttagata aatattttaa gaatcataca
3481 tcaccagatg ttgatttagg tgacatctct ggcattaatg cttcagttgt aaacattcaa
3541 aaagaaattg accgcctcaa tgaggttgcc aagaatttaa atgaatctct catcgatctc
3601 caagaacttg gaaagtatga gcagtatata aaatggccat ggtacatttg gctaggtttt
3661 atagctggct tgattgccat agtaatggtg acaattatgc tttgctgtat gaccagttgc
3721 tgtagttgtc tcaagggctg ttgttcttgt ggatcctgct gcaaatttga tgaagacgac
3781 tctgagccag tgctcaaagg agtcaaatta cattacacat aa
```

In some embodiments, a target protein antigen is or comprises a SARS-CoV-2 S polypeptide. In some embodiments, a target protein antigen comprises a polypeptide having at least 80%, 85%, 90%, 91%, 92%, 93%, 94%, 95%, 96%, 97%, 98%, 99% or 100% identity to an amino acid sequence of a SARS-CoV-2 S polypeptide or a fragment thereof as described herein. In some embodiments, a target protein antigen comprises a polypeptide having at least 80%, 85%, 90%, 91%, 92%, 93%, 94%, 95%, 96%, 97%, 98%, 99% or 100% identity to the amino acid sequence of SEQ ID NO: 58.

In some embodiments, a fragment antigen comprises an epitope of a SARS-CoV-2 S polypeptide. In some embodiments, a fragment antigen comprises a polypeptide having at least 80%, 85%, 90%, 91%, 92%, 93%, 94%, 95%, 96%, 97%, 98%, 99% or 100% identity to an amino acid sequence of a SARS-CoV-2 S polypeptide or a fragment thereof as described herein. In some embodiments, a fragment antigen comprises a polypeptide having at least 80%, 85%, 90%, 91%, 92%, 93%, 94%, 95%, 96%, 97%, 98%, 99% or 100% identity to the amino acid sequence of SEQ ID NO: 58.

In some embodiments, a fragment antigen comprises an epitope of a SARS-CoV-2 S polypeptide. In some embodiments, a fragment antigen comprises a polynucleotide encoding a polypeptide having at least 80%, 85%, 90%, 91%, 92%, 93%, 94%, 95%, 96%, 97%, 98%, 99% or 100% identity to an amino acid sequence of a SARS-CoV-2 S polypeptide or a fragment thereof as described herein. In some embodiments, a fragment antigen comprises a polynucleotide having at least 80%, 85%, 90%, 91%, 92%, 93%, 94%, 95%, 96%, 97%, 98%, 99% or 100% identity to the nucleic acid sequence of SEQ ID NO: 59. Due to degeneracy in the genetic code, those of ordinary skill in the art would understand that other DNA sequences (including codon-optimized sequences) could encode these polypeptides, as well as the others disclosed herein.

Adjuvants

In some embodiments, an adjuvant disclosed herein can be used to elicit and/or modulate an immune response elicited by an antigen (e.g., fragment antigen or antigen variant) described herein. In some embodiments, an adjuvant disclosed herein comprises a complement binding polypeptide. In some embodiments, a complement binding polypeptide comprises a complement C3d binding polypeptide. An exemplary C3d binding polypeptide is an immunoglobulin-binding protein (Sbi) of *Staphylococcus aureus*.

In some embodiments of any of the fusion polypeptides, fusion nucleotides, compositions, methods or uses disclosed herein, an adjuvant disclosed herein can be used alone or in combination with an antigen disclosed herein to modulate and/or enhance an immune response. In an embodiment, an adjuvant disclosed herein can comprise a fusion polypeptide which comprises a fragment antigen or variant antigen and an adjuvant (e.g., C3d binding polypeptide). In some embodiments, also disclosed herein are fusion polynucleotides encoding fusion polypeptides comprising a fragment antigen or variant antigen and an adjuvant (e.g., C3d binding polypeptide). In some embodiments, a fusion polynucleotide comprises DNA or RNA. In some embodiments, a fusion polynucleotide comprises RNA, e.g., messenger RNA. In some embodiments, a fusion polynucleotide comprising RNA (e.g., messenger RNA) is characterized in that when administered to a subject reduces immunogenicity to an antigen comprised in the fusion polynucleotide.

*S. aureus* Sbi

As disclosed herein, *S. aureus* binder of immunoglobulin (Sbi) is an exemplary polypeptide which can bind complement C3d (as described in Clark et al. (2011) *Mol Immunol.* 48(4): 452-462, the entire contents of which is incorporated herein by reference). Sbi comprises two immunoglobulin binding domains (Domains I and II) and two complement C3d binding domains (Domains III and IV). Sbi domains III and IV can bind C3d (in native C3, iC3b and C3dg) and can result in fluid phase consumption of C3 via activation of the alternative pathway (see Clark et al 2011). It has also been shown that Sbi can be secreted and is involved in *S. aureus* immune evasion (Burman et al., 2008 *J. Biol. Chem;* 283: 17579-17593).

Without wishing to be bound by theory, it is believed that in some embodiments, a complement C3d-binding polypeptide from Sbi of *S. aureus* can be used as an adjuvant to enhance and/or modulate an immune response from an antigen described herein. In some embodiments, the immune response is elicited by a fragment antigen or antigen variant disclosed herein. In some embodiments, the immune response is elicited by a component of Sbi of *S. aureus*.

*S. aureus* Sbi is referenced by Gene ID: 3919725 and NCBI Ref No.: NC_007795.1. A polynucleotide sequence of Sbi is provided herein as SEQ ID NO: 56:

-continued

```
QLDALVAQKDAEKKVAPKVEAPQIQSPQIEKPKVESPKVEVPQIQSPKVE

VPQSKLLGYYQSLKDSFNYGYKYLTDTYKSYKEKYDTAKYYYNTYYKYKG

AIDQTVLTVLGSGSKSYIQPLKVDDKNGYLAKSYAQVRNYVTESINTGKV

LYTFYQNPTLVKTAIKAQETASSIKNTLSNLLSFWK
```

In some embodiments, any of the fusion polypeptides, fusion nucleotides, compositions, methods or uses disclosed herein, comprises a complement C3d-binding polypeptide of Sbi of *S. aureus*. In some embodiments, a Sbi complement C3d binding polypeptide comprises one or both of domain III and domain IV of Sbi, or a functional fragment or a variant thereof.

In some embodiments, a Sbi complement C3d binding polypeptide comprises an amino acid sequence having at

```
   1 atgaaaaata aatatatctc gaagttgcta gttggggcag caacaattac gttagctaca

  61 atgatttcaa atggggaagc aaaagcgagt gaaaacacgc aacaaacttc aactaagcac

 121 caaacaactc aaaacaacta cgtaacagat caacaaaaag ctttttatca agtattacat

 181 ctaaaaggta tcacagaaga acaacgtaac caatacatca aaacattacg cgaacaccca

 241 gaacgtgcac aagaagtatt ctctgaatca cttaaagaca gcaagaaccc agaccgacgt

 301 gttgcacaac aaaacgcttt ttacaatgtt cttaaaaatg ataacttaac tgaacaagaa

 361 aaaaataatt acattgcaca aattaaagaa aaccctgata gaagccaaca agtttgggta

 421 gaatcagtac aatcttctaa agctaaagaa cgtcaaaata ttgaaaatgc ggataaagca

 481 attaaagatt tccaagataa caaagcacca cacgataaat cagcagcata tgaagctaac

 541 tcaaaattac ctaaagattt acgtgataaa aacaaccgct ttgtagaaaa agtttcaatt

 601 gaaaaagcaa tcgttcgtca tgatgagcgt gtgaaatcag caaatgatgc aatctcaaaa

 661 ttaaatgaaa aagattcaat tgaaaacaga cgtttagcac aacgtgaagt taacaaagca

 721 cctatggatg taaaagagca tttacagaaa caattagacg cattagttgc tcaaaaagat

 781 gctgaaaaga aagtggcgcc aaaagttgag gctcctcaaa ttcaatcacc acaaattgaa

 841 aaacctaaag tagaatcacc aaaagttgaa gtccctcaaa ttcaatcacc aaaagttgag

 901 gttcctcaat ctaaattatt aggttactac caatcattaa aagattcatt taactatggt

 961 tacaagtatt taacagatac ttataaaagc tataaagaaa aatatgatac agcaaagtac

1021 tactataata cgtactataa atacaaaggt gcgattgatc aaacagtatt aacagtacta

1081 ggtagtggtt ctaaatctta catccaacca ttgaaagttg atgataaaaa cggctactta

1141 gctaaatcat atgcacaagt aagaaactat gtaactgagt caatcaatac tggtaaagta

1201 ttatatactt tctaccaaaa cccaacatta gtaaaaacag ctattaaagc tcaagaaact

1261 gcatcatcaa tcaaaaatac attaagtaat ttattatcat tctggaaata a
```

A polypeptide sequence of Sbi is provided herein as SEQ ID NO: 57.

```
MKNKYISKLLVGAATITLATMISNGEAKASENTQQTSTKHQTTQNNYVTD

QQKAFYQVLHLKGITEEQRNQYIKTLREHPERAQEVFSESLKDSKNPDRR

VAQQNAFYNVLKNDNLTEQEKNNYIAQIKENPDRSQQVWVESVQSSKAKE

RQNIENADKAIKDFQDNKAPHDKSAAYEANSKLPKDLRDKNNRFVEKVSI

EKAIVRHDERVKSANDAISKLNEKDSIENRRLAQREVNKAPMDVKEHLQK
```

least 80%, 85%, 90%, 91%, 92%, 93%, 94%, 95%, 96%, 97%, or 100% identity to the amino acid sequence of SEQ ID NO: 9. In some embodiments, a Sbi complement C3d binding polypeptide comprises an amino acid sequence having at least 80%, 85%, 90%, 91%, 92%, 93%, 94%, 95%, 96%, 97%, or 100% identity to the amino acid sequence of SEQ ID NO: 10. In some embodiments, a Sbi complement C3d binding polypeptide comprises an amino acid sequence having at least 80%, 85%, 90%, 91%, 92%, 93%, 94%, 95%, 96%, 97%, 98%, 99% or 100% identity to the amino acid sequence of SEQ ID NO: 57.

In some embodiments, a Sbi complement C3d binding polypeptide is encoded by a polynucleotide which encodes an amino acid having at least 80%, 85%, 90%, 91%, 92%, 93%, 94%, 95%, 96%, 97%, or 100% identity to the amino acid sequence of SEQ ID NO: 9. In some embodiments, a Sbi complement C3d binding polypeptide is encoded by a polynucleotide which encodes an amino acid having at least 80%, 85%, 90%, 91%, 92%, 93%, 94%, 95%, 96%, 97%, or 100% identity to the amino acid sequence of SEQ ID NO: 10. In some embodiments, a Sbi complement C3d binding polypeptide is encoded by a polynucleotide which encodes an amino acid having at least 80%, 85%, 90%, 91%, 92%, 93%, 94%, 95%, 96%, 97%, or 100% identity to the amino acid sequence of SEQ ID NO: 56. Due to degeneracy in the genetic code, those of ordinary skill in the art would understand that other DNA sequences (including codon-optimized sequences) could encode these polypeptides, as well as the others disclosed herein.

Fusion Polypeptides

This disclosure provides fusion polypeptides comprising (i) a fragment antigen or antigen variant that comprises an epitope of a target protein antigen; and (ii) a complement C3d-binding polypeptide from an immunoglobulin-binding protein (Sbi) of *Staphylococcus aureus*. Exemplary fusion polypeptides disclosed herein are provided in Tables 1 and 2.

In some embodiments, the fragment antigen, antigen variant or fragment antigen variant has an amino acid sequence at least 80%, 85%, 90%, 91%, 92%, 93%, 94%, 95%, 96%, 97%, 98%, 99% or 100% identity to the amino acid sequence of SEQ ID NO: 3.

In some embodiments, the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 4.

In some embodiments, the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 5.

In some embodiments, the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 6.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 7.

In some embodiments, the fragment antigen, antigen variant or fragment antigen variant has at least 80%, 85%, 90%, or 100% identity to the amino acid sequence of SEQ ID NO: 8.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 20.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 21.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 22.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 23.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 24.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 25.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO:26.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 27.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 28.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 29.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 30.

In some embodiments, the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 31.

In some embodiments, (a) and (b) are contiguous or separated by a linker. In some embodiments, the linker is a peptidyl linker. In some embodiments, the peptidyl linker comprises at least 60% glycine and/or serine. In some embodiments, the linker is chosen from a Gly-Gly-Gly-Gly-Ser (Gly4-Ser) linker (SEQ ID NO: 60), or a Histidine linker. In some embodiments, the linker is a Gly4-Ser linker (SEQ ID NO: 60). In some embodiments, the linker comprises 1, 2, 3, 4, 5, 6, 7, 8, 9, or 10 repeats of the Gly4-Ser linker (SEQ ID NO: 61). In some embodiments, the linker comprises 3 repeats of the Gly4-Ser linker (SEQ ID NO: 11). In some embodiments, the linker comprises the sequence of SEQ ID NO: 11.

In some embodiments, the polypeptide further comprises a secretion peptide. In some embodiments, the secretion peptide is about 10-30 amino acids in length. In some embodiments, the secretion peptide is about 10, 11, 12, 13, 14, 15, 16, 17, 18, 19, 20, 21, 22, 23, 24, 25, 26, 27, 28, 29 or 30 amino acids in length. In some embodiments, the secretion peptide comprises an amino acid having at least 80%, 85%, 90%, or 100% identity to the amino acid sequence of SEQ ID NO: 1. In some embodiments, the secretion peptide comprises an amino acid having at least 80%, 85%, 90%, or 100% identity to the amino acid sequence of SEQ ID NO: 2.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 12.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 13.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 14.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 15.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 16.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 17.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 18.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 19.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 32.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 33.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 34.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:35.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:36.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:37.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:38.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:39.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:40.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:41.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:42.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 43.

In some embodiments, the polypeptide has at least 80%, 85%, 90%, 91%, 92%, 93%, 94%, 95%, 96%, 97%, 98%, 99% or 100% identity to the amino acid sequence of SEQ ID NO: 44.

In some embodiments, the polypeptide has at least 80%, 85%, 90%, 91%, 92%, 93%, 94%, 95%, 96%, 97%, 98%, 99% or 100% identity to the amino acid sequence of SEQ ID NO:45.

TABLE 1

Exemplary amino acid sequences of components of polypeptide fusions disclosed herein

| SEQ ID NO | Feature | Amino acid sequence |
|---|---|---|
| 1 | Human IL-2 secretion peptide | MYRMQLLSCIALSLALVTNS |
| 2 | SARS-CoV-2 Spike residues 1-13 (secretion peptide) | MFVFLVLLPLVSS |
| 3 | SARS-CoV-2 Spike residues 331-527 (RBD domain) | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLDSKVGGNYNYLYRLFRKSNL KPFERDISTEIYQAGSTPCNGVEGFNCYFPLQSY GFQPTNGVGYQPYRVVVLSFELLHAPATVCGP |
| 4 | SARS-CoV-2 Spike residues 410-527(portion of RBD domain) | IAPGQTGKIADYNYKLPDDFTGCVIAWNSNNL DSKVGGNYNYLYRLFRKSNLKPFERDISTEIYQ AGSTPCNGVEGFNCYFPLQSYGFQPTNGVGYQ PYRVVVLSFELLHAPATVCGP |

TABLE 1-continued

Exemplary amino acid sequences of components of polypeptide fusions disclosed herein

| SEQ ID NO | Feature | Amino acid sequence |
|---|---|---|
| 5 | SARS-CoV-2 Spike residues 430-527 (portion of RBD domain) | TGCVIAWNSNNLDSKVGGNYNYLYRLFRKSNL KPFERDISTEIYQAGSTPCNGVEGFNCYFPLQSY GFQPTNGVGYQPYRVVVLSFELLHAPATVCGP |
| 6 | SARS-CoV-2 Spike residues 438-527 (portion of RBD domain) | SNNLDSKVGGNYNYLYRLFRKSNLKPFERDIST EIYQAGSTPCNGVEGFNCYFPLQSYGFQPTNGV GYQPYRVVVLSFELLHAPATVCGP |
| 7 | SARS-CoV-2 Spike residues 480-527 (portion of RBD domain) | CNGVEGFNCYFPLQSYGFQPTNGVGYQPYRVV VLSFELLHAPATVCGP |
| 8 | SARS-CoV-2 Spike residues 528-537 | KKSTNLVKNK |
| 9 | Domain III of Sbi from *S. aureus* strain Mu50 | IENADKAIKDFQDNKAPHDKSAAYEANSKLPK DLRDKNNRFV |
| 10 | Domain IV of Sbi from *S. aureus* strain Mu50 | EKVSIEKAIVRHDERVKSANDAISKLNEKDSIEN RRLAQREVNKAPMDVKEHLQKQLD |
| 11 | Gly4 Ser linker | GGGGSGGGGSGGGGS |
| 20 | SARS-CoV-2 Spike residues 331-527 (RBD domain) - variant 1 | NITNLCPFGEVFNATRFASVYAWNRKRISNCVA DYSVLYNSASFSTFKCYGVSPTKLNDLCFTNVY ADSFVIRGDEVRQIAPGQTGKIADY**N**Y**S**LPDDF TGCVIAWNSNNLDSKVGGNYNYLYRLFRKSNL KPFERDISTEIYQAGSTPCNGVEGFNCYFPLQSY GFQPTNGVGYQPYRVVVLSFELLHAPATVCGP |
| 21 | SARS-CoV-2 Spike residues 331-527 (RBD domain) - variant 2 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSSNLDSKVGGNYNYLYRLFRKSNL KPFERDISTEIYQAGSTPCNGVEGFNCYFPLQSY GFQPTNGVGYQPYRVVVLSFELLHAPATVCGP |
| 22 | SARS-CoV-2 Spike residues 331-527 (RBD domain) - variant 3 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNTDSKVGGNYNYLYRLFRKSNL KPFERDISTEIYQAGSTPCNGVEGFNCYFPLQSY GFQPTNGVGYQPYRVVVLSFELLHAPATVCGP |
| 23 | SARS-CoV-2 Spike residues 331-527 (RBD domain) - variant 4 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLSSKVGGNYNYLYRLFRKSNL KPFERDISTEIYQAGSTPCNGVEGFNCYFPLQSY GFQPTNGVGYQPYRVVVLSFELLHAPATVCGP |
| 24 | SARS-CoV-2 Spike residues 331-527 (RBD domain) - variant 5 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLDSKVGGNYSYLYRLFRKSNL KPFERDISTEIYQAGSTPCNGVEGFNCYFPLQSY GFQPTNGVGYQPYRVVVLSFELLHAPATVCGP |
| 25 | SARS-CoV-2 Spike residues 331-527 (RBD domain) - variant 6 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLDSKVGGNYNYTYRLFRKSNL KPFERDISTEIYQAGSTPCNGVEGFNCYFPLQSY GFQPTNGVGYQPYRVVVLSFELLHAPATVCGP |
| 26 | SARS-CoV-2 Spike residues 331-527 (RBD domain) - variant 7 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLDSKVGGNYNYLYRLFRKSNL SPFERDISTEIYQAGSTPCNGVEGFNCYFPLQSY GFQPTNGVGYQPYRVVVLSFELLHAPATVCGP |

TABLE 1-continued

Exemplary amino acid sequences of components of polypeptide fusions disclosed herein

| SEQ ID NO | Feature | Amino acid sequence |
|---|---|---|
| 27 | SARS-CoV-2 Spike residues 331-527 (RBD domain) - variant 8 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLDSKVGGNYNYLYRLFRKSNL KPFERDISTEIYQAGSTPCNGTEGFNCYFPLQSY GFQPTNGVGYQPYRVVVLSFELLHAPATVCGP |
| 28 | SARS-CoV-2 Spike residues 331-527 (RBD domain) - variant 9 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLDSKVGGNYNYLYRLFRKSNL KPFERDISTEIYQAGSTPCNGVEGFNCTFPLQSY GFQPTNGVGYQPYRVVVLSFELLHAPATVCGP |
| 29 | SARS-CoV-2 Spike residues 331-527 (RBD domain) - variant 10 | NITNLCPFGEVFNATRFASVYAWNRKRISNCVA DYSVLYNSASFSTFKCYGVSPTKLNDLCFTNVY ADSFVIRGDEVRQIAPGQTGKIADYNYKLPDDF TGCVIAWNSNNLDSKVGGNYNYLYRLFRKSNL KPFERDISTEIYQAGSTPCNGVEGFNCYFPLQSY GFQPTNGTGYQPYRVVVLSFELLHAPATVCGP |
| 30 | SARS-CoV-2 Spike residues 331-527 (RBD domain) - variant 11 | NITNLCPFAEVFNATRFASVAAWNAKAISNCV ADYSVLYNSASFSTFKCYGVAPTKLNAACFTN VYADSFVIRGAEVRQIAPGQTGKIADYNYKLPD DFTGCVIAWNSNNLDSKVGGNYNYLYRLFRKS NLKPFERDISTEIYQAGSTPCNGVEGFNCYFPLQ SYGFQPTNGVGYQPYRVVVLSFELLAAPATVC GP |
| 31 | SARS-CoV-2 Spike residues 331-527 (RBD domain) - variant 12 | NITNLCAFGEVFNAARFASVYAWNRKRISNCA AAYSAAYNSASFSAFKCAGVAPTKLNDLCFTA VYADAFAIRAAAVRQAAPAQAGKIADYNYKL PDDFTGCVIAWNSNNLDSKVGGNYNYLYRLFR KSNLKPFERDISTEIYQAGSTPCNGVEGFNCYFP LQSYGFQPTNGVGYQPYRVVVLAFELLHAPAT ACGP |

TABLE 2

Exemplary amino acid sequences of polypeptide fusions encoded by polynucleotide sequences disclosed herein

| SEQ ID NO | Feature | Amino acid sequence |
|---|---|---|
| 12 | IL2(ss)-RBD | MYRMQLLSCIALSLALVTNSAANITNLCPFGEVFNATRFASV YAWNRKRISNCVADYSVLYNSASFSTFKCYGVSPTKLNDLC FTNVYADSFVIRGDEVRQIAPGQTGKIADYNYKLPDDFTGCV IAWNSNNLDSKVGGNYNYLYRLFRKSNLKPFERDISTEIYQA GSTPCNGVEGFNCYFPLQSYGFQPTNGVGYQPYRVVVLSFEL LHAPATVCGPKKSTNLVKNK |
| 13 | IL2(ss)-RBD-Sbi(III-IV) | MYRMQLLSCIALSLALVTNSAANITNLCPFGEVFNATRFASV YAWNRKRISNCVADYSVLYNSASFSTFKCYGVSPTKLNDLC FTNVYADSFVIRGDEVRQIAPGQTGKIADYNYKLPDDFTGCV IAWNSNNLDSKVGGNYNYLYRLFRKSNLKPFERDISTEIYQA GSTPCNGVEGFNCYFPLQSYGFQPTNGVGYQPYRVVVLSFEL LHAPATVCGPKKSTNLVKNKGGGGSGGGGSGGGGSIENAD KAIKDFQDNKAPHDKSAAYEANSKLPKDLRDKNNRFVEKVS IEKAIVRHDERVKSANDAISKLNEKDSIENRRLAQREVNKAP MDVKEHLQKQLD |
| 14 | S(ss)-RBD-Sbi(III-IV) | MFVFLVLLPLVSSAANITNLCPFGEVFNATRFASVYAWNRKR ISNCVADYSVLYNSASFSTFKCYGVSPTKLNDLCFTNVYADS FVIRGDEVRQIAPGQTGKIADYNYKLPDDFTGCVIAWNSNNL DSKVGGNYNYLYRLFRKSNLKPFERDISTEIYQAGSTPCNGV EGFNCYFPLQSYGFQPTNGVGYQPYRVVVLSFELLHAPATV CGPGGGGSGGGGSGGGGSIENADKAIKDFQDNKAPHDKSAA YEANSKLPKDLRDKNNRFVEKVSIEKAIVRHDERVKSANDAI SKLNEKDSIENRRLAQREVNKAPMDVKEHLQKQLD |

TABLE 2-continued

Exemplary amino acid sequences of polypeptide fusions encoded by polynucleotide sequences disclosed herein

| SEQ ID NO | Feature | Amino acid sequence |
|---|---|---|
| 15 | RBDΔ1-Sbi(III-IV) | MYRMQLLSCIALSLALVTNSAAIAPGQTGKIADYNYKLPDDF<br>TGCVIAWNSNNLDSKVGGNYNYLYRLFRKSNLKPFERDISTE<br>IYQAGSTPCNGVEGFNCYFPLQSYGFQPTNGVGYQPYRVVV<br>LSFELLHAPATVCGPKKSTNLVKNKGGGGSGGGGSGGGGSI<br>ENADKAIKDFQDNKAPHDKSAAYEANSKLPKDLRDKNNRF<br>VEKVSIEKAIVRHDERVKSANDAISKLNEKDSIENRRLAQRE<br>VNKAPMDVKEHLQKQLD |
| 16 | RBDΔ2-Sbi(III-IV) | MYRMQLLSCIALSLALVTNSAATGCVIAWNSNNLDSKVGGN<br>YNYLYRLFRKSNLKPFERDISTEIYQAGSTPCNGVEGFNCYFP<br>LQSYGFQPTNGVGYQPYRVVVLSFELLHAPATVCGPKKSTN<br>LVKNKGGGGSGGGGSGGGGSIENADKAIKDFQDNKAPHDK<br>SAAYEANSKLPKDLRDKNNRFVEKVSIEKAIVRHDERVKSA<br>NDAISKLNEKDSIENRRLAQREVNKAPMDVKEHLQKQLD |
| 17 | RBDΔ3-Sbi(III-IV) | MYRMQLLSCIALSLALVTNSAASNNLDSKVGGNYNYLYRLF<br>RKSNLKPFERDISTEIYQAGSTPCNGVEGFNCYFPLQSYGFQP<br>TNGVGYQPYRVVVLSFELLHAPATVCGPKKSTNLVKNKGG<br>GGSGGGGSGGGGSIENADKAIKDFQDNKAPHDKSAAYEANS<br>KLPKDLRDKNNRFVEKVSIEKAIVRHDERVKSANDAISKLNE<br>KDSIENRRLAQREVNKAPMDVKEHLQKQLD |
| 18 | RBDΔ4-Sbi(III-IV) | MYRMQLLSCIALSLALVTNSAACNGVEGFNCYFPLQSYGFQ<br>PTNGVGYQPYRVVVLSFELLHAPATVCGPKKSTNLVKNKGG<br>GGSGGGGSGGGGSIENADKAIKDFQDNKAPHDKSAAYEANS<br>KLPKDLRDKNNRFVEKVSIEKAIVRHDERVKSANDAISKLNE<br>KDSIENRRLAQREVNKAPMDVKEHLQKQLD |
| 19 | RBDΔ5-Sbi(III-IV) | MYRMQLLSCIALSLALVTNSAATNVYADSFVIRGDEVRQIAP<br>GQTGKIADYNYKLPDDFTGCVIAWNSNNLDSKVGGNYNYL<br>YRLFRKSNLKPFERDISTEIYQAGSTPCNGVEGFNCYFPLQSY<br>GFQPTNGVGYQPYRVVVLSFELKKSTNLVKNKGGGGSGGG<br>GSGGGGSIENADKAIKDFQDNKAPHDKSAAYEANSKLPKDL<br>RDKNNRFVEKVSIEKAIVRHDERVKSANDAISKLNEKDSIEN<br>RRLAQREVNKAPMDVKEHLQKQLD |
| 32 | S(ss)-RBD-1 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYSLPDDFTGCVIAWNSNNL<br>DSKVGGNYNYLYRLFRKSNLKPFERDISTEIYQAGSTPCNGV<br>EGFNCYFPLQSYGFQPTNGVGYQPYRVVVLSFELLHAPATV<br>CGP |
| 33 | S(ss)-RBD-2 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYKLPDDFTGCVIAWNSSNL<br>DSKVGGNYNYLYRLFRKSNLKPFERDISTEIYQAGSTPCNGV<br>EGFNCYFPLQSYGFQPTNGVGYQPYRVVVLSFELLHAPATV<br>CGP |
| 34 | S(ss)-RBD-3 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYKLPDDFTGCVIAWNSNNT<br>DSKVGGNYNYLYRLFRKSNLKPFERDISTEIYQAGSTPCNGV<br>EGFNCYFPLQSYGFQPTNGVGYQPYRVVVLSFELLHAPATV<br>CGP |
| 35 | S(ss)-RBD-4 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYKLPDDFTGCVIAWNSNNL<br>SSKVGGNYNYLYRLFRKSNLKPFERDISTEIYQAGSTPCNGV<br>EGFNCYFPLQSYGFQPTNGVGYQPYRVVVLSFELLHAPATV<br>CGP |
| 36 | S(ss)-RBD-5 | MFVFLVLLPLVSSAANITNLCPFGEVFNATRFASVYAWNRKR<br>ISNCVADYSVLYNSASFSTFKCYGVSPTKLNDLCFTNVYADS<br>FVIRGDEVRQIAPGQTGKIADYNYKLPDDFTGCVIAWNSNNL<br>DSKVGGNYSYLYRLFRKSNLKPFERDISTEIYQAGSTPCNGV<br>EGFNCYFPLQSYGFQPTNGVGYQPYRVVVLSFELLHAPATV<br>CGP |

TABLE 2-continued

Exemplary amino acid sequences of polypeptide fusions encoded by polynucleotide sequences disclosed herein

| SEQ ID NO | Feature | Amino acid sequence |
|---|---|---|
| 37 | S(ss)-RBD-6 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYTYRLFRKSNLKPFERDISTEIYQAGSTPCNGVEGFNCYFPLQSYGFQPTNGVGYQPYRVVVLSFELLHAPATVCGP |
| 38 | S(ss)-RBD-7 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLSPFERDISTEIYQAGSTPCNGVEGFNCYFPLQSYGFQPTNGVGYQPYRVVVLSFELLHAPATVCGP |
| 39 | S(ss)-RBD-8 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGTEGFNCYFPLQSYGFQPTNGVGYQPYRVVVLSFELLHAPATVCGP |
| 40 | S(ss)-RBD-9 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGVEGFNCTFPLQSYGFQPTNGVGYQPYRVVVLSFELLHAPATVCGP |
| 41 | S(ss)-RBD-10 | MFVFLVLLPLVSSAANITNLCPFGEVFNATRFASVYAWNRKRISNCVADYSVLYNSASFSTFKCYGVSPTKLNDLCFTNVYADSFVIRGDEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGTGYQPYRVVVLSFELLHAPATVCGP |
| 42 | S(ss)-RBD-11 | MFVFLVLLPLVSSAANITNLCPFAEVFNATRFASVAAWNAKAISNCVADYSVLYNSASFSTFKCYGVAPTKLNAACFTNVYADSFVIRGAEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLAAPATVCGP |
| 43 | S(ss)-RBD-12 | MFVFLVLLPLVSSAANITNLCAFGEVFNAARFASVYAWNRKRISNCAAAYSAAYNSASFSAFKCAGVAPTKLNDLCFTAVYADAFAIRAAAVRQAAPAQAGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLAFELLHAPATACGP |
| 44 | S(ss)-MERS-CoV Spike RBD-SARS-CoV-2 Spike ACE binding RBD | MFVFLVLLPLVSSAAEGVECDFSPLLSGTPPQVYNFKRLVFTNCNYNLTKLLSLFSVNDFTCSQISPAAIASNCYSSLIL**DSFVIRGDEVRQIAPGQTGKIADYNYKLPDDFTGCVIAWNSNNLDSKVGGNYNYLYRLFRKSNLKPFERDISTEIYQAGSTPCNGVEGFNCYFPLQSYGFQPTNGVGYQPYRVVVLSFELLHAPATVCPK** |
| 45 | S(ss)-SARS-CoV-2 Spike ACE binding RBD-MERS-CoV Spike RBD | MFVFLVLLPLVSSAAEGVECDFSPLLSGTPPQVYNFKRLVFTNCNYNLTKLLSLFSVNDFTCSQISPAAIASNCYSSLILDYFSYPLSMKSDLSVSSAGPISQFNYKQSFSNPTCLILATVPHNLTTITKPLKYSYFNKCSRFLSDDRTEVPQLVNANQY**TPCNGVEGFNCYFPLQSYGFQPTNGVGYQPYRVVVLSFELLHAPATV**CPK |

Fusion Polynucleotide

Among other things, the disclosure provides fusion polynucleotides encoding fusion polypeptides comprising (i) a fragment antigen or antigen variant that comprises an epitope of a target protein antigen; and (ii) a complement C3d-binding polypeptide from an immunoglobulin-binding protein (Sbi) of *Staphylococcus aureus*. Exemplary fusion polynucleotide sequences are provided in Table 3.

In some embodiments, (a) and (b) are encoded by a nucleotide sequence and are disposed in the same nucleotide sequence or in different nucleotide sequences. In some embodiments, (a) is disposed N-terminus of (b). In some embodiments, (a) is disposed C-terminus of (b).

In some embodiments, (a) is disposed C-terminus of (b). In some embodiments, (a) and (b) are contiguous or separated by a nucleotide sequence encoding a linker. In some embodiments, the linker is a peptidyl linker. In some embodiments, the peptidyl linker comprises at least 60% glycine and/or serine. In some embodiments, the linker is chosen from a Gly-Gly-Gly-Gly-Ser (Gly4-Ser) linker, or a Histidine linker.

In some embodiments, a fusion polynucleotide further comprises a nucleotide sequence encoding a secretion peptide.

In some embodiments, a fusion polynucleotide is or comprises RNA. In some embodiments, a fusion polynucleotide is or comprises messenger RNA.

In some embodiments, a fusion polynucleotide is or comprises DNA.

In some embodiments, a fusion polynucleotide encodes a fragment antigen which is characterized in that when expressed in vivo, it binds to a Major Histocompatibility Complex (MHC) molecule. In some embodiments, a MHC molecule is or comprises a MHC I molecule or a MHC II molecule.

In some embodiments, a fusion polynucleotide encodes a fragment antigen which is characterized in that when expressed in vivo, it does not bind to a MHC molecule.

In some embodiments, a fusion polynucleotide encodes a fragment antigen which is characterized in that when expressed in vivo, it folds into a three-dimensional conformation that is substantially identical to the three-dimensional conformation of the fragment antigen as it is in its native position in the target protein antigen.

In some embodiments, a fusion polynucleotide encodes a fragment antigen, antigen variant or fragment antigen variant which further comprises an amino acid sequence from a second target protein antigen.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 46.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 47.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 48.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 49.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 50.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 51.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 52.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 53.

In some embodiments, a fusion polynucleotide has at least 80%, 85%, 90%, 91%, 92%, 93%, 94%, 95%, 96%, 97%, 98%, 99% or 100% identity to the nucleotide sequence of SEQ ID NO: 54.

TABLE 3

Exemplary polynucleotide sequences disclosed herein

| SEQ ID NO | Feature | Nucleic acid sequence |
|---|---|---|
| 46 | IL2(ss)-RBD | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaaatatcacaaatctctgccctttcggggaggtcttcaacgcaacccggttcgcatca<br>gtgtacgcctggaatcgcaaacggatttctaactgtgtagccgattattctgtgctgtacaacagtg<br>ctagtttttctaccttcaaatgttatggagtatccccaaccaagcttaacgatctttgttttacaaacgt<br>ctacgcagacagctttgtcatcaggggggacgaagttcgccaaattgctccagggcagacaggt<br>aaaattgcagactataattacaaactcccagacgacttcaccggctgtgttatcgcttggaacagt<br>aacaatcttgacagcaaggtcggtggcaactataattatctctatcgacttttccgaaaatccaattt<br>gaagccctttgagagggacatttcaaccgaaatataccaggctggatcaactccttgcaatggtgt<br>cgaaggatttaactgttacttccccttgcagagttacgggtttcagccaaccaatggggtggggta<br>tcaaccataccgggtcgttgtattgagtttcgaactgttgcatgctccagcaacagtatgtggtccc<br>aaaaagagtacaaatctggtgaaaaacaaaTAATGATAGACCAGCCTCAAG<br>AACACCCGAATGGAGTCTCTAAGCTACATAATACCAACTT<br>ACACTTTACAAAATGTTGTCCCCCAAAATGTAGCCATTCG<br>TATCTGCTCCTAATAAAAAGAAAGTTTCTTCACATTCT |
| 47 | IL2(ss)-RBD-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaaatatcacaaatctctgccctttcggggaggtcttcaacgcaacccggttcgcatca<br>gtgtacgcctggaatcgcaaacggatttctaactgtgtagccgattattctgtgctgtacaacagtg<br>ctagtttttctaccttcaaatgttatggagtatccccaaccaagcttaacgatctttgttttacaaacgt |

TABLE 3-continued

Exemplary polynucleotide sequences disclosed herein

| SEQ ID NO | Feature | Nucleic acid sequence |
|---|---|---|
| | | ctacgcagacagctttgtcatcagggggacgaagttcgccaaattgctccagggcagacaggt<br>aaaattgcagactataattacaaactcccagacgacttcaccggctgtgttatcgcttggaacagt<br>aacaatcttgacagcaaggtcggtggcaactataattatctctatcgacttttccgaaaatccaattt<br>gaagccctttgagagggacatttcaaccgaaatataccaggctggatcaactccttgcaatggtgt<br>cgaaggatttaactgttacttccccttgcagagttacgggtttcagccaaccaatggggtggggta<br>tcaaccataccgggtcgttgtattgagtttcgaactgttgcatgctccagcaacagtatgtggtccc<br>aaaaagagtacaaatctggtgaaaaacaaaggtgggggtggaagtggtgggggaggctctgg<br>cggaggaggaagcatagagaacgcagataaggccataaaggattttcaggataacaaggccc<br>cccacgacaagtccgccgcatacgaagcaaattccaagttgccaaaggatttgcgagacaaaa<br>acaatcgctttgtagagaaagtttcaattgaaaaagcaattgtaaggcatgacgaacgggtgaag<br>agtgctaacgatgcaataagtaagctgaacgagaaagactcaattgagaaccgaaggttggctc<br>aacgcgaggtcaacaaggcaccaatggacgtgaaagagcatctgcaaaagcaacttgacTA<br>ATGATAGACCAGCCTCAAGAACACCCGAATGGAGTCTCTA<br>AGCTACATAATACCAACTTACACTTTACAAAATGTTGTCC<br>CCCAAAATGTAGCCATTCGTATCTGCTCCTAATAAAAAGA<br>AAGTTTCTTCACATTCT |
| 48 | S(ss)-RBD | CTTGTTCTTTTTGCAGAAGCTCAGAATAAACGCTCAACTTT<br>GGCCACCatgttcgtatttctggtacttctccccttgttagttccgcagcaaatatcaccaatc<br>tttgccctttcggagaggtattcaatgcaactcggtttgcaagtgtgtacgcttggaatcgcaagcg<br>catcagcaattgcgtcgctgattacagtgtgctctataacagtgcatctttctccactttcaagtgtta<br>cggtgttagtccaactaagctgaacgatctttgttttaccaacgtgtacgctgattctttcgtcattcg<br>aggggatgaggtgcgacaaatagcacctgggcaaaccgggaaaatagcagactataattataa<br>gctcccagatgacttcactgggtgcgtaattgcctggaatagcaacaatcttgacagtaaagtag<br>gggaaattacaactatttgtacagattgtttcgcaaatccaatttgaagccatttgagcgcgacat<br>ctctactgagatttatcaggctggcagcactccttgtaacggtgtagaaggctttaactgttatttcc<br>cccttcaatcttatgggtttcagcccaccaatggcgtgggataccagccttatcgcgtcgttgtactt<br>agttttgaactgcttcatgctccagctacagtgtgcggccccTAATGATAGACCAGC<br>CTCAAGAACACCCGAATGGAGTCTCTAAGCTACATAATAC<br>CAACTTACACTTTACAAAATGTTGTCCCCCAAAATGTAGC<br>CATTCGTATCTGCTCCTAATAAAAAGAAAGTTTCTTCACAT<br>TCT |
| 49 | S(ss)-RBD-Sbi(III-IV) | CTTGTTCTTTTTGCAGAAGCTCAGAATAAACGCTCAACTTT<br>GGCCACCatgttcgtatttctggtacttctccccttgttagttccgcagcaaatatcaccaatc<br>tttgccctttcggagaggtattcaatgcaactcggtttgcaagtgtgtacgcttggaatcgcaagcg<br>catcagcaattgcgtcgctgattacagtgtgctctataacagtgcatctttctccactttcaagtgtta<br>cggtgttagtccaactaagctgaacgatctttgttttaccaacgtgtacgctgattctttcgtcattcg<br>aggggatgaggtgcgacaaatagcacctgggcaaaccgggaaaatagcagactataattataa<br>gctcccagatgacttcactgggtgcgtaattgcctggaatagcaacaatcttgacagtaaagtag<br>gggaaattacaactatttgtacagattgtttcgcaaatccaatttgaagccatttgagcgcgacat<br>ctctactgagatttatcaggctggcagcactccttgtaacggtgtagaaggctttaactgttatttcc<br>cccttcaatcttatgggtttcagcccaccaatggcgtgggataccagccttatcgcgtcgttgtactt<br>agttttgaactgcttcatgctccagctacagtgtgcggccccggtgggggtggaagtggtgggg<br>gaggctctggcggaggaggaagcatagagaacgcagataaggccataaaggattttcaggata<br>acaaggcccccccacgacaagtccgccgcatacgaagcaaattccaagttgccaaaggatttgc<br>gagacaaaaacaatcgctttgtagagaaagtttcaattgaaaaagcaattgtaaggcatgacgaa<br>cgggtgaagagtgctaacgatgcaataagtaagctgaacgagaaagactcaattgagaaccga<br>aggttggctcaacgcgaggtcaacaaggcaccaatggacgtgaaagagcatctgcaaaagca<br>acttgacTAATGATAGACCAGCCTCAAGAACACCCGAATGGA<br>GTCTCTAAGCTACATAATACCAACTTACACTTTACAAAAT<br>GTTGTCCCCCAAAATGTAGCCATTCGTATCTGCTCCTAATA<br>AAAAGAAAGTTTCTTCACATTCT |
| 50 | RBDΔ1-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaattgctccagggcagacaggtaaaattgcagactataattacaaactcccagacga<br>cttcaccggctgtgttatcgcttggaacagtaacaatcttgacagcaaggtcggtggcaactataa<br>ttatctctatcgacttttccgaaaatccaatttgaagccctttgagagggacatttcaaccgaaatata<br>ccaggctggatcaactccttgcaatggtgtcgaaggatttaactgttacttccccttgcagagttac<br>gggtttcagccaaccaatggggtggggtatcaaccataccgggtcgttgtattgagtttcgaactg<br>ttgcatgctccagcaacagtatgtggtcccaaaaagagtacaaatctggtgaaaaacaaaggtg<br>ggggtggaagtggtgggggaggctctggcggaggaggaagcatagagaacgcagataagg<br>ccataaaggattttcaggataacaaggcccccccacgacaagtccgccgcatacgaagcaaattc<br>caagttgccaaaggatttgcgagacaaaaacaatcgctttgtagagaaagtttcaattgaaaaag<br>caattgtaaggcatgacgaacgggtgaagagtgctaacgatgcaataagtaagctgaacgaga<br>aagactcaattgagaaccgaaggttggctcaacgcgaggtcaacaaggcaccaatggacgtga<br>aagagcatctgcaaaagcaacttgacTAATGATAGACCAGCCTCAAGAA<br>CACCCGAATGGAGTCTCTAAGCTACATAATACCAACTTAC<br>ACTTTACAAAATGTTGTCCCCCAAAATGTAGCCATTCGTA<br>TCTGCTCCTAATAAAAAGAAAGTTTCTTCACATTCT |

TABLE 3-continued

Exemplary polynucleotide sequences disclosed herein

| SEQ ID NO | Feature | Nucleic acid sequence |
|---|---|---|
| 51 | RBDΔ2-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaaccggctgtgttatcgcttggaacagtaacaatcttgacagcaaggtcggtggcaa<br>ctataattatctctatcgacttttccgaaaatccaatttgaagccctttgagagggacatttcaaccga<br>aatataccaggctggatcaactccttgcaatggtgtcgaaggatttaactgttacttccccttgcag<br>agttacgggtttcagccaaccaatggggtggggtatcaaccataccgggtcgttgtattgagtttc<br>gaactgttgcatgctccagcaacagtatgtggtcccaaaaagagtacaaatctggtgaaaaacaa<br>aggtgggggtggaagtggtgggggaggctctggcggaggaggaagcatagagaacgcagat<br>aaggccataaaggattttcaggataacaaggcccccccacgacaagtccgccgcatacgaagca<br>aattccaagttgccaaaggatttgcgagacaaaaacaatcgctttgtagagaaagtttcaattgaa<br>aaagcaattgtaaggcatgacgaacgggtgaagagtgctaacgatgcaataagtaagctgaac<br>gagaaagactcaattgagaaccgaaggttggctcaacgcgaggtcaacaaggcaccaatgga<br>cgtgaaagagcatctgcaaaagcaacttgacTAATGATAGACCAGCCTCAA<br>GAACACCCGAATGGAGTCTCTAAGCTACATAATACCAACT<br>TACACTTTACAAAATGTTGTCCCCCAAAATGTAGCCATTC<br>GTATCTGCTCCTAATAAAAAGAAAGTTTCTTCACATTCT |
| 52 | RBDΔ3-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaagtaacaatcttgacagcaaggtcggtggcaactataattatctctatcgacttttcc<br>gaaaatccaatttgaagccctttgagagggacatttcaaccgaaatataccaggctggatcaactc<br>cttgcaatggtgtcgaaggatttaactgttacttccccttgcagagttacgggtttcagccaaccaat<br>ggggtggggtatcaaccataccgggtcgttgtattgagtttcgaactgttgcatgctccagcaaca<br>gtatgtggtcccaaaaagagtacaaatctggtgaaaaacaaaggtgggggtggaagtggtggg<br>ggaggctctggcggaggaggaagcatagagaacgcagataaggccataaaggattttcagga<br>taacaaggcccccccacgacaagtccgccgcatacgaagcaaattccaagttgccaaaggatttg<br>cgagacaaaaacaatcgctttgtagagaaagtttcaattgaaaaagcaattgtaaggcatgacga<br>acgggtgaagagtgctaacgatgcaataagtaagctgaacgagaaagactcaattgagaaccg<br>aaggttggctcaacgcgaggtcaacaaggcaccaatggacgtgaaagagcatctgcaaaagc<br>aacttgacTAATGATAGACCAGCCTCAAGAACACCCGAATGGA<br>GTCTCTAAGCTACATAATACCAACTTACACTTTACAAAAT<br>GTTGTCCCCCAAAATGTAGCCATTCGTATCTGCTCCTAATA<br>AAAAGAAAGTTTCTTCACATTCT |
| 53 | RBDΔ4-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcatgcaatggtgtcgaaggatttaactgttacttccccttgcagagttacgggtttcagc<br>caaccaatggggtggggtatcaaccataccgggtcgttgtattgagtttcgaactgttgcatgctc<br>cagcaacagtatgtggtcccaaaaagagtacaaatctggtgaaaaacaaaggtgggggtggaa<br>gtggtgggggaggctctggcggaggaggaagcatagagaacgcagataaggccataaagga<br>ttttcaggataacaaggcccccccacgacaagtccgccgcatacgaagcaaattccaagttgcca<br>aaggatttgcgagacaaaaacaatcgctttgtagagaaagtttcaattgaaaaagcaattgtaagg<br>catgacgaacgggtgaagagtgctaacgatgcaataagtaagctgaacgagaaagactcaatt<br>gagaaccgaaggttggctcaacgcgaggtcaacaaggcaccaatggacgtgaaagagcatct<br>gcaaaagcaacttgacTAATGATAGACCAGCCTCAAGAACACCCG<br>AATGGAGTCTCTAAGCTACATAATACCAACTTACACTTTA<br>CAAAATGTTGTCCCCCAAAATGTAGCCATTCGTATCTGCT<br>CCTAATAAAAAGAAAGTTTCTTCACATTCT |
| 54 | RBDΔ5-Sbi(III-IV) | CTTGTTCTTTTTGCAGAAGCTCAGAATAAACGCTCAACTTT<br>GGCCACCatgtatcgcatgcagttgctgtcctgtattgccctgtctctcgcattggtcactaac<br>tctgccgcaacaaacgtctacgcagacagctttgtcatcagggggacgaagttcgccaaattg<br>ctccagggcagacaggtaaaattgcagactataattacaaactcccagacgacttcaccggctgt<br>gttatcgcttggaacagtaacaatcttgacagcaaggtcggtggcaactataattatctctatcgac<br>ttttccgaaaatccaatttgaagccctttgagagggacatttcaaccgaaatataccaggctggatc<br>aactccttgcaatggtgtcgaaggatttaactgttacttccccttgcagagttacgggtttcagccaa<br>ccaatggggtggggtatcaaccataccgggtcgttgtattgagtttcgaactgggtgggggtgga<br>agtggtgggggaggctctggcggaggaggaagcatagagaacgcagataaggccataaagg<br>attttcaggataacaaggcccccccacgacaagtccgccgcatacgaagcaaattccaagttgcc<br>aaaggatttgcgagacaaaaacaatcgctttgtagagaaagtttcaattgaaaaagcaattgtaag<br>gcatgacgaacgggtgaagagtgctaacgatgcaataagtaagctgaacgagaaagactcaat<br>tgagaaccgaaggttggctcaacgcgaggtcaacaaggcaccaatggacgtgaaagagcatct<br>gcaaaagcaacttgacTAATGATAGACCAGCCTCAAGAACACCCG<br>AATGGAGTCTCTAAGCTACATAATACCAACTTACACTTTA<br>CAAAATGTTGTCCCCCAAAATGTAGCCATTCGTATCTGCT<br>CCTAATAAAAAGAAAGTTTCTTCACATTCT |

mRNA Encoding Polypeptides and Formulations Thereof

Among other things, provided herein are polypeptides and polynucleotides which can be used to stimulate an immune response against an antigen and/or to enhance immunogenicity of an antigen.

In some embodiments, a polypeptide disclosed herein is encoded by a polynucleotide comprising an RNA. In some embodiments, a polynucleotide comprises a messenger RNA.s In some embodiments, a polynucleotide comprising an RNA, e.g., mRNA, is formulated in a lipid nanoparticle (LNP) formulation.

In some embodiments, the disclosure provides an LNP formulation comprising a polynucleotide comprising an RNA, e.g., mRNA, for use in an immunogenic composition.

In some embodiments, an LNP formulation comprising a polynucleotide comprising an RNA, e.g., mRNA, is administered to a subject to enhance and/or modulate an immune response. In some embodiments, the immune response is elicited by an antigen comprised in the polynucleotide.

In some embodiments, an LNP formulation comprising a polynucleotide comprising an RNA, e.g., mRNA, is characterized in that when administered to a subject, it reduces immunogenicity to an antigen, e.g., an antigen comprised in a polynucleotide or an antigen comprised in a polypeptide.

In some embodiments, an LNP formulation comprising a polynucleotide comprising an RNA, e.g., mRNA, is characterized in that when administered to a subject it focuses the immune response on a conserved and/or functional region of an epitope of a target protein antigen.

In some embodiments, an LNP formulation comprising a polynucleotide comprising an RNA, e.g., mRNA, is characterized in that when administered to a subject it improves the breadth and/or efficacy of an immune response in the subject to a target protein antigen.

In some embodiments, an LNP formulation comprising a polynucleotide comprising an RNA, e.g., mRNA, is characterized in that when administered to a subject it results in a humoral response, e.g., a broadly neutralizing humoral response, and/or a T cell mediated response.

In some embodiments, a polypeptide disclosed herein comprises a fusion polypeptide as described herein. In some embodiments, a polynucleotide disclosed herein comprises a fusion polynucleotide as described herein. In some embodiments, a fusion polypeptide is encoded by a fusion polynucleotide comprising an RNA. In some embodiments, a fusion polynucleotide comprises a messenger RNA.

In some embodiments, a fusion polynucleotide comprising an RNA, e.g., mRNA, is formulated in a lipid nanoparticle (LNP) formulation.

In some embodiments, the disclosure provides an LNP formulation comprising a fusion polynucleotide comprising an RNA, e.g., mRNA, for use in an immunogenic composition.

In some embodiments, an LNP formulation comprising a fusion polynucleotide comprising an RNA, e.g., mRNA, is administered to a subject to enhance and/or modulate an immune response. In some embodiments, the immune response is elicited by a fragment antigen comprised in a fusion polynucleotide. In some embodiments, the immune response is enhanced by an adjuvant, e.g., C3d binding polypeptide, comprised in a fusion polynucleotide.

In some embodiments, an LNP formulation comprising a fusion polynucleotide comprising an RNA, e.g., mRNA, is characterized in that when administered to a subject, it reduces immunogenicity to an antigen, e.g., an antigen comprised in a fusion polynucleotide or an antigen comprised in a fusion polypeptide.

In some embodiments, an LNP formulation comprising a fusion polynucleotide comprising an RNA, e.g., mRNA, is characterized in that when administered to a subject it focuses the immune response on a conserved and/or functional region of an epitope of a target protein antigen.

In some embodiments, an LNP formulation comprising a fusion polynucleotide comprising an RNA, e.g., mRNA, is characterized in that when administered to a subject it improves the breadth and/or efficacy of an immune response in the subject to a target protein antigen.

In some embodiments, an LNP formulation comprising a fusion polynucleotide comprising an RNA, e.g., mRNA, is characterized in that when administered to a subject it results in a humoral response, e.g., a broadly neutralizing humoral response, and/or a T cell mediated response.

Compositions

Among other things, the present disclosure provides compositions. Compositions disclosed herein, e.g., compositions comprising a polypeptide or a polynucleotide disclosed herein, can focus the immune response on conserved and/or functional regions of an antigen. In some embodiments, this immunofocusing can improve the breadth and/or efficacy of an immune response against an antigen.

In some embodiments, a composition disclosed herein is characterized in that when administered to a subject, it reduces immunogenicity to an antigen, e.g., an antigen comprised in a fusion polynucleotide or an antigen comprised in a fusion polypeptide.

In some embodiments, a composition disclosed herein is characterized in that when administered to a subject it focuses the immune response on a conserved and/or functional region of an epitope of a target protein antigen.

In some embodiments, a composition disclosed herein is characterized in that when administered to a subject it improves the breadth and/or efficacy of an immune response in the subject to a target protein antigen.

In some embodiments, a composition disclosed herein is characterized in that when administered to a subject it results in a humoral response, e.g., a broadly neutralizing humoral response, and/or a T cell mediated response.

In some embodiments, a composition comprises a polypeptide as described herein, e.g., a fusion polypeptide as described herein. In some embodiments, a composition comprises a polynucleotide, e.g., a fusion polynucleotide as described herein.

In some embodiments, a composition is or comprises a pharmaceutical composition, e.g., as described herein.

In some embodiments, a composition is or comprises an expression vector comprising a polynucleotide disclosed herein, e.g., a fusion polynucleotide disclosed herein.

In some embodiments, a composition is or comprises an immunogenic composition, e.g., as described herein.

Immunogenic Compositions

Disclosed herein are immunogenic compositions comprising (1) an antigen fragment or an antigen variant comprising an epitope of a target protein antigen; and/or (2) an adjuvant comprising a complement C3d-binding region. In some embodiments, an immunogenic composition disclosed herein can enhance the titers of the resulting antibody response and/or result in a measurable T cell response.

In some embodiments, an immunogenic composition comprises an immunoglobulin-binding protein (Sbi) of *Staphylococcus aureus* for use as an adjuvant. In some embodiments, an immunogenic composition comprising Sbi for use as an adjuvant comprises an Sbi polypeptide or a fragment thereof. In some embodiments, an immunogenic composition comprising Sbi for use as an adjuvant comprises a polynucleotide encoding an Sbi polypeptide or a fragment thereof.

In some embodiments, an immunogenic composition comprises an antigen fragment or an antigen variant comprising an epitope of a target protein antigen, and an adjuvant comprising a complement C3d-binding polypeptide.

In some embodiments, an immunogenic composition comprises a fusion polypeptide comprising an antigen fragment or an antigen variant comprising an epitope of a target protein antigen fused to a complement C3d-binding polypeptide. In some embodiments, the C3d binding polypeptide comprises an immunoglobulin-binding protein (Sbi) of *Staphylococcus aureus*. In some embodiments, the complement C3d-binding polypeptide is or comprises one or both of domain III and domain IV of the Sbi of *Staphylococcus aureus*, or a functional fragment or a variant thereof.

In some embodiments, an immunogenic composition comprises a fusion polynucleotide encoding a fusion polypeptide comprising an antigen fragment or an antigen variant comprising an epitope of a target protein antigen fused to a complement C3d-binding polypeptide. In some embodiments, the fusion polynucleotide comprises a C3d binding polypeptide comprising an immunoglobulin-binding protein (Sbi) of *Staphylococcus aureus*. In some embodiments, the complement C3d-binding polypeptide is or comprises one or both of domain III and domain IV of the Sbi of *Staphylococcus aureus*, or a functional fragment or a variant thereof.

In some embodiments, an immunogenic composition comprises an expression vector comprising a polynucleotide or a fusion polynucleotide disclosed herein.

Pharmaceutical Compositions

Pharmaceutical compositions of the present disclosure may comprise a polypeptides disclosed herein (e.g., a fusion polypeptide), a polynucleotide disclosed herein (e.g., a fusion polynucleotide), or an expression vector comprising a polynucleotide (e.g., a fusion polynucleotide). In some embodiments, a pharmaceutical composition may comprise a pharmaceutically acceptable excipient, a diluent, or a combination thereof. In some embodiments, a pharmaceutical composition may comprise buffers such as neutral buffered saline, phosphate buffered saline and the like; carbohydrates such as glucose, mannose, sucrose, or dextrans; mannitol; proteins; polypeptides or amino acids such as glycine; antioxidants; chelating agents such as EDTA or glutathione; and preservatives.

In some embodiments, a pharmaceutical composition is formulated for administration according to any of the routes of administration disclosed herein. In some embodiments, a pharmaceutical composition is formulated for intramuscular administration, intradermal administration, intravenous administration, or subcutaneous administration.

Methods of Using Compositions Disclosed Herein

The disclosure provides, among other things, methods for using a fusion polypeptide described herein, a fusion polynucleotide described herein, or a composition comprising the same to stimulate an immune response against an antigen (e.g., as a vaccine), or to enhance immunogenicity of an antigen.

Also disclosed herein, are methods of using a fusion polypeptide described herein, a fusion polynucleotide described herein, or a composition comprising the same to treat a disease or ameliorating a symptom of a disease, e.g., a disease associated with an antigen described herein.

Use of compositions disclosed herein, e.g., compositions comprising a fusion polypeptide or a fusion polynucleotide disclosed herein, can focus the immune response on conserved and/or functional regions of an antigen. In some embodiments, this immunofocusing can improve the breadth and/or efficacy of an immune response against the antigen.

In some embodiments, a method comprising administering a composition disclosed herein results in reduced immunogenicity to an antigen, e.g., an antigen comprised in a the fusion polynucleotide or an antigen comprised in a fusion polypeptide.

In some embodiments, a method comprising administering a composition disclosed herein results in focusing of an immune response on a conserved and/or functional region of an epitope of a target protein antigen.

In some embodiments, a method comprising administering a composition disclosed herein results in improved breadth and/or efficacy of an immune response in a subject to a target protein antigen.

In some embodiments, a method comprising administering a composition disclosed herein results in a humoral response, e.g., a broadly neutralizing humoral response, and/or a T cell mediated response.

This disclosure provides a method comprising administering to a subject in need thereof at least one dose of a pharmaceutical composition comprising a fusion polypeptide disclosed herein, a fusion polynucleotide disclosed herein, or an expression vector comprising a fusion polynucleotide disclosed herein. In some embodiments, the at least one dose is administered in an effective amount to induce an immune response against the fragment antigen in the subject.

Disclosed herein is a method comprising administering to a subject: a first dose of a pharmaceutical composition disclosed herein; and a second dose of a pharmaceutical composition disclosed herein. In some embodiments, a pharmaceutical composition comprises a fusion polypeptide disclosed herein, a fusion polynucleotide disclosed herein, or an expression vector comprising a fusion polynucleotide disclosed herein.

In some embodiments, a first dose and a second dose are administered by at least 3 days, 4 days, 5 days, 6 days, 7 days, 2 weeks, 3 weeks, or 4 weeks apart.

In some embodiments, a first dose and a second dose are in the same amount. In some embodiments, a first dose and a second dose are in different amounts.

This disclosure provides, a method for enhancing the immunogenicity of an antigen, comprising administering to a subject in need thereof, a fusion polypeptide disclosed herein, or a fusion polynucleotide disclosed herein, or a pharmaceutical composition disclosed herein.

This disclosure also provides a method for stimulating an immune response against an antigen, comprising administering to a subject in need thereof, a fusion polypeptide disclosed herein, or a fusion polynucleotide disclosed herein, or a pharmaceutical composition disclosed herein.

Additionally provided herein is a method of treating a disease or ameliorating a symptom of a disease comprising administering to a subject in need thereof, a fusion polypeptide disclosed herein, or a fusion polynucleotide disclosed herein, or a pharmaceutical composition disclosed herein.

In some embodiments of any of the methods disclosed herein, a subject in need thereof is a subject who is suffering from or is susceptible to a disease, disorder, or condition induced by the target protein antigen. In some embodiments, a subject is a mammalian subject. In some embodiments, a subject is a human subject.

In some embodiments of any of the methods or uses disclosed herein, a single dose of the fusion polypeptide, fusion polynucleotide or pharmaceutical composition is administered. In some embodiments of any of the methods or uses disclosed herein, a plurality of doses of the fusion polypeptide, fusion polynucleotide or pharmaceutical composition is administered.

In some embodiments of any of the methods or uses disclosed herein, the fusion polypeptide, fusion polynucleotide or pharmaceutical composition is administered at a dose of about 0.5 micrograms to 10 micrograms.

In some embodiments of any of the methods or uses disclosed herein, administration of the fusion polynucleotide, fusion polypeptide or pharmaceutical composition results in a humoral response. In some embodiments, the humoral response is an antibody response.

In some embodiments of any of the methods or uses disclosed herein, administration of the fusion polynucleotide, fusion polypeptide or pharmaceutical composition results in an increased titer of an antibody response. In some embodiments, the increase in titer is an increase of about 10 fold to about 500 fold. In some embodiments, the increased titer of the antibody response is compared to administration of an otherwise similar fusion polynucleotide that does not comprise an Sbi domain III, or a fragment or variant thereof; and Sbi domain IV, or a fragment or a variant thereof. In some embodiments, the increased titer of the antibody response is compared to administration of an otherwise similar fusion polypeptide that does not comprise an Sbi domain III, or a fragment or variant thereof; and an Sbi domain IV, or a fragment or a variant thereof. In some embodiments, the increased titer of the antibody response is compared to administration of an otherwise similar pharmaceutical composition that does not comprise a nucleotide sequence encoding Sbi domain III, or a fragment or variant thereof; and Sbi domain IV, or a fragment or a variant thereof.

In some embodiments of any of the methods or uses disclosed herein, the composition is administered via any one of the following routes of administration: intramuscular, intravenous, subcutaneous, intrathecal, intradermal, ocular, intranasal, sublingual, or oral.

Method of Screening for Fragment Antigen

Also provided herein is an in vitro method of selecting a fragment antigen by identifying a polypeptide fragment that folds into a three-dimensional conformation that is substantially identical to the three-dimensional conformation as in a target protein antigen from which the fragment is derived. In some embodiments, a screening method disclosed herein can identify an antigen or a fragment antigen which extend the design space of effective antigens. In some embodiments, a screening method disclosed herein can identify an antigen or a fragment antigen that lacks a T cell epitope, or that has a portion of a T cell epitope. In some embodiments, a screening method disclosed herein can identify a fragment antigen which contains only a portion of an epitope of a target protein antigen.

In some embodiments, the method comprises the steps of: providing a mammalian cell display system that displays a library of fragment antigen candidates on cell surface; exposing the mammalian cell display system to a composition comprising antibodies that bind to a target protein antigen from which the fragment antigen candidates are derived; detecting fragment antigen candidates that bind to the target protein antigen-binding antibodies, wherein the binding of a fragment antigen candidate that binds to at least one of the target protein antigen-binding antibodies is indicative of its likelihood to fold into a three-dimensional conformation that is substantially identical to the three-dimensional conformation as in the target protein antigen.

In some embodiments, the method further comprises a step of generating antibodies that bind to the target protein antigen. In some embodiments, the generation of the antibodies comprises (i) immunizing animals with a target protein antigen or a polynucleotide encoding the same from which the fragment antigen candidates are derived; and (ii) identifying antibodies that bind to the target protein antigen.

In some embodiments, the mammalian cell display system comprises HEK293T cells, HeLa cells, or CHO cells.

In some embodiments, the polypeptide fragment is identified based on binding affinity to the antibody in a serum binding assay or a similar assay.

Other features of the invention will become apparent in the course of the following descriptions of exemplary embodiments, which are given for illustration of the invention and are not intended to be limiting thereof.

EXEMPLIFICATION

Example 1: Enhanced Antigenicity of SARS-CoV-2 S Protein Domains with Sbi(III-IV) Fusions This Example describes development of vaccines comprising fragment antigens that focus the immune response on particular regions of an antigen, e.g., conserved and/or functionally critical regions. Immunofocusing in this manner can improve the breadth and efficacy of the vaccine. Among other things, there are two technical challenges for vaccinating with antigens smaller than a protein or a protein subdomain (e.g., a fragment antigen). First, a fragment antigen needs to contain peptides that are efficiently presented on MHC complexes. Second, a fragment antigen must have epitopes folded into the same conformation as in the full protein.

BALB/c mice were administered a 10 μg dose of IM-delivered mRNA encoding: (1) the RBD domain of SARS-CoV-2 S protein (RBD); (2) RBD fused to the transmembrane domain of S protein (RBD-TM); (3) a fusion protein of the RBD domain of SARS-CoV-2 S protein and Sbi(III-IV); or (4) a fusion protein of the RBD domain of SARS-CoV-2 S protein and Sbi(III-IV) and RBD fused to the transmembrane domain of S protein (RBD-TM). A group of unvaccinated mice served as controls. At day 21 post-vaccination, IgG titers were evaluated in the blood using an ELISA. For evaluating the T cell response, spleens from 5 mice were pooled and plated to 4 wells at 500,000 cells/well. Two wells each were stimulated by either N-terminal or C-terminal S protein peptide pools (PepMix SARS-CoV-2 Spike Glycoprotein mix).

The results demonstrated that vaccinating with a minimal antigen fused to a complement C3d-binding region of Sbi protein from *Staphylococcus aureus* (FIG. 1A) enhanced the titers of the resulting antibody response (FIG. 1B). By screening a large set of antigen presentation architectures, this strategy was extended by co-delivery of Sbi(III-IV)-fused antigen with the same antigen fused to a transmembrane domain (FIG. 1B). In addition to eliciting a humoral response, these mRNA-based vaccines also elicited a IFNγ+ IL2+ polyfunctional CD4+ response (FIG. 1C). It was also observed that fusing peptides as short as 25 residues in length to Sbi(III-IV) enabled them to elicit a meaningful antibody response (FIG. 1D). Without wishing to be bound to any particular theory, C3d can directly activate B cells through Complement Receptor 2 (CR2), and allow for induction of immune responses in the absence of CD4+ T cell signaling. Thus, this scaffold can serve as a synthetic immunological synapse, mimicking natural viral infection to drive a strong and appropriate immune response. Accordingly, in some embodiments, the fusion architecture described herein allows small antigens that lack MHC-presented peptides to elicit a meaningful humoral response.

Figures 2A, 2B:
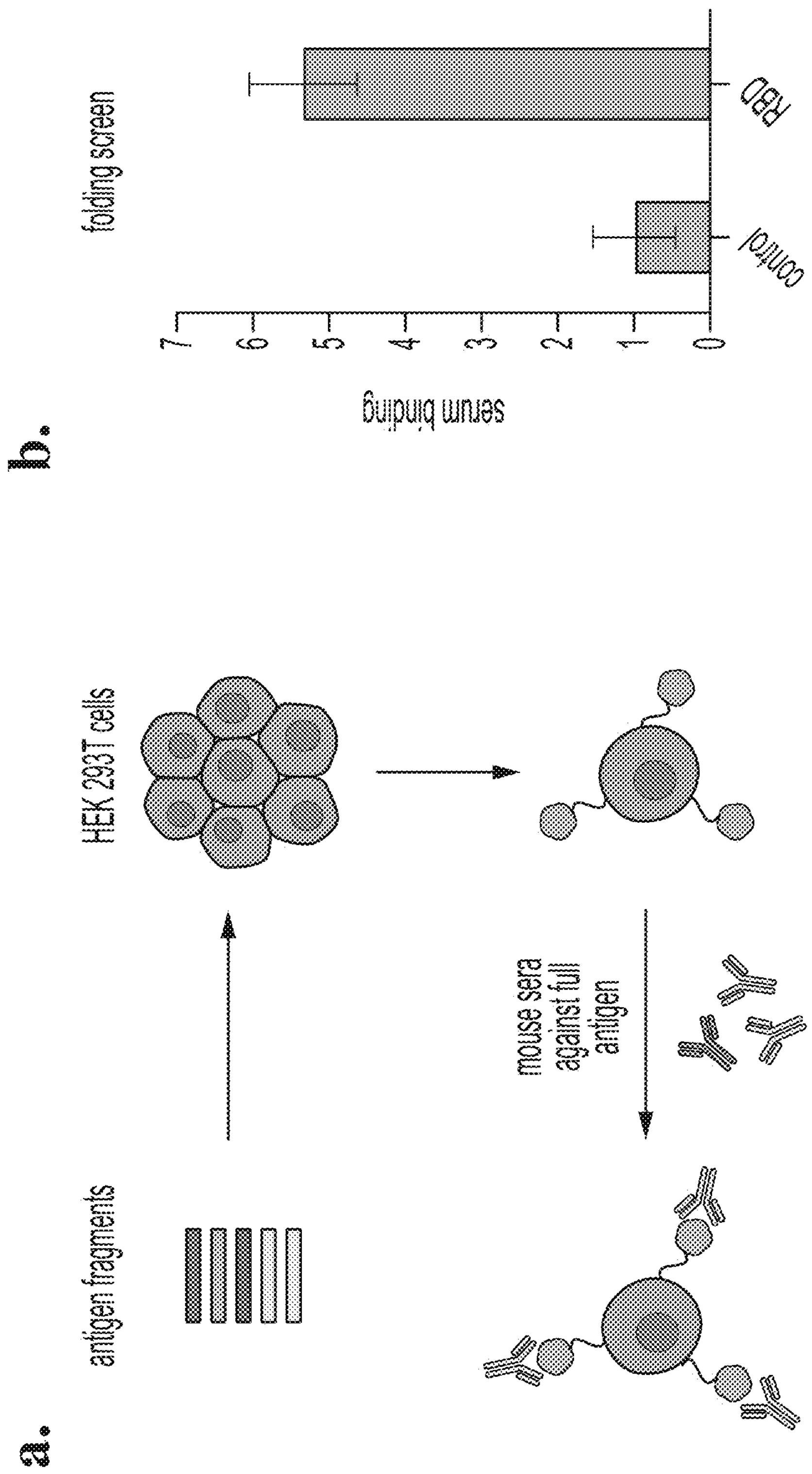
FIGS. 2A-2B depict a high-throughput protein folding screen.

To address the challenge of structure prediction, a high-throughput screen was performed for determining whether a fragment antigen folds into the same three-dimensional conformation as the full protein (FIG. 2A). This screen includes two steps. First, anti-sera against the full protein was generated by vaccinating mice with an mRNA vaccine encoding the full-length protein of interest. The polyclonal antibodies in the sera of the mice were then used as a probe against fragments presented in the context of a mammalian surface display system. As an example, a HEK293T cell expressing a library of antigen fragments can be used in this step. Fragments that bind to antibodies generated by the full protein are likely to share conformational states with the full protein. Correctly folded fragments are identified by an increase in binding to sera antibodies (FIG. 2B). This system allows for the screening of fragments in vitro with two orders of magnitude higher throughput than is practical in vivo.

Example 2: Sbi(III-IV) Fusion to the RBD Domain of SARS-CoV-2 S Protein Increases Virus Neutralization In this Example, virus neutralization activity of serum obtained from mice vaccinated with an mRNA encoding the RBD domain of SARS-CoV-2 S protein, or vaccinated with an mRNA encoding an Sbi(III-IV) fusion to the RBD domain of SARS-CoV-2 S protein was tested.

Figure 3:
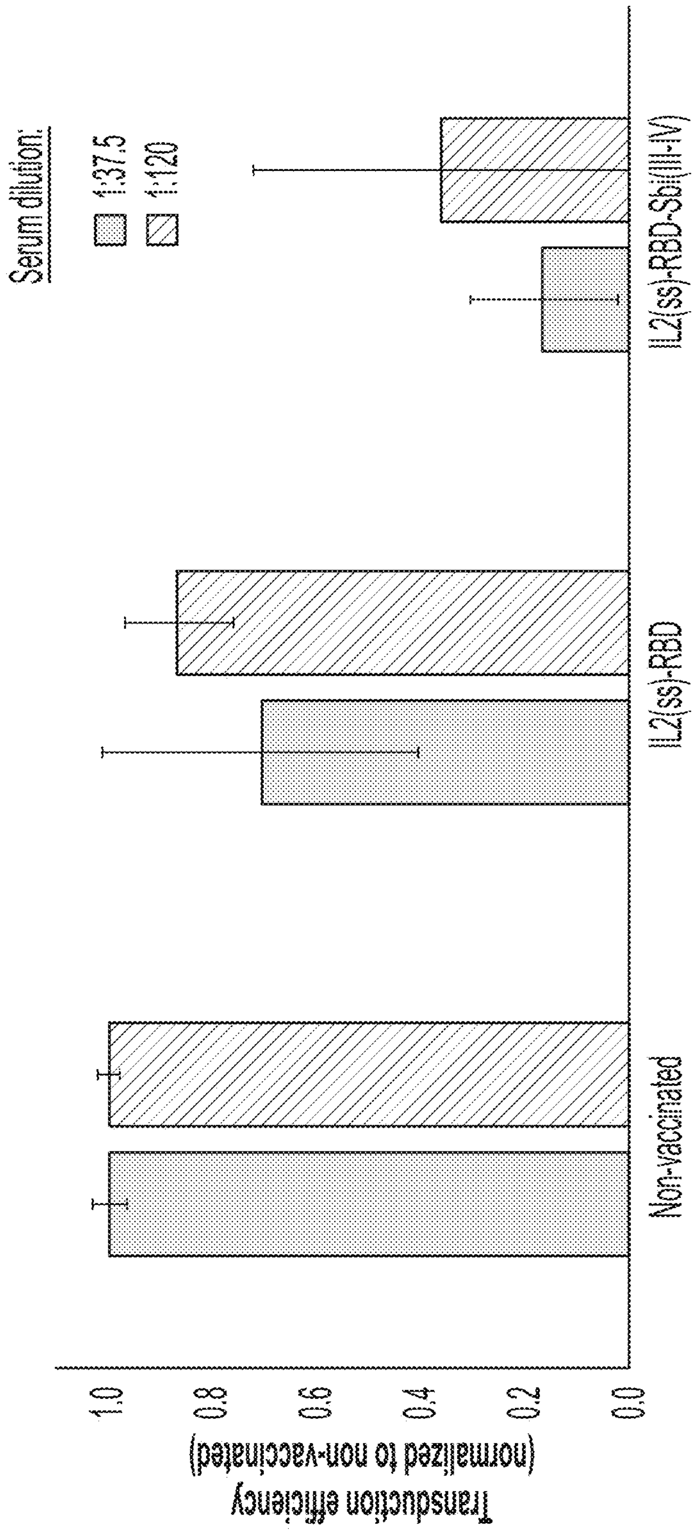
FIG. 3 depicts increased virus neutralization with an Sbi(III-IV) fusion to the RBD domain of SARS-CoV-2 S protein.

For this experiment, BABL/C mice were vaccinated as described in the "animal vaccination" section in Example 6. Specifically, BALB/C mice were injected in the right quadriceps with 50 μL mRNA-LNP formulation (10 μg mRNA dose) of the indicated mRNA constructs. At 10-21 days post-vaccination, serum from vaccinated mice was collected and incubated with target cells in the presence of SARS-CoV-2 virus. Serum from unvaccinated mice was used as a control As shown in FIG. 3, fusing Sbi(III-IV) to the RBD domain of SARS-CoV-2 S protein increases pseudotype virus neutralization compared to the RBD domain of SARS-CoV-2 S protein alone. This effect was observed at both serum dilutions. This data demonstrated that vaccination with mRNA encoding an Sbi(III-IV) fusion to the RBD domain of SARS-CoV-2 S protein results in an antibody response with SARS-CoV-2 virus neutralizing properties.

Example 3: Stimulation of B Cells by an Sbi(III-IV) Fusion to the RBD Domain of SARS-CoV-2 S Protein This Example describes the stimulation of B cells in mice administered a low dose of an mRNA encoding a Sbi(III-IV) fusion to the RBD domain of SARS-CoV-2 S protein.

For this experiment, BABL/C mice were vaccinated as described in the "animal vaccination" section in Example 6. Specifically, mice were vaccinated with a 0.5 ug, 2.5 ug or bug IM-dose of an mRNA comprising a construct having an IL2 secretion peptide and a fusion of the RBD domain of SARS-CoV-2 S protein to Sbi(III-IV), also referred to as IL2(ss)-RBD-Sbi(III-IV). At 10-21 days post-vaccination, blood and spleen were collected from the mice. For titer evaluation, blood from the animals were analyzed with an ELISA assay. For evaluation of T cell responses, an ELISPOT detecting IFNg and/or IL-2 was used.

Figure 4A:
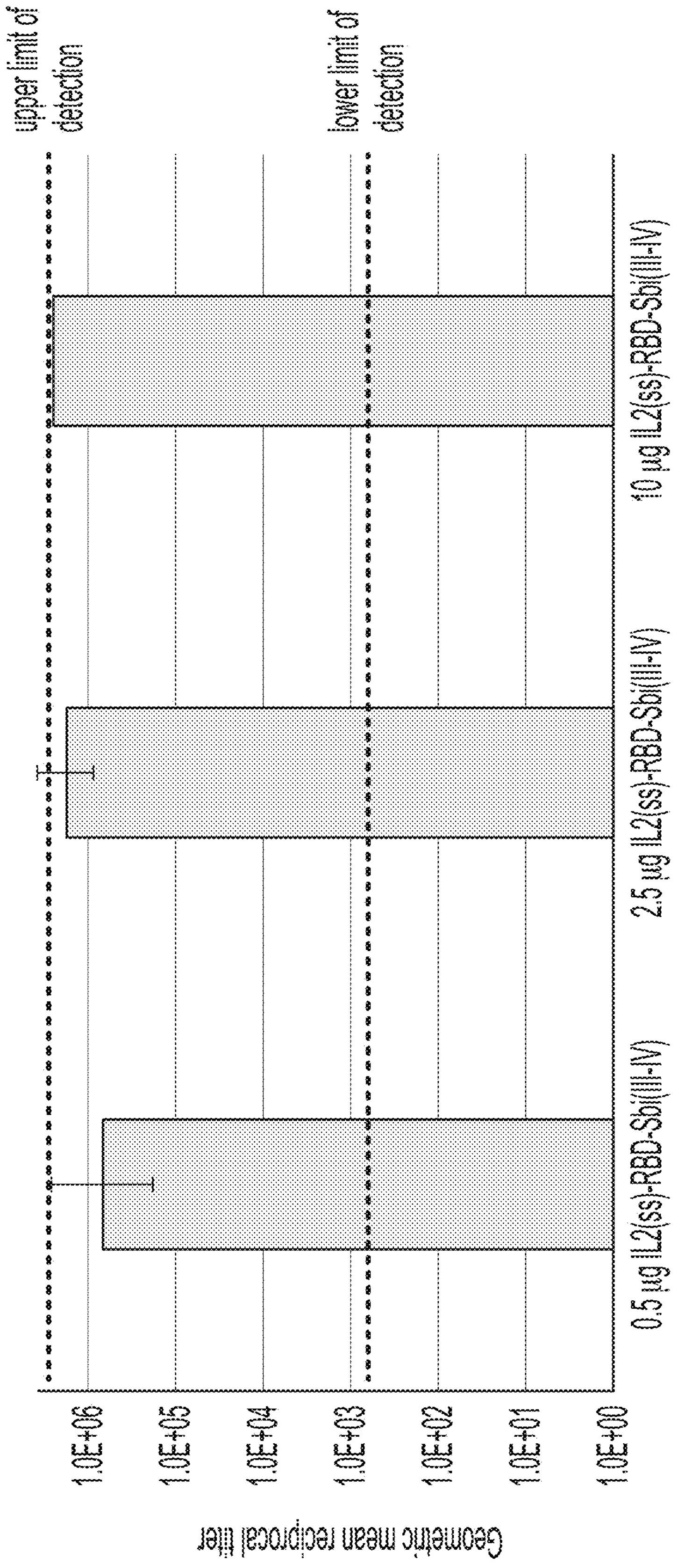
FIGS. 4A-4B depict stimulation of B cells by an Sbi(III-IV) fusion to the RBD domain of SARS-CoV-2 S protein.
Figure 4B:
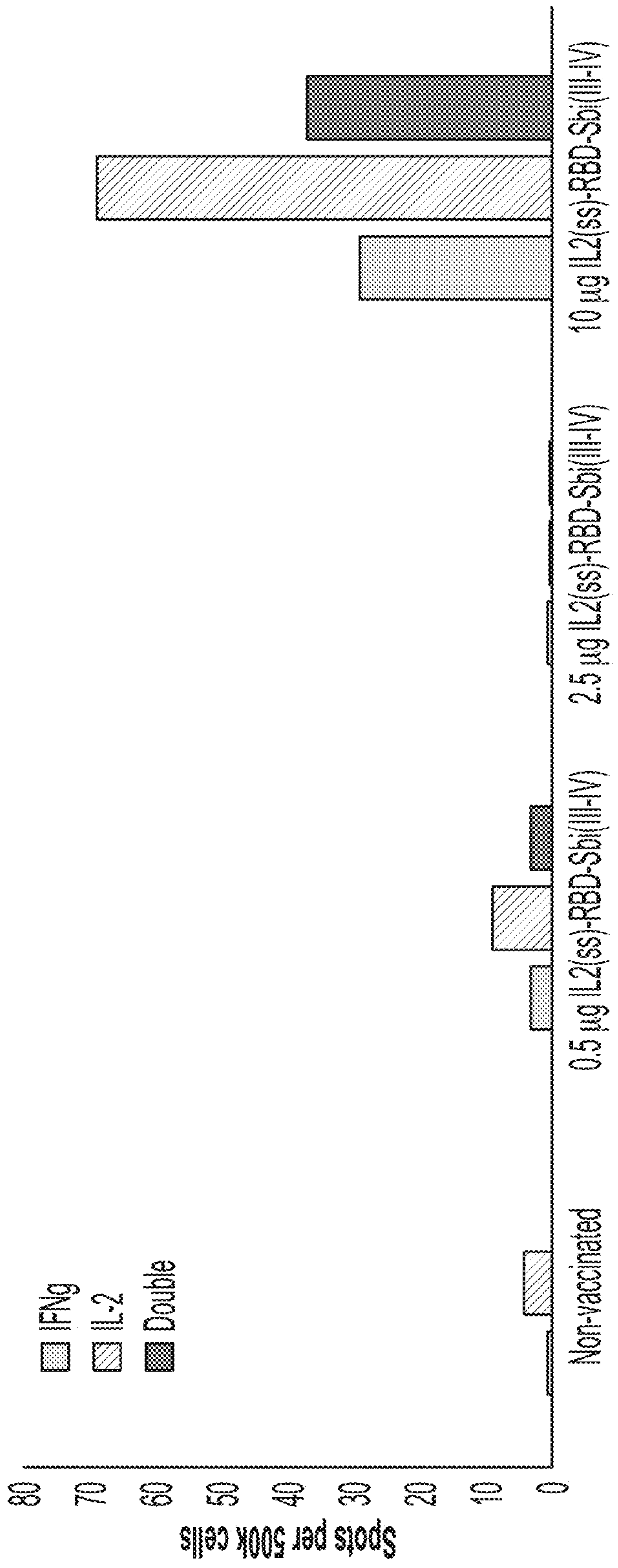

As shown in FIG. 4A, high titers were observed when RBD-Sbi(III-IV) dose was decreased from 10 μg per mouse to 0.5 μg per mouse. Reducing the dose of IL2(ss)-RBD-Sbi(III-IV) below 10 μg reduces the cellular response (FIG. 4B). This data suggested that the antibody response elicited by vaccination with IL2(ss)-RBD-Sbi(III-IV) involves bypassing T cells by directly stimulating B cells.

Example 4: Priming Followed by Boost Increases Antibody Responses Elicited by an Sbi(III-IV) Fusion to the RBD Domain of SARS-CoV-2 S Protein In this Example, the effect of a vaccination regimen comprising a priming dose followed by a booster dose was evaluated.

For this experiment, BABL/C mice were vaccinated as described in the "animal vaccination" section in Example 6. Specifically, mice in 4 groups were injected with a 50 μL mRNA-LNP formulation (10 μg mRNA priming dose) of an mRNA comprising a construct having an IL2 secretion peptide and a fusion of the RBD domain of SARS-CoV-2 S protein to Sbi(III-IV), also referred to as IL2(ss)-RBD-Sbi (III-IV). One group of mice did not receive additional administration of the vaccine (no boost group). The other three groups of mice received a booster dose of 50 μL mRNA-LNP formulation (10 μg mRNA dose) at days 3, 7 and 14 respectively. At 10-21 day post-vaccination, blood and serum was collected from the mice.

Figure 5A:
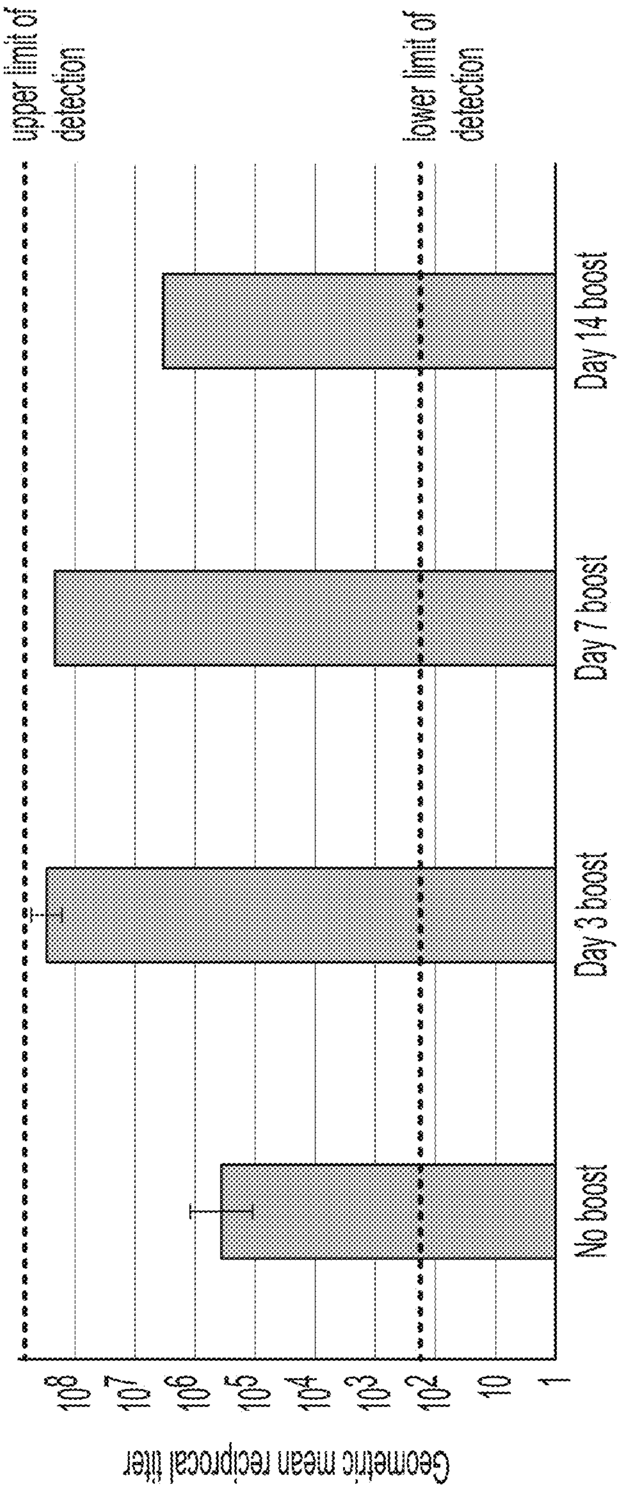
FIGS. 5A-5B depict the results of a vaccination regimen comprising a priming dose and a booster dose.
Figure 5B:
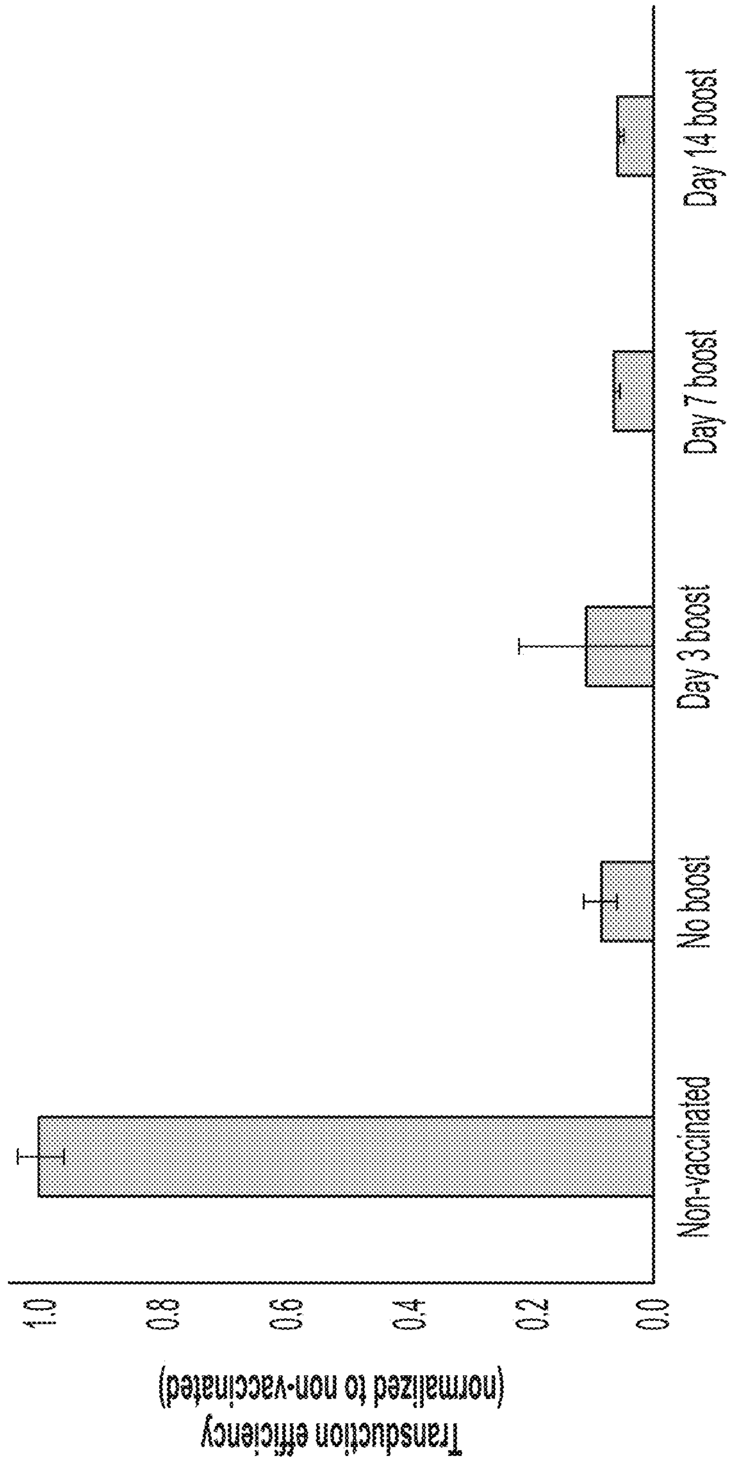

FIG. 5A shows that administration of a booster dose increased the titer generated by IL2(ss)-RBD-Sbi(III-IV) by a factor of >776 (when done on day 3 after the prime), by a factor of >588.1 (when done on day 7 after the prime), and by a factor of >9.2 (when done on day 14 after the prime). FIG. 5B shows that both boosted and prime-only vaccinations were able to block ACE2:RBD interaction in vitro at a 1:20 serum dilution. This data demonstrated that the antibody response elicited by vaccination with IL2(ss)-RBD-Sbi(III-IV) can be enhanced with a vaccination regimen comprising a priming dose and a booster dose.

In the next experiment, the effect of different priming doses was tested. BALB/C mice were injected with a 1 ug or 5 ug priming dose of an mRNA-LNP formulation comprising an mRNA construct having a Spike protein secretion peptide and a fusion of the RBD domain of SARS-CoV-2 S protein to Sbi(III-IV) (S(ss)-RBD-Sbi(III-IV)) or an mRNA comprising a construct having a Spike protein secretion peptide and the RBD domain of SARS-CoV-2 S protein (S(ss)-RBD). The mice received a booster dose on day 4 after priming. At 10-21 day post-vaccination, blood and serum was collected from the mice.

Figure 6A:
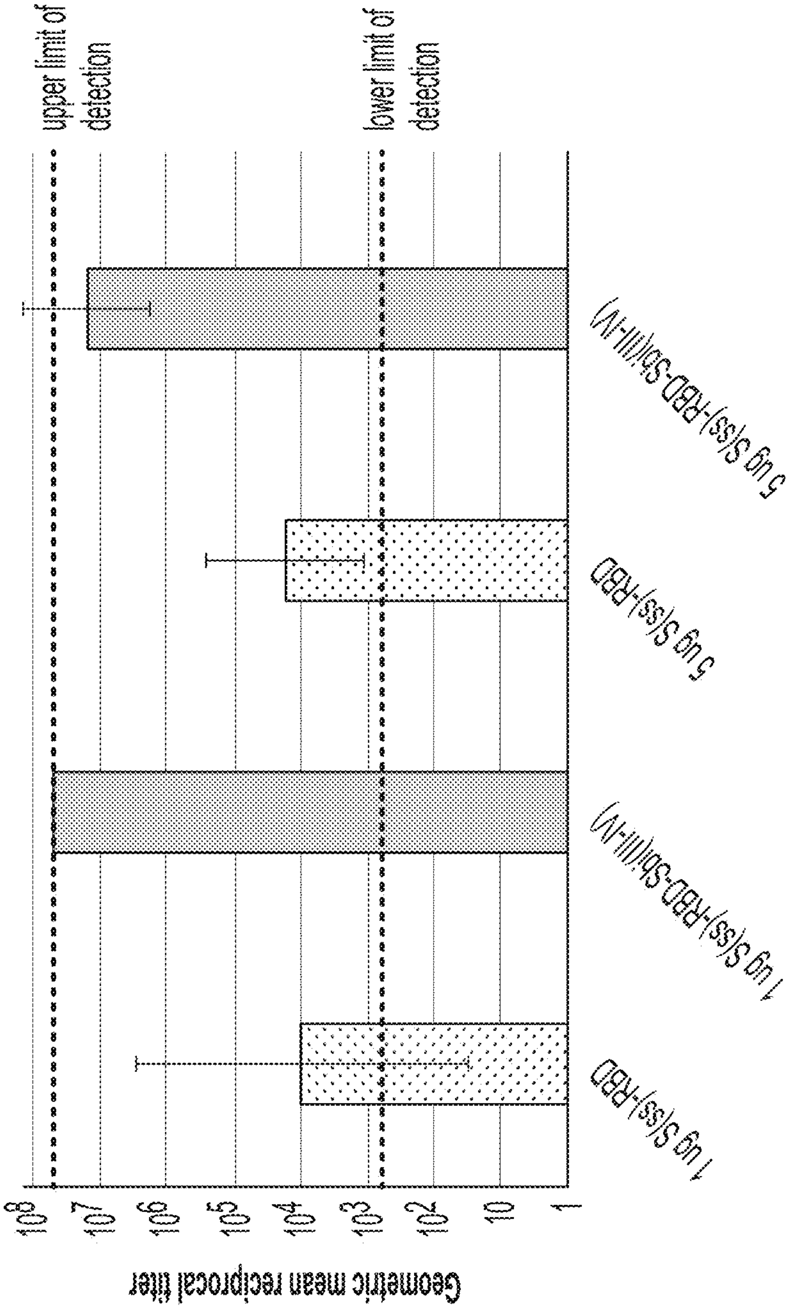
FIG. 6A is a graph showing antibody titer generated with a vaccination regimen comprising a priming dose and a booster dose.

FIG. 6A shows that priming with 1 ug or 5 ug of an mRNA comprising S(ss)-RBD-Sbi(III-IV) resulted in a similar antibody titers. This data demonstrated that a lower priming dose is sufficient to induce an antibody response.

Example 5: Development of a Broad Influenza A Subtype H1N1 Vaccine that is Resistant to HA Antigen Drift This Example describes utilizing methods provided in this disclosure to develop a broad viral (e.g., influenza A subtype H1N1 vaccine) that is resistant to HA antigen drift. This strategy is expected to be broadly applicable. This approach can be extended by building a drift- and shift-resistant vaccine containing precisely designed antigens for all eighteen influenza HA subtypes.

Figure 7A:
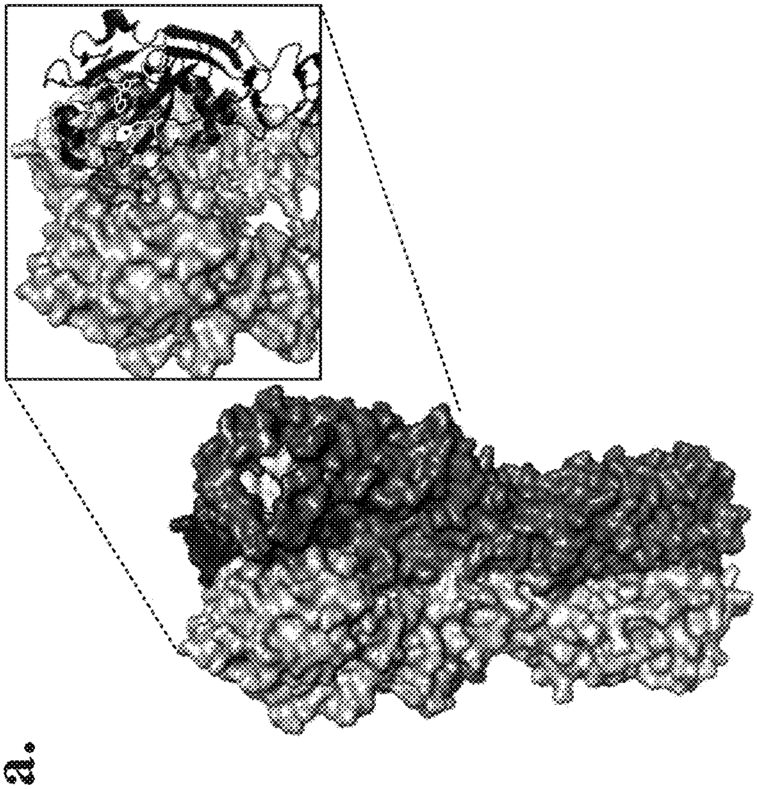
FIGS. 7A-7B depict conserved hemagglutinin HAI residues.
Figure 7B:
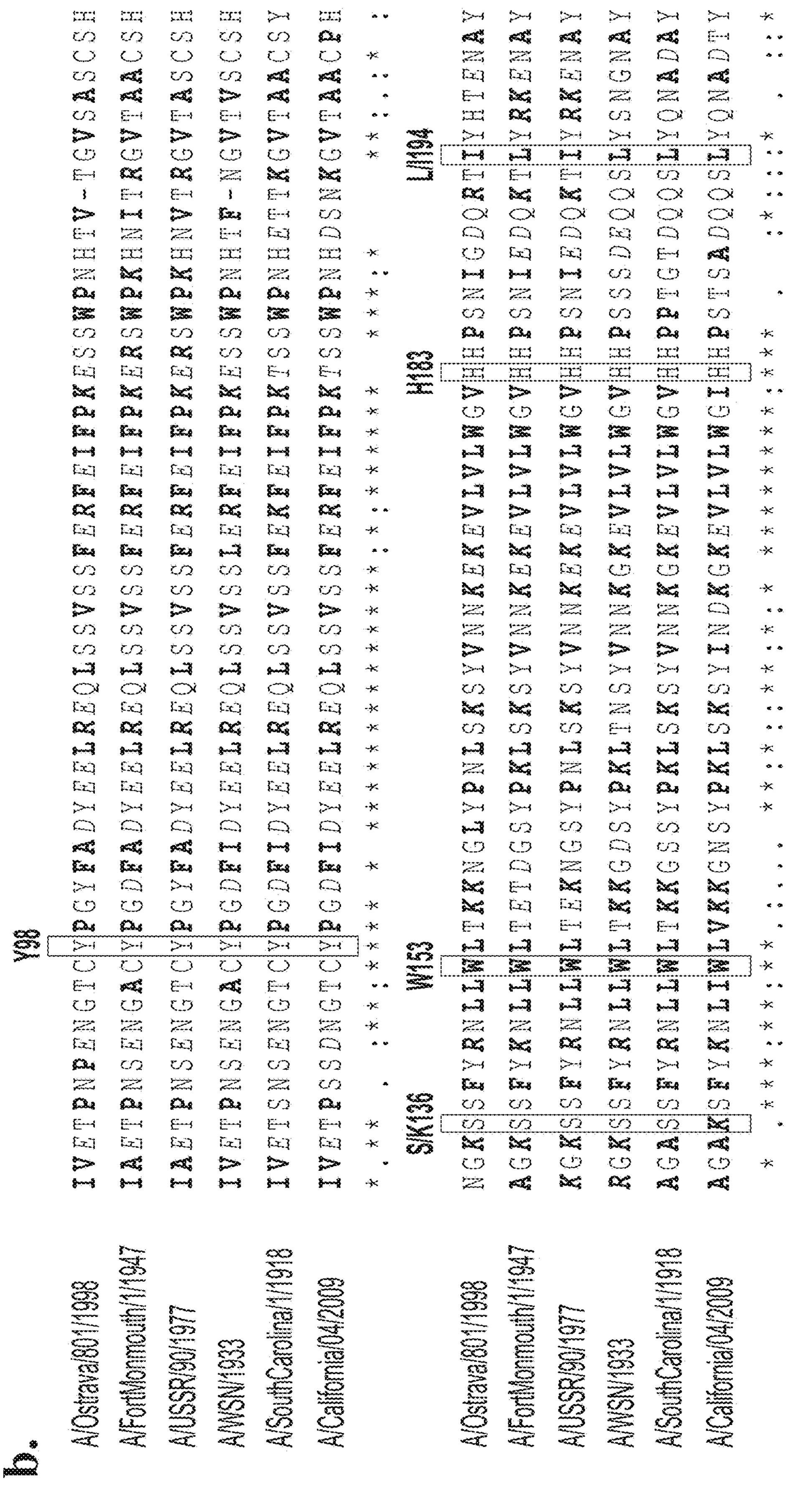

The high throughput folding screen described in Example 2 is used to identify a minimal antigen within the ribosome binding site (RBS) of the hemagglutinin HAI head domain (FIG. 7A). The RBS is essential for receptor binding and is broadly conserved across influenza A H1N1 viruses (FIG. 7B), yet surrounding variable residues often limit the breadth of RBS-directed antibodies (Raymond et al. (2018) *PNAS* 115(1):168-173). The screen is used to identify a minimal foldable RBS which can focus the immune response on the conserved residues.

Example 6: Materials and Methods Used in Examples Disclosed Herein gBlock amplification: Each gBlock template was amplified with T7-AGG_fwd (gaattTAATACGACTCACTATAAGGcttgttcttttgcagaagc) (SEQ ID NO: 62) and 120 pA_rev (TTTTTTTTTTTTTTTTTTTTTTTTTTTTTTTT TTTTTTTTTTTTTTTTTTTTTTTTTTTTTTT TTTTTTTTTTTTTTTTTTTTTTTTTTTTTTTTTTTTT TTTTTTTTTTTTTTTTTTTTagaatgtga agaaactttcttttattag) (SEQ ID NO: 55) using Herculase II polymerase (Agilent) with an annealing temperature of 50° C.

mRNA synthesis: The PCR products were cleaned up using a 0.8× ratio of SPRISelect beads to PCR reaction volume. 19.9 μL transcription mixes consisting of 1× HiScribe T7 High Yield buffer (NEB), 7.5 mM of each NTP, 7.5 mM CleanCap AG (TriLink Biotech), 2M betaine (ThermoSci), 20 mM MgCl2, and 0.1 μL/μL HiScribe T7 Polymerase Mix were added to 2.1 uL DNA solution consisting of 200 ng T7 template in nuclease free H2O. Transcription was carried out for 1 hr at 50° C. The transcribed RNAs were purified using the 500 μg capacity Monarch RNA Cleanup Kit, treated with DNAse I, and purified again using 500 μg-capacity Monarch columns. mRNAs were then treated with Alkaline Phosphatase (Millipore) for 10 min at 37° C. and purified using 500 μg Monarch columns. Concentrations were determined using a NanoDrop spectrophotometer.

LNP formulation: Formulations of mRNA in lipid nanoparticles (mRNA-LNPs) were prepared using the NanoAssemlr Ignite microfluidic mixer (Precision Nanosystems). GenVoy-ILM lipid mixture (Precision Nanosystems) was diluted to 12.5 mM in anhydrous ethanol and combined with an aqueous solution of mRNA (0.14 mg/mL) in PNI buffer (Precision Nanosystems), using the manufacturer-recommended formulation parameters. Formulations were immediately diluted 30:1 in phosphate-buffered saline (pH 7.4) and concentrated using Amicon centrifugation filters (MilliporeSigma UFC901008). Formulations were stored at 4° C. and used for in vivo studies within 14 days.

Animal vaccination: All animal experiments were carried out in accordance with the guidelines set forth by Charles River Accelerator Development Lab (CRADL) and were approved by the CRADL Institutional Animal Care and Use committee. Female BALB/C mice (7-9 weeks old) were purchased from Charles River Laboratories and housed at CRADL. Mice were acclimated for at least 3 days before the initiation of a study. On Day 1, mice were injected in the right quadriceps with 50 μL mRNA-LNP formulation (10 μg mRNA dose was used unless stated otherwise.) For experiments involving two vaccinations, mice were additionally injected in the left quadriceps with 50 μL mRNA-LNP formulation for booster immunizations. Mice were euthanized at day 10-21 (as indicated), at which time blood was collected via intracardiac stick and spleens were dissected and collected for processing. Serum was separated from blood in MiniCollect serum separator tubes (Greiner Bio-One 450472) by centrifugation at 4° C., 1200×g, for 10 minutes. Fresh serum was stored at 4° C. and used to evaluate immunogenicity by ELISA and neutralization assay, the remainder was aliquoted and frozen at −80° C.

Spike titer ELISA assay: The ELISA protocol was adapted from one previously established by Amanat, et al. (Nat Med 26: 1033-1036, 2020). Briefly, 96-well Immulon 4 HBX plates (Thermo Fisher Scientific) were coated with 50 μl per well of a 2 μg/ml solution of SARS-CoV-2 (2019-nCoV) Spike S1+S2 ECD-His recombinant protein (Sino Biological #40589-V08B1) in PBS at 4° C. overnight. Plates were washed three times with 300 μl of 0.1% Tween 20 in PBS (PBS-T), then were blocked for 1 h with 100 μl per well of 3% non-fat milk in PBS-T. Serial dilutions of serum and antibody controls were prepared in 1% non-fat milk in PBS-T, and 100 μl of each was added to the plates for 2 h at room temperature. The wells then were washed thrice in PBS-T as before. Wells were then incubated in 100 μl of a 1:3,000 dilution of goat anti-mouse IgG horseradish peroxidase-conjugated secondary antibody (Sigma) in 1% milk PBS-T room temperature for 1 hour. Plates were again washed thrice in PBS-T. 100 μl SIGMAFAST OPD (Sigma-Aldrich) solution was added to each well for 10 min at room temperature for 10 min. Reactions were stopped by addition of 50 μl per well of 3 M hydrochloric acid. Optical density was measured at 490 nm using a GloMax Discover (Promega) plate reader. End-point titers were determined by taking the last dilution before the signal dropped below 1 standard deviation above the average of the signal from the untreated control serum at the same dilution. The last dilution was taken as the titer if the signal never dropped below this threshold. If no signal above the threshold was detected, the value in the dilution series before the least-dilute sample tested was used. A chimeric monoclonal antibody reactive to the RBD of both SARS-CoV-1 and SARS-CoV-2, and a SARS-CoV-1 reactive mouse monoclonal antibody were used as positive and negative controls, respectively.

Pseudotype neutralization assay: Human ACE2-overexpressing HEK cells (Integral Molecular) used for viral transduction experiments were maintained in high glucose GlutaMAX-containing DMEM (ThermoFisher Scientific 10564) supplemented with 1 μg/mL puromycin, 10% heat-inactivated fetal bovine serum and 100 U/mL penicillin/streptomycin. 4 μl (for 1:37.5 dilution) or 1 μl (for 1:500 dilution) of each serum was mixed with 35 μl spike-pseudotyped GFP-encoding reporter viral particles built using a second-generation lentiviral system (Integral Molecular, lot CG-113A) in puromycin-free culture media to a total volume of 100 μl. Virus and serum were incubated in a 96-well cell culture plate at 37° C. for 1.5 h. 20,000 freshly harvested HEK cells were then added in 50 μL puromycin-free culture media, and transduction was allowed to proceed for 3 days. The Cytation 5 Cell Imaging Multi-Mode Reader and Gen5 software (BioTek) were used to quantify the number of GFP-positive cells. Images were taken of each well using a 4×PL ACH objective in the GFP (469, 525) channel with the LED set to 10.0, an integration time of 100 msec, and gain set to 11.0. Images were taken at a fixed focal height 345 μm below the plate. 6 images were taken per well with automatic overlap to allow the software to stitch them together. Image preprocessing was applied using a dark background and background flattening with a rolling ball diameter of 60 μm. For cellular analysis a primary mask was applied to the processed images with a dark background and a GFP threshold of 2000. Minimum and maximum object sizes were set to 10 μm and 1000 μm, respectively. Split touching objects, fill holes in mask, include edge objects, and analyze entire image were set to ON. Using these parameters, the software calculated a cell count to give the number of GFP-positive cells per well.

ACE2:RBD inhibition assay: The ability of vaccinated sera to inhibit ACE2:RBD binding was measured essentially as described in Nie, et al. (Nat Biotech 15: 3699-3715, 2020), using the SARS-CoV-2 Surrogate Virus Neutralization Test kit (GenScript).

Equivalents

Those skilled in the art will recognize, or be able to ascertain using no more than routine experimentation, many equivalents to the specific embodiments of the invention described herein. It is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Further, it should also be understood that any embodiment or aspect of the invention can be explicitly excluded from the claims, regardless of whether the specific exclusion is recited in the specification. The scope of the present invention is not intended to be limited to the above Description, but rather is as set forth in the claims that follow.

Exemplary Embodiments

Embodiment 1. A fusion polypeptide comprising:
- (i) a fragment antigen that comprises an epitope of a target protein antigen; and
- (ii) a complement C3d-binding polypeptide from an immunoglobulin-binding protein (Sbi) of *Staphylococcus aureus*.

Embodiment 2. The fusion polypeptide of embodiment 1, wherein the complement C3d-binding polypeptide is or comprises one or both of domain III and domain IV of the Sbi of *Staphylococcus aureus*, or a functional fragment or a variant thereof.

Embodiment 3. The fusion polypeptide of embodiment 1 or 2, wherein the fragment antigen has an amino acid sequence length of at least 5%, 10%, 20%, 30%, 40%, 50%, 60%, 70%, 80%, 90% or 95% compared to the amino acid sequence length of the target protein antigen.

Embodiment 4. The fusion polypeptide of embodiment 1 or 2, wherein the fragment antigen has an amino acid sequence length of no more than 50% of the amino acid sequence length of the target protein antigen.

Embodiment 5. The fusion polypeptide of embodiment 4, wherein the fragment antigen has an amino acid sequence length of no more than 40%, 30%, 20%, 10% or 5% of the amino acid sequence length of the target protein antigen.

Embodiment 6. The fusion polypeptide of any one of embodiments 1-5, wherein the fragment antigen has about 10-300 amino acid residues in length.

Embodiment 7. The fusion polypeptide of embodiment 6, wherein the fragment antigen has at least 10 amino acid residues in length.

Embodiment 8. The fusion polypeptide of embodiment 6, wherein the fragment antigen has less than about 300 amino acid residues in length.

Embodiment 9. The fusion polypeptide of any one of embodiments 1-5, wherein the fragment antigen has about 10-300, 10-250, 10-200, 10-150, 10-100, 10-90, 10-80, 10-70, 10-60, 10-50, 10-40, 10-30, 10-20, 20-300, 30-300, 40-300, 50-300, 60-300, 70-300, 80-300, 90-100, 100-300, 150-300, 200-300, 250-300, 20-250, 30-200, 40-150, 50-100, 60-90, or 70-80 amino acids residues in length.

Embodiment 10. The fusion polypeptide of any one of embodiments 1-5, wherein the fragment antigen has about 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 amino acids residues in length.

Embodiment 11. A fusion polypeptide comprising:
- (i) an antigen variant or a fragment antigen variant that comprises an epitope of a target protein antigen; and
- (ii) a complement C3d-binding polypeptide from an immunoglobulin-binding protein (Sbi) of *Staphylococcus aureus*.

Embodiment 12. The fusion polypeptide of embodiment 11, wherein the complement C3d-binding polypeptide is or comprises one or both of domain III and domain IV of the Sbi of *Staphylococcus aureus*, or a functional fragment or a variant thereof.

Embodiment 13. The fusion polypeptide of embodiment 11 or 12, wherein the antigen variant or fragment antigen variant amino acid sequence length is identical to the amino acid sequence length of the target protein antigen.

Embodiment 14. The fusion polypeptide of any one of embodiments 11-13, wherein the antigen variant or fragment antigen variant comprises at least one modified amino acid compared to the target protein antigen.

Embodiment 15. The fusion polypeptide of embodiment 14, wherein the modified amino acid comprises N-linked glycosylation.

Embodiment 16. The fusion polypeptide of any one of embodiments 11-15, wherein the antigen variant or fragment antigen variant comprises at least one amino acid mutation compared to the target protein antigen.

Embodiment 17. The fusion polypeptide of embodiment 16, wherein the antigen variant or fragment antigen variant comprises 2, 3, 4, 5, 6, 7, 8, 9, 10, 15, 20, 30, 40 or 50 amino acid mutations compared to the target protein antigen.

Embodiment 18. The fusion polypeptide of embodiment 16 or 17, wherein the mutation introduces a Serine, a Threonine, an Alanine, or an amino acid at a particular position which is different from the amino acid present at that position in the target protein antigen.

Embodiment 19. The fusion polypeptide of any one of embodiments 16-18, wherein the mutation prevents formation of a disulfide bond.

Embodiment 20. The fusion polypeptide of any one of the preceding embodiments, wherein the fragment antigen is characterized in that when expressed in vivo, it binds to a Major Histocompatibility Complex (MHC) molecule.

Embodiment 21. The fusion polypeptide of any one of embodiments 1-19, wherein the fragment antigen is characterized in that when expressed in vivo, it does not bind to a MHC molecule.

Embodiment 22. The fusion polypeptide of embodiment 20 or 21, wherein the MHC molecule is or comprises a MHC I molecule or a MHC II molecule.

Embodiment 23. The fusion polypeptide of any one of the preceding embodiments, wherein the fragment antigen is characterized in that when expressed in vivo, it folds into a three-dimensional conformation that is substantially identical to the three-dimensional conformation of the fragment antigen as it is in its native position in the target protein antigen.

Embodiment 24. The fusion polypeptide of any one of the preceding embodiments, wherein the fragment antigen, antigen variant or fragment antigen variant further comprises an amino acid sequence from a second target protein antigen.

Embodiment 25. The fusion polypeptide of any one of the preceding embodiments, wherein the target protein antigen is or comprises an infectious disease antigen.

Embodiment 26. The fusion polypeptide of embodiment 25, wherein the infectious disease antigen is or comprises a viral antigen, a bacterial antigen, a fungal antigen, or combinations thereof.

Embodiment 27. The fusion polypeptide of embodiment 26, wherein the target protein antigen is or comprises a cancer antigen.

Embodiment 28. The fusion polypeptide of embodiment 27, wherein the antigen is or comprises a viral antigen.

Embodiment 29. The fusion polypeptide of embodiment 26, wherein the viral antigen is or comprises an influenza antigen.

Embodiment 30. The fusion polypeptide of embodiment 29, wherein the viral antigen is or comprises a coronavirus polypeptide.

Embodiment 31. The fusion polypeptide of embodiment 30, wherein the coronavirus polypeptide is or comprises a SARS-CoV-2 protein.

Embodiment 32. The fusion polypeptide of embodiment 31, wherein the SARS-CoV-2 protein is or comprises a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof; an accessory factor polypeptide or fragment thereof; or any combination thereof.

Embodiment 33. The fusion polypeptide of embodiment 31 or 32, wherein the SARS-CoV-2 protein comprises a Spike protein or a fragment thereof (e.g., RBD).

Embodiment 34. The fusion polypeptide of any one of embodiments 1-33, wherein the fragment antigen, antigen variant or fragment antigen variant has an amino acid sequence at least 80%, 85%, 90%, 91%, 92%, 93%, 94%, 95%, 96%, 97%, 98%, 99% or 100% identity to the amino acid sequence of SEQ ID NO: 3.

Embodiment 35. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 4.

Embodiment 36. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 5.

Embodiment 37. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, 98%, 99% or 100% identity to the amino acid sequence of SEQ ID NO: 6.

Embodiment 38. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 7.

Embodiment 39. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 20.

Embodiment 40. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 21.

Embodiment 41. The fusion polypeptide of any one of embodiments 1-3, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 22.

Embodiment 42. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 23.

Embodiment 43. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 24.

Embodiment 44. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 25.

Embodiment 45. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO:26.

Embodiment 46. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 27.

Embodiment 47. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 28.

Embodiment 48. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 29.

Embodiment 49. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 30.

Embodiment 50. The fusion polypeptide of any one of embodiments 1-33, wherein the fragment antigen, antigen variant or fragment antigen variant has at least 80%, 85%, 90%, 91%, 92%, 93%, 94%, 95%, 96%, 97%, or 100% identity to the amino acid sequence of SEQ ID NO: 31.

Embodiment 51. The fusion polypeptide of any one of embodiments 1-33, wherein the fragment antigen, antigen variant or fragment antigen variant has at least 80%, 85%, 90%, or 100% identity to the amino acid sequence of SEQ ID NO: 8.

Embodiment 52. The fusion polypeptide of any one of the preceding embodiments, wherein the complement C3d-binding polypeptide comprises an Sbi domain III having at least 80%, 85%, 90%, 91%, 92%, 93%, 94%, 95%, 96%, 97%, or 100% identity to the amino acid sequence of SEQ ID NO: 9.

Embodiment 53. The fusion polypeptide of any one of the preceding embodiments, wherein the complement C3d-binding polypeptide comprises an Sbi domain IV having at least 80%, 85%, 90%, 91%, 92%, 93%, 94%, 95%, 96%, 97%, or 100% identity to the amino acid sequence of SEQ ID NO: 10.

Embodiment 54. The fusion polypeptide of any one of the preceding embodiments, wherein the Sbi domain III and the Sbi domain IV are contiguous.

Embodiment 55. The fusion polypeptide of any one of embodiments 2-54, wherein the Sbi domain III and the Sbi domain IV are separated by a linker.

Embodiment 56. The fusion polypeptide of any one of the preceding embodiments, wherein (a) and (b) are encoded by a nucleotide sequence and are disposed in the same nucleotide sequence or in different nucleotide sequences.

Embodiment 57. The fusion polypeptide of any one of the preceding embodiments, wherein (a) is disposed N-terminus of (b).

Embodiment 58. The fusion polypeptide of any one of embodiments 1-56, wherein (a) is disposed C-terminus of (b).

Embodiment 59. The fusion polypeptide of any one of the preceding embodiments, wherein (a) and (b) are contiguous or separated by a linker.

Embodiment 60. The fusion polypeptide of embodiment 59, wherein the linker is a peptidyl linker.

Embodiment 61. The fusion polypeptide of embodiment 60, wherein the peptidyl linker comprises at least 60% glycine and/or serine.

Embodiment 62. The fusion polypeptide of embodiment 60, wherein the linker is chosen from a Gly-Gly-Gly-Gly-Ser (Gly4-Ser) linker, or a Histidine linker.

Embodiment 63. The fusion polypeptide of embodiment 62, wherein the linker is a Gly4-Ser linker.

Embodiment 64. The fusion polypeptide of embodiment 63, wherein the linker comprises 1, 2, 3, 4, 5, 6, 7, 8, 9, or 10 repeats of the Gly4-Ser linker.

Embodiment 65. The fusion polypeptide of embodiment 64, wherein the linker comprises 3 repeats of the Gly4-Ser linker.

Embodiment 66. The fusion polypeptide of any one of embodiments 62-65, wherein the linker comprises the sequence of SEQ ID NO: 11.

Embodiment 67. The fusion polypeptide of any one of embodiments 1-66, wherein the polypeptide further comprises a secretion peptide.

Embodiment 68. The fusion polypeptide of embodiment 67, wherein the secretion peptide is about 10-30 amino acids in length.

Embodiment 69. The fusion polypeptide of embodiment 67 or 68, wherein the secretion peptide is about 10, 11, 12, 13, 14, 15, 16, 17, 18, 19, 20, 21, 22, 23, 24, 25, 26, 27, 28, 29 or 30 amino acids in length.

Embodiment 70. The fusion polypeptide of any one of embodiments 67-69, wherein the secretion peptide comprises an amino acid having at least 80%, 85%, 90%, or 100% identity to the amino acid sequence of SEQ ID NO: 1.

Embodiment 71. The fusion polypeptide of any one of embodiments 67-69, wherein the secretion peptide comprises an amino acid having at least 80%, 85%, 90%, or 100% identity to the amino acid sequence of SEQ ID NO: 2.

Embodiment 72. The fusion polypeptide of any one of the preceding embodiments, wherein the polypeptide has at least 80%, 85%, 90%, 91%, 92%, 93%, 94%, 95%, 96%, 97%, 98%, 99% or 100% identity to the amino acid sequence of SEQ ID NO: 12.

Embodiment 73. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 13.

Embodiment 74. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 14.

Embodiment 75. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 15.

Embodiment 76. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 16.

Embodiment 77. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 17.

Embodiment 78. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 18.

Embodiment 79. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 19.

Embodiment 80. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 32.

Embodiment 81. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 33.

Embodiment 82. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 34.

Embodiment 83. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:35.

Embodiment 84. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:36.

Embodiment 85. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:37.

Embodiment 86. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:38.

Embodiment 87. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:39.

Embodiment 88. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:40.

Embodiment 89. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:41.

Embodiment 90. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:42.

Embodiment 91. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 43.

Embodiment 92. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO: 44.

Embodiment 93. The fusion polypeptide of any one of embodiments 1-71, wherein the polypeptide has at least 80%, 85%, 90%, 91%, 92%, 93%, 94%, 95%, 96%, 97%, 98%, 99% or 100% identity to the amino acid sequence of SEQ ID NO:45.

Embodiment 94. The fusion polypeptide of any one of the preceding embodiments, wherein the polypeptide is encoded by a polynucleotide which is or comprises RNA.

Embodiment 95. The fusion polypeptide of embodiment 94, wherein the polynucleotide is or comprises messenger RNA.

Embodiment 96. The fusion polypeptide of any one of the preceding embodiments, wherein the polypeptide is encoded by a polynucleotide which is or comprises DNA.

Embodiment 97. A fusion polynucleotide encoding the fusion polypeptide of any one of embodiments 1-96.

Embodiment 98. A fusion polynucleotide comprising a nucleotide sequence encoding:

a fragment antigen that comprises an epitope of a target protein antigen; and (ii) a complement C3d-binding polypeptide from an immunoglobulin-binding protein (Sbi) of *Staphylococcus aureus*.

Embodiment 99. A fusion polynucleotide comprising a nucleotide sequence encoding:

(i) an antigen variant or a fragment antigen variant that comprises an epitope of a target protein antigen; and (ii) a complement C3d-binding polypeptide from an immunoglobulin-binding protein (Sbi) of *Staphylococcus aureus*.

Embodiment 100. The fusion polynucleotide of embodiment 98 or 99, wherein the polynucleotide is or comprises RNA.

Embodiment 101. The fusion polynucleotide of embodiment 100, wherein the polynucleotide is or comprises messenger RNA.

Embodiment 102. The fusion polynucleotide of any one of embodiments 98-101, wherein the polynucleotide is or comprises DNA.

Embodiment 103. The fusion polynucleotide of embodiment 98, wherein the complement C3d-binding polypeptide is or comprises one or both of domain III and domain IV of the Sbi of *Staphylococcus aureus*, or a functional fragment or a variant thereof.

Embodiment 104. The fusion polynucleotide of embodiment 98 or 99, wherein the polynucleotide encodes a fragment antigen that has an amino acid sequence length of at least 5%, 10%, 20%, 30%, 40%, 50%, 60%, 70%, 80%, 90% or 95% compared to the amino acid sequence length of the target protein antigen.

Embodiment 105. The fusion polynucleotide of embodiment 98 or 99, wherein the polynucleotide encodes a fragment antigen that has an amino acid sequence length of no more than 50% of the amino acid sequence length of the target protein antigen.

Embodiment 106. The fusion polynucleotide of embodiment 105, wherein the polynucleotide encodes a fragment antigen has an amino acid sequence length of no more than 40%, 30%, 20%, 10% or 5% of the amino acid sequence length of the target protein antigen.

Embodiment 107. The fusion polynucleotide of embodiment 99, wherein the polynucleotide encodes an antigen variant or fragment antigen variant having an amino acid sequence length that is identical to the amino acid sequence length of the target protein antigen.

Embodiment 108. The fusion polynucleotide of embodiment 99 or 107, wherein the polynucleotide encodes an antigen variant or fragment antigen variant which comprises at least one modified amino acid compared to the target protein antigen.

Embodiment 109. The fusion polynucleotide of any one of embodiments 98-108, wherein the polynucleotide encodes a fragment antigen which is characterized in that when expressed in vivo, it binds to a Major Histocompatibility Complex (MHC) molecule.

Embodiment 110. The fusion polynucleotide of any one of embodiments 98-109, wherein the polynucleotide encodes a fragment antigen which is characterized in that when expressed in vivo, it does not bind to a MHC molecule.

Embodiment 111. The fusion polynucleotide of embodiment 109 or 110, wherein the MHC molecule is or comprises a MHC I molecule or a MHC II molecule.

Embodiment 112. The fusion polynucleotide of any one of embodiments 98-111, wherein the polynucleotide encodes a fragment antigen which is characterized in that when expressed in vivo, it folds into a three-dimensional conformation that is substantially identical to the three-dimensional conformation of the fragment antigen as it is in its native position in the target protein antigen.

Embodiment 113. The fusion polynucleotide of any one of embodiments 98-112, wherein the polynucleotide encodes a fragment antigen, antigen variant or fragment antigen variant which further comprises an amino acid sequence from a second target protein antigen.

Embodiment 114. The fusion polynucleotide of any one of the preceding embodiments, wherein the target protein antigen is or comprises an infectious disease antigen.

Embodiment 115. The fusion polynucleotide of embodiment 114, wherein the infectious disease antigen is or comprises a viral antigen, a bacterial antigen, a fungal antigen, or combinations thereof.

Embodiment 116. The fusion polynucleotide of embodiment of any one of embodiments 98-113, wherein the target protein antigen is or comprises a cancer antigen.

Embodiment 117. The fusion polynucleotide of embodiment 114, wherein the antigen is or comprises a viral antigen.

Embodiment 118. The fusion polynucleotide of embodiment 114, wherein the viral antigen is or comprises an influenza antigen.

Embodiment 119. The fusion polynucleotide of embodiment 114, wherein the viral antigen is or comprises a coronavirus polypeptide.

Embodiment 120. The fusion polynucleotide of embodiment 119, wherein the coronavirus polypeptide is or comprises a SARS-CoV-2 protein.

Embodiment 121. The fusion polynucleotide of embodiment 120, wherein the SARS-CoV-2 protein is or comprises a Spike protein (SARS-CoV-2 S) or fragment thereof; an Envelope protein (SARS-CoV-2 E) or fragment thereof; a Membrane protein (SARS-CoV-2 M) or fragment thereof; a nucleocapsid protein (SARS-CoV-2 N) or fragment thereof; an accessory factor polypeptide or fragment thereof; or any combination thereof.

Embodiment 122. The fusion polynucleotide of embodiment 120 or 121, wherein the SARS-CoV-2 protein comprises a Spike protein or a fragment thereof (e.g., RBD).

Embodiment 123. The fusion polynucleotide of any one of embodiments 98-122, wherein (a) is disposed C-terminus of (b).

Embodiment 124. The fusion polynucleotide of any one of embodiments 98-123, wherein (a) and (b) are contiguous or separated by a nucleotide sequence encoding a linker.

Embodiment 125. The fusion polynucleotide of embodiment 124, wherein the linker is a peptidyl linker.

Embodiment 126. The fusion polynucleotide of embodiment 125, wherein the peptidyl linker comprises at least 60% glycine and/or serine.

Embodiment 127. The fusion polynucleotide of embodiment 126, wherein the linker is chosen from a Gly-Gly-Gly-Gly-Ser (Gly4-Ser) linker, or a Histidine linker.

Embodiment 128. The fusion polynucleotide of any one of embodiments 98-127, wherein the polynucleotide further comprises a nucleotide sequence encoding a secretion peptide.

Embodiment 129. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 46.

Embodiment 130. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 47.

Embodiment 131. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 48.

Embodiment 132. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 49.

Embodiment 133. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 50.

Embodiment 134. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 51.

Embodiment 135. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 52.

Embodiment 136. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 53.

Embodiment 137. The fusion polynucleotide of any one of embodiments 98-128, wherein the polynucleotide has at least 80%, 85%, 90%, 91%, 92%, 93%, 94%, 95%, 96%, 97%, 98%, 99% or 100% identity to the nucleotide sequence of SEQ ID NO: 54.

Embodiment 138. An expression vector comprising the fusion polynucleotide of any one of embodiments 97-137.

Embodiment 139. The expression vector of embodiment 138, wherein the expression vector comprises a viral vector.

Embodiment 140. The expression vector of embodiment 138 or 139, wherein the viral vector comprises a retrovirus vector, an adenovirus vector, an adeno-associated virus vector or a lentivirus vector or an RNA vector.

Embodiment 141. A composition for delivering the fusion polypeptide of any one of embodiments 1-96.

Embodiment 142. A composition for delivering the fusion polynucleotide of any one of embodiments 97-137.

Embodiment 143. A pharmaceutical composition that delivers the fusion polypeptide of any one of embodiments 1-96, the fusion polynucleotide of any one of embodiments 97-137, or the expression vector of any one of embodiments 138-140.

Embodiment 144. The pharmaceutical composition of embodiment 143, further comprising a pharmaceutically acceptable excipient, a diluent, or a combination thereof.

Embodiment 145. A method of making comprising:

recombinantly joining a first nucleotide sequence that encodes a fragment antigen comprising an epitope of a target protein antigen, and a second nucleotide sequence that encodes a complement C3d-binding polypeptide from a immunoglobulin-binding protein (Sbi) of *Staphylococcus aureus* to form a polynucleotide comprising the first nucleotide sequence and the second nucleotide sequence.

Embodiment 146. The method of embodiment 145, further comprising expressing the polynucleotide in a cell to produce a fusion polypeptide encoded by the polynucleotide.

Embodiment 147. A cell comprising the fusion polypeptide of any one of embodiments 1-96, the fusion polynucleotide of any one of embodiments 97-137, or the expression vector of any one of embodiments 138-140.

Embodiment 148. The cell of embodiment 147, wherein the cell is contacted with the fusion polynucleotide, fusion polypeptide or expression vector.

Embodiment 149. The cell of embodiment 147 or 148, wherein the contacting occurs in vivo, in vitro or ex vivo.

Embodiment 150. A kit comprising the fusion polypeptide of any one of embodiments 1-96, the fusion polynucleotide of any one of embodiments 97-137, the expression vector of any one of embodiments 138-140, or the pharmaceutical composition of embodiment 143 or 144, and instructions for use.

Embodiment 151. The kit of embodiment 150, further comprising: a polynucleotide comprising a nucleotide sequence that encodes a target protein antigen; or a target protein antigen encoded by the polynucleotide.

Embodiment 152. A method comprising administering to a subject in need thereof at least one dose of the pharmaceutical composition of embodiment 143 or 144.

Embodiment 153. The method of embodiment 152, wherein the at least one dose is administered in an effective amount to induce an immune response against the fragment antigen in the subject.

Embodiment 154. The method of embodiment 153, wherein the immune response comprises generation of a neutralizing antibody titer against the fragment antigen.

Embodiment 155. The method of embodiment 154, wherein the neutralizing antibody titer is increased by at least 50%, as compared to a neutralizing antibody titer induced by a fragment antigen in the absence of the complement C3d-binding polypeptide from an immunoglobulin-binding protein (Sbi) of *Staphylococcus aureus*.

Embodiment 156. The method of embodiment 154 or 155, wherein the generation of a neutralizing antibody titer has been established in a mouse model using a dose of at least 0.1 μg.

Embodiment 157. The method of any one of embodiments 152 to 156, wherein the at least one dose is administered in an effective amount to stimulate B cells while reducing induction of T cell response.

Embodiment 158. A method comprising administering to a subject:

a) a first dose of the pharmaceutical composition of embodiment 143 or 144; and b) a second dose of the pharmaceutical composition of embodiment 143 or 144.

Embodiment 159. The method of embodiment 158, wherein the first dose and the second dose are administered by at least 3 days, 4 days, 5 days, 6 days, 7 days, 2 weeks, 3 weeks, or 4 weeks apart.

Embodiment 160. The method of embodiment 158 or 159, wherein the first dose and the second dose are in the same amount.

Embodiment 161. The method of embodiment 158 or 159, wherein the first dose and the second dose are in different amounts.

Embodiment 162. A method comprising:

administering to a subject in need thereof a dose of the pharmaceutical composition of embodiment 143 or 144, such that the subject receives:

a first dose of a pharmaceutical composition that delivers a polynucleotide comprising a nucleotide sequence that encodes a target protein antigen or a target protein antigen encoded by the polynucleotide; and a second dose of the pharmaceutical composition of embodiment 143 or 144.

Embodiment 163. The method of embodiment 162, wherein:

(a) the polynucleotide comprising a nucleotide sequence that encodes a target protein antigen further comprises a nucleotide sequence encoding a complement C3d-binding polypeptide from an immunoglobulin-binding protein (Sbi) of *Staphylococcus aureus*; or (b) the target protein antigen encoded by the polynucleotide further comprises a complement C3d-binding polypeptide from an immunoglobulin-binding protein (Sbi) of *Staphylococcus aureus.*

Embodiment 164. The method of embodiment 162 or 163, further comprising, prior to the administering step, administering to the subject the first dose of the pharmaceutical composition that delivers a polynucleotide comprising a nucleotide sequence that encodes a target protein antigen or a target protein antigen encoded by the polynucleotide.

Embodiment 165. A method comprising:

administering to a subject in need thereof a dose of the pharmaceutical composition of embodiment 143 or 144, such that the subject receives:

a first dose of the pharmaceutical composition of embodiment 143 or 144, and a second dose of a pharmaceutical composition that delivers a polynucleotide comprising a nucleotide sequence that encodes a target protein antigen or a target protein antigen encoded by the polynucleotide.

Embodiment 166. The method of embodiment 165, wherein:

(a) the polynucleotide comprising a nucleotide sequence that encodes a target protein antigen further comprises a nucleotide sequence encoding a complement C3d-binding polypeptide from an immunoglobulin-binding protein (Sbi) of *Staphylococcus aureus*; or (b) the target protein antigen encoded by the polynucleotide further comprises a complement C3d-binding polypeptide from an immunoglobulin-binding protein (Sbi) of *Staphylococcus aureus.*

Embodiment 167. A method comprising:

administering to a subject in need thereof a dose of the pharmaceutical composition of embodiment 143 or 144, such that the subject receives:

a first dose of a pharmaceutical composition that delivers a polynucleotide comprising a nucleotide sequence that encodes a fusion polypeptide comprising (i) a target protein antigen and (ii) a complement C3d-binding polypeptide from an immunoglobulin-binding protein (Sbi) of *Staphylococcus aureus*; or a fusion polypeptide encoded by the polynucleotide; and a second dose of the pharmaceutical composition of embodiment 143 or 144.

Embodiment 168. The method of embodiment 167, further comprising, prior to the administering step, administering to the subject the first dose of the pharmaceutical composition that delivers a polynucleotide comprising a nucleotide sequence that encodes a fusion polypeptide comprising (i) a target protein antigen and (ii) a complement C3d-binding polypeptide from an immunoglobulin-binding protein (Sbi) of *Staphylococcus aureus*; or a fusion polypeptide encoded by the polynucleotide.

Embodiment 169. The method of any one of embodiments 162-167, wherein the first dose and the second dose are administered by at least 3 days, 4 days, 5 days, 6 days, 7 days, 2 weeks, 3 weeks, or 4 weeks apart.

Embodiment 170. The method of any one of embodiments 152-159, wherein the subject in need thereof is a subject who is suffering from or is susceptible to a disease, disorder, or condition induced by the target protein antigen.

Embodiment 171. The method of any one of embodiments 152-170, wherein the subject is a mammalian subject.

Embodiment 172. The method of embodiment 171, wherein the subject is a human subject.

Embodiment 173. The method of any one of embodiments 152-172, wherein the administration can be performed by intramuscular administration, intradermal administration, intravenous administration, subcutaneous administration, or combinations thereof.

Embodiment 174. A composition comprising the fusion polypeptide of any one of embodiments 1-96, or the fusion polynucleotide of any one of embodiments 97-137, or the pharmaceutical composition of embodiment 143 or 144, for use in enhancing the immunogenicity of an antigen.

Embodiment 175. A composition comprising the fusion polypeptide of any one of embodiments 1-96, or the fusion polynucleotide of any one of embodiments 97-137, or the pharmaceutical composition of embodiment 143 or 144, for use in stimulating an immune response against an antigen.

Embodiment 176. A composition comprising the fusion polypeptide of any one of embodiments 1-96, or the fusion polynucleotide of any one of embodiments 97-137, or the pharmaceutical composition of embodiment 143 or 144, for use in method of treating a disease or ameliorating a symptom of a disease.

Embodiment 177. A method for enhancing the immunogenicity of an antigen, comprising administering to a subject in need thereof, the fusion polypeptide of any one of embodiments 1-96, or the fusion polynucleotide of any one of embodiments 97-137, or the pharmaceutical composition of embodiment 143 or 144.

Embodiment 178. A method for stimulating an immune response against an antigen, comprising administering to a subject in need thereof, the fusion polypeptide of any one of embodiments 1-96, or the fusion polynucleotide of any one of embodiments 97-137, or the pharmaceutical composition of embodiment 143 or 144.

Embodiment 179. A method of treating a disease or ameliorating a symptom of a disease comprising administering to a subject in need thereof, the fusion polypeptide of any one of embodiments 1-96, or the fusion polynucleotide of any one of embodiments 97-137, or the pharmaceutical composition of embodiment 143 or 144.

Embodiment 180. Use of a composition comprising the fusion polypeptide of any one of embodiments 1-96, or the fusion polynucleotide of any one of embodiments 97-137, or the pharmaceutical composition of embodiment 143 or 144, in the preparation of a medicament for enhancing the immunogenicity of a fragment antigen.

Embodiment 181. Use of a composition comprising the fusion polypeptide of any one of embodiments 1-96, or the fusion polynucleotide of any one of embodiments 97-137, or the pharmaceutical composition of embodiment 143 or 144, in the preparation of a medicament for stimulating an immune response against a antigen.

Embodiment 182. Use of a composition the fusion polypeptide of any one of embodiments 1-96, or the fusion polynucleotide of any one of embodiments 97-137, or the pharmaceutical composition of embodiment 143 or 144, in the preparation of a medicament for treating a disease or ameliorating a symptom of a disease.

Embodiment 183. Use of a composition comprising the fusion polypeptide of any one of embodiments 1-96, or the fusion polynucleotide of any one of embodiments 97-137, or the pharmaceutical composition of embodiment 143 or 144, for enhancing the immunogenicity of a fragment antigen.

Embodiment 184. Use of a composition comprising the fusion polypeptide of any one of embodiments 1-96, or the fusion polynucleotide of any one of embodiments 97-137, or the pharmaceutical composition of embodiment 143 or 144, for stimulating an immune response against a antigen.

Embodiment 185. Use of a composition the fusion polypeptide of any one of embodiments 1-96, or the fusion polynucleotide of any one of embodiments 97-137, or the pharmaceutical composition of embodiment 143 or 144, for treating a disease or ameliorating a symptom of a disease.

Embodiment 186. The composition for use of any one of embodiments 174-176, the method of any one of embodiments 177-179, or the use of any one of embodiments 180-186, wherein the subject is a mammal.

Embodiment 187. The composition for use, method or use of embodiment 186, wherein the subject is a human.

Embodiment 188. The composition for use of any one of embodiments 174-176, the method of any one of embodiments 177-179, or the use of any one of embodiments 180-186, wherein a single dose of the fusion polypeptide, fusion polynucleotide or pharmaceutical composition is administered.

Embodiment 189. The composition for use of any one of embodiments 174-176, the method of any one of embodiments 177-179, or the use of any one of embodiments 180-186, wherein a plurality of doses of the fusion polypeptide, fusion polynucleotide or pharmaceutical composition is administered.

Embodiment 190. The composition for use of any one of embodiments 174-176, the method of any one of embodiments 177-179, or the use of any one of embodiments 180-186, wherein the fusion polypeptide, fusion polynucleotide or pharmaceutical composition is administered at a dose of about 0.5 micrograms to 10 micrograms.

Embodiment 191. The composition for use of any one of embodiments 174-176, the method of any one of embodiments 177-179, or the use of any one of embodiments 180-186, wherein administration of the fusion polynucleotide, fusion polypeptide or pharmaceutical composition results in a humoral response.

Embodiment 192. The composition for use, method or use of embodiment 190, wherein the humoral response is an antibody response.

Embodiment 193. The composition for use of any one of embodiments 174-176, the method of any one of embodiments 177-179, or the use of any one of embodiments 180-186, wherein administration of the fusion polynucleotide, fusion polypeptide or pharmaceutical composition results in an increased titer of an antibody response.

Embodiment 194. The composition for use, method or use of embodiment 193, wherein the increase in titer is an increase of about 10 fold to about 500 fold.

Embodiment 195. The composition for use, method or use of embodiment 193 or 194, wherein the increased titer of the antibody response is compared to administration of an otherwise similar fusion polynucleotide that does not comprise an Sbi domain III, or a fragment or variant thereof; and Sbi domain IV, or a fragment or a variant thereof.

Embodiment 196. The composition for use, method or use of embodiment 193 or 194, wherein the increased titer of the antibody response is compared to administration of an otherwise similar fusion polypeptide that does not comprise an Sbi domain III, or a fragment or variant thereof; and an Sbi domain IV, or a fragment or a variant thereof.

Embodiment 197. The composition for use, method or use of embodiment 193 or 194, wherein the increased titer of the antibody response is compared to administration of an otherwise similar pharmaceutical composition that does not comprise a nucleotide sequence encoding Sbi domain III, or a fragment or variant thereof; and Sbi domain IV, or a fragment or a variant thereof.

Embodiment 198. The composition for use of any one of embodiments 174-176, the method of any one of embodiments 177-179, or the use of any one of embodiments 180-186, wherein the composition is administered via any one of the following routes of administration: intramuscular, intravenous, subcutaneous, intrathecal, intradermal, ocular, intranasal, sublingual, or oral.

Embodiment 199. An in vitro method of selecting a fragment antigen by identifying a polypeptide fragment that folds into a three-dimensional conformation that is substantially identical to the three-dimensional conformation as in a target protein antigen from which the fragment is derived.

Embodiment 200. The method of embodiment 199, wherein the method comprises the steps of:

- providing a mammalian cell display system that displays a library of fragment antigen candidates on cell surface;
- exposing the mammalian cell display system to a composition comprising antibodies that bind to a target protein antigen from which the fragment antigen candidates are derived;
- detecting fragment antigen candidates that bind to the target protein antigen-binding antibodies, wherein the binding of a fragment antigen candidate that binds to at least one of the target protein antigen-binding antibodies is indicative of its likelihood to fold into a three-dimensional conformation that is substantially identical to the three-dimensional conformation as in the target protein antigen.

Embodiment 201. The method of embodiment 198 or 199, wherein the method further comprises a step of generating antibodies that bind to the target protein antigen.

Embodiment 202. The method of embodiment 201, wherein the generation of the antibodies comprises (i) immunizing animals with a target protein antigen or a polynucleotide encoding the same from which the fragment antigen candidates are derived; and (ii) identifying antibodies that bind to the target protein antigen.

Embodiment 203. The method of any one of embodiments 200-202, wherein the mammalian cell display system comprises HEK293T cells, HeLa cells, or CHO cells.

Embodiment 204. The method of any one of embodiments 200-203, wherein the polypeptide fragment is identified based on binding affinity to the antibody in a serum binding assay or a similar assay.

Embodiment 205. A recombinant polynucleotide comprising a nucleotide sequence encoding an immunoglobulin-binding protein (Sbi) of *Staphylococcus aureus*, or a fragment thereof.

Embodiment 206. The polynucleotide of embodiment 205, wherein the polynucleotide comprises a sequence encoding a complement C3d-binding polypeptide from Sbi.

Embodiment 207. The polynucleotide of embodiment 206, wherein the complement C3d-binding polypeptide is or comprises one or both of domain III and domain IV of the Sbi of *Staphylococcus aureus*, or a functional fragment or a variant thereof.

Embodiment 208. The polynucleotide of any one of embodiments 205-207, wherein the polynucleotide is or comprises RNA.

Embodiment 209. The polynucleotide of any one of embodiments 205-207, wherein the polynucleotide is or comprises messenger RNA.

Embodiment 210. The polynucleotide of any one of embodiments 205-207, wherein the polynucleotide is or comprises DNA.

Embodiment 211. The polynucleotide of any one of embodiments 205-210, wherein the polynucleotide encodes a polypeptide which has at least 80%, 85%, 90%, 91%, 92%, 93%, 94%, 95%, 96%, 97%, 98%, 99% or 100% identity to the nucleotide sequence of SEQ ID NO: 9.

Embodiment 212. The polynucleotide of any one of embodiments 205-210, wherein the polynucleotide encodes a polypeptide which has at least 80%, 85%, 90%, 91%, 92%, 93%, 94%, 95%, 96%, 97%, 98%, 99% or 100% identity to the nucleotide sequence of SEQ ID NO: 10.

Embodiment 213. An isolated polypeptide comprising an immunoglobulin-binding protein (Sbi) of *Staphylococcus aureus.*

Embodiment 214. The polypeptide of embodiment 213, comprising a complement C3d-binding polypeptide from Sbi.

Embodiment 215. The polypeptide of embodiment 214, wherein the complement C3d-binding polypeptide is or comprises one or both of domain III and domain IV of the Sbi of *Staphylococcus aureus*, or a functional fragment or a variant thereof.

Embodiment 216. The polypeptide of embodiment 214 or 215, wherein the polypeptide has at least 80%, 85%, 90%, 91%, 92%, 93%, 94%, 95%, 96%, 97%, or 100% identity to the amino acid sequence of SEQ ID NO: 9.

Embodiment 217. The polypeptide of embodiment 214 or 215, wherein the polypeptide has at least 80%, 85%, 90%, 91%, 92%, 93%, 94%, 95%, 96%, 97%, or 100% identity to the amino acid sequence of SEQ ID NO: 10.

Embodiment 218. An expression vector comprising the polynucleotide of any one of embodiments 205-212.

Embodiment 219. A composition for delivering the polypeptide of any one of embodiments 213-217.

Embodiment 220. A composition for delivering the polynucleotide of any one of embodiments 205-212.

Embodiment 221. A pharmaceutical composition that delivers the polynucleotide of any one of embodiments 205-212, the polypeptide of any one of embodiments 213-217, or the expression vector of embodiment 218.

Embodiment 222. The pharmaceutical composition of embodiment 221, further comprising a pharmaceutically acceptable excipient, a diluent, or a combination thereof.

Embodiment 223. A method comprising administering to a subject in need thereof at least one dose of the pharmaceutical composition of embodiment 221 or 222.

Embodiment 224. A method for enhancing the immunogenicity of an antigen, comprising administering to a subject in need thereof, the polynucleotide of any one of embodiments 205-212, the polypeptide of any one of embodiments 213-217, or the pharmaceutical composition of embodiment 221 or 222.

Embodiment 225. A method for stimulating an immune response against an antigen, comprising administering to a subject in need thereof, the polynucleotide of any one of embodiments 205-212, the polypeptide of any one of embodiments 213-217, or the pharmaceutical composition of embodiment 221 or 222.

Embodiment 226. Use of an immunoglobulin-binding protein (Sbi) of *Staphylococcus aureus* as an adjuvant in an immunogenic composition.

Embodiment 227. An immunoglobulin-binding protein (Sbi) of *Staphylococcus aureus* for use as an adjuvant in an immunogenic composition.

What is claimed is:

1. A method comprising:

administering to a subject a composition comprising a polynucleotide encoding a fusion polypeptide;

(i) a fragment antigen, an antigen variant, or a fragment antigen variant, that comprises an epitope of a target protein antigen, and (ii) a complement C3d-binding polypeptide from an immunoglobulin-binding protein (Sbi) of *Staphylococcus aureus*.

2. The method of claim 1, wherein the method is a treatment method.

3. The method of claim 1, wherein the subject is a mammal.

4. The method of claim 1, wherein the complement C3d-binding polypeptide is or comprises one or both of domain III and domain IV of the Sbi of *Staphylococcus aureus*, or a functional fragment or a variant thereof.

5. The method of claim 1, wherein the fragment antigen has an amino acid sequence length of:

(i) at least 5% compared to the amino acid sequence length of the target protein antigen, (ii) no more than 50% of the amino acid sequence length of the target protein antigen, (iii) about 10-300 amino acid residues, or (iv) any combination thereof.

6. The method of claim 1, wherein the fragment antigen is characterized in that when expressed in vivo, it folds into a three-dimensional conformation that is substantially identical to the three-dimensional conformation of the fragment antigen as it is in its native position in the target protein antigen.

7. The method of claim 1, wherein the target protein antigen is or comprises:

(i) an infectious disease antigen chosen from a viral antigen, a bacterial antigen, a fungal antigen, or any combination thereof, or (ii) a cancer antigen.

8. The method of claim 1, wherein the viral antigen is or comprises an influenza antigen, or a coronavirus polypeptide.

9. The method of claim 8, wherein the coronavirus polypeptide is or comprises a SARS-COV-2 protein chosen from: a Spike protein (SARS-COV-2 S) or fragment thereof, an Envelope protein (SARS-COV-2 E) or fragment thereof, a Membrane protein (SARS-COV-2 M) or fragment thereof, a nucleocapsid protein (SARS-COV-2 N) or fragment thereof, an accessory factor polypeptide or fragment thereof, or any combination thereof.

10. The method of claim 1, wherein the fragment antigen, antigen variant or fragment antigen variant has an amino acid sequence having at least 80% identity to the amino acid sequence of any one of SEQ ID NOs: 3, 4, 5, 6, 7, 8, 20, 21, 22, 23, 24, 25, 26, 27, 28, 29, 30 or 31.

11. The method of claim 1, wherein the complement C3d-binding polypeptide comprises:

(a) an Sbi domain III having at least 80% identity to the amino acid sequence of SEQ ID NO: 9, (b) an Sbi domain IV having at least 80% identity to the amino acid sequence of SEQ ID NO: 10, or (c) both (a) and (b).

12. The method of claim 11, wherein the Sbi domain III and the Sbi domain IV are contiguous, or are separated by a linker.

13. The method of claim 1, wherein the polynucleotide further comprises a nucleotide sequence encoding a secretion peptide.

14. The method of claim 1, wherein the polynucleotide has at least 80% identity to the nucleotide sequence of any one of SEQ ID NOs: 47, 49, 50, 51, 52, 53, or 54.

15. The method of claim 1, wherein the fusion polypeptide encoded by the polynucleotide has at least 80% identity to the amino acid sequence of any one of SEQ ID NOs: 13, 14, 15, 16, 17, 18, or 19.

16. The method of claim 1, wherein the polynucleotide is RNA.

17. The method of claim 1, wherein the composition is a pharmaceutical composition.

18. The method of claim 1, wherein administration of the polynucleotide or the composition comprising the polynucleotide results in a humoral response.

19. The method of claim 18, wherein the humoral response is an antibody response.

20. The method of claim 19, wherein administration of the polynucleotide or the composition comprising the polynucleotide results in an increased titer of the antibody response.

21. The method of claim 20, wherein the increase in titer is an increase of about 10-fold to about 500-fold.

22. The method of claim 20, wherein the increased titer of the antibody response is compared to administration of an otherwise similar polynucleotide or a composition comprising an otherwise similar polynucleotide that does not comprise an Sbi domain III, or a fragment or variant thereof, and Sbi domain IV, or a fragment or a variant thereof.

23. The method of claim 1, wherein the subject is a subject who is suffering from or is susceptible to a disease, disorder, or condition induced by the target protein antigen.

24. The method of claim 1, wherein the administering can be performed by intramuscular administration, intradermal administration, intravenous administration, subcutaneous administration, or any combination thereof.

25. A method for enhancing the immunogenicity of an antigen, comprising administering to a subject in need thereof, a polynucleotide encoding a fusion polypeptide or a composition comprising a polynucleotide encoding a fusion polypeptide, wherein the fusion polypeptide comprises:

(i) a fragment antigen, an antigen variant, or a fragment antigen variant, that comprises an epitope of a target protein antigen, and (ii) a complement C3d-binding polypeptide from an immunoglobulin-binding protein (Sbi) of *Staphylococcus aureus*, and wherein the immunogenicity for the antigen is enhanced in the subject compared to administration of an otherwise similar polynucleotide, or a composition comprising a polynucleotide that does not comprise a complement C3d-binding polypeptide.

26. The method of claim 25, wherein:

(i) the polynucleotide is RNA, (ii) the composition is a pharmaceutical composition, or (iii) both (i) and (ii).

27. A method for stimulating an immune response against an antigen, comprising administering to a subject in need thereof, a polynucleotide encoding a fusion polypeptide or a composition comprising a polynucleotide encoding a fusion polypeptide, wherein the fusion polypeptide comprises:

(i) a fragment antigen, an antigen variant, or a fragment antigen variant, that comprises an epitope of a target protein antigen, and (ii) a complement C3d-binding polypeptide from an immunoglobulin-binding protein (Sbi) of *Staphylococcus aureus*, and wherein the immune response against the antigen is enhanced in the subject compared to administration of an otherwise similar polynucleotide, or a composition comprising a polynucleotide, that does not comprise a complement C3d-binding polypeptide.

28. The method of claim 27, wherein:

(i) the polynucleotide is RNA, (ii) the composition is a pharmaceutical composition, or (iii) both (i) and (ii).

* * * * *

UNITED STATES PATENT AND TRADEMARK OFFICE
CERTIFICATE OF CORRECTION

Page 1 of 1

PATENT NO. : 12,343,392 B2
APPLICATION NO. : 18/235464
DATED : July 1, 2025
INVENTOR(S) : Kyle Backman et al.

It is certified that error appears in the above-identified patent and that said Letters Patent is hereby corrected as shown below:

In the Claims

At Column 103, Claim number 1, Line number 17, please delete ";" and insert --, wherein the fusion polypeptide comprises:--

Signed and Sealed this
Tenth Day of February, 2026

John A. Squires
*Director of the United States Patent and Trademark Office*